(12) United States Patent
Gault et al.

(10) Patent No.: US 7,875,587 B2
(45) Date of Patent: Jan. 25, 2011

(54) PEPTIDE ANALOGUES OF GIP FOR TREATMENT OF DIABETES, INSULIN RESISTANCE AND OBESITY

(75) Inventors: Victor A. Gault, Coleraine (IE); Finbarr Paul Mary O'Harte, Coleraine (IE); Nigel Irwin, Coleraine (IE); Peter Raymond Flatt, Coleraine (IE)

(73) Assignee: UUTECH Limited, Coleraine (GB)

( * ) Notice: Subject to any disclaimer, the term of this patent is extended or adjusted under 35 U.S.C. 154(b) by 0 days.

(21) Appl. No.: 11/713,892

(22) Filed: Mar. 5, 2007

(65) Prior Publication Data

US 2007/0167370 A1    Jul. 19, 2007

Related U.S. Application Data

(63) Continuation of application No. 11/090,787, filed on Mar. 25, 2005, now abandoned, which is a continuation-in-part of application No. PCT/GB2005/000710, filed on Feb. 25, 2005.

(30) Foreign Application Priority Data

Feb. 25, 2004    (GB)    ................... 0404124.0

(51) Int. Cl.
*A61K 38/10*    (2006.01)
*A61K 38/22*    (2006.01)

(52) U.S. Cl. .............................. 514/12; 514/13; 514/14; 514/21

(58) Field of Classification Search ........................ None
See application file for complete search history.

(56) References Cited

U.S. PATENT DOCUMENTS

| 5,545,618 | A | 8/1996 | Buckley et al. |
| 5,846,937 | A | 12/1998 | Drucker et al. |
| 5,998,204 | A | 12/1999 | Tsien et al. |
| 6,077,822 | A | * | 6/2000 | Dyrsting et al. ................. 514/8 |
| 6,087,476 | A | 7/2000 | Kenten et al. |
| 6,245,320 | B1 | * | 6/2001 | Kim ............................ 424/43 |
| 6,303,661 | B1 | 10/2001 | Demuth et al. |
| 6,410,508 | B1 | 6/2002 | Isales et al. |
| 6,514,500 | B1 | 2/2003 | Bridon et al. |
| 6,849,714 | B1 | 2/2005 | Bridon et al. |

(Continued)

FOREIGN PATENT DOCUMENTS

DE    19921537    8/1994

(Continued)

OTHER PUBLICATIONS

Irwin et al., Degration, Insulin Secretion, and Antihyperglycemica Actions ... Journal of Medicinal Chemistry. Feb. 1, 2005, vol. 48, No. 4, pp. 1244-1250.*

(Continued)

*Primary Examiner*—Jeffrey E Russel
(74) *Attorney, Agent, or Firm*—K&L Gates LLP

(57) ABSTRACT

The present invention provides peptide analogues which are antagonists of gastric inhibitory peptide (GIP). The peptides, based on GIP 1-42 include substitutions and/or modifications which have enhanced resistance to degradation by the enzyme dipeptidyl peptidase IV (DPP IV). The invention also provides a process of N terminally modifying GIP and the use of the peptide analogues for treatment of diabetes.

12 Claims, 58 Drawing Sheets

U.S. PATENT DOCUMENTS

| | | | |
|---|---|---|---|
| 6,852,690 | B1 | 2/2005 | Nauck et al. |
| 6,921,748 | B1 | 7/2005 | O'Harte et al. |
| 7,326,688 | B2 | 2/2008 | O'Harte |
| 7,666,838 | B2 | 2/2010 | O'Harte et al. |
| 2002/0151495 | A1 | 10/2002 | Wolfe et al. |
| 2003/0157107 | A1 | 8/2003 | Miyawaki et al. |
| 2003/0204063 | A1 | 10/2003 | Gravel et al. |
| 2003/0221201 | A1 | 11/2003 | Prior et al. |
| 2003/0232761 | A1* | 12/2003 | Hinke et al. ............ 514/14 |
| 2004/0029805 | A1 | 2/2004 | Wolfe et al. |
| 2004/0228846 | A1 | 11/2004 | Pang et al. |
| 2004/0242853 | A1 | 12/2004 | Greig et al. |
| 2005/0009147 | A1 | 1/2005 | Bauer et al. |
| 2005/0049177 | A1 | 3/2005 | Bachovchin et al. |
| 2005/0272652 | A1 | 12/2005 | Gault et al. |
| 2005/0277590 | A1 | 12/2005 | O'Harte et al. |
| 2008/0009603 | A1 | 1/2008 | Gault et al. |
| 2008/0161244 | A1 | 7/2008 | O'Harte et al. |
| 2009/0170762 | A1 | 7/2009 | Flatt et al. |
| 2009/0286722 | A1 | 11/2009 | Flatt et al. |

FOREIGN PATENT DOCUMENTS

| | | | |
|---|---|---|---|
| DE | 196 16 486 | A1 | 10/1997 |
| DE | 199 21 537 | A1 * | 11/2000 |
| EP | 0479210 | | 4/1992 |
| EP | 0658568 | | 6/1995 |
| EP | 0708179 | | 4/1996 |
| EP | 0733644 | | 9/1996 |
| EP | 0 869 135 | A1 | 10/1998 |
| EP | 0869135 | | 10/1998 |
| EP | 19616486 | | 10/1998 |
| EP | 0851763 | | 10/2002 |
| EP | 1283058 | | 2/2003 |
| EP | 1171465 | | 8/2004 |
| WO | 91/11457 | | 8/1991 |
| WO | 92/10576 | | 6/1992 |
| WO | 95/19785 | | 7/1995 |
| WO | 96/05309 | | 2/1996 |
| WO | 96/22308 | | 7/1996 |
| WO | 96/40196 | | 12/1996 |
| WO | 97/02004 | | 1/1997 |
| WO | 97/15322 | | 5/1997 |
| WO | 97/27286 | | 7/1997 |
| WO | 97/29180 | | 8/1997 |
| WO | 97/31621 | | 9/1997 |
| WO | 98/05351 | | 2/1998 |
| WO | 98/12224 | | 3/1998 |
| WO | 98/18486 | | 5/1998 |
| WO | 98/30231 | | 7/1998 |
| WO | 98/36763 | | 8/1998 |
| WO | 98/40477 | | 9/1998 |
| WO | 98/48831 | | 11/1998 |
| WO | 98/55139 | | 12/1998 |
| WO | 99/07404 | | 2/1999 |
| WO | 99/25727 | | 5/1999 |
| WO | 99/25728 | | 5/1999 |
| WO | 00/58360 | | 3/2000 |
| WO | 00/20592 | | 4/2000 |
| WO | WO 00/58360 | A2 * | 10/2000 |
| WO | 01/81919 | | 11/2001 |
| WO | 01/87341 | | 11/2001 |
| WO | 02/10195 | | 2/2002 |
| WO | 03/011892 | | 2/2003 |
| WO | 03/022304 | | 3/2003 |
| WO | 03/026591 | | 4/2003 |
| WO | 03/057235 | | 7/2003 |
| WO | 03/082898 | | 10/2003 |
| WO | 03/103572 | | 12/2003 |
| WO | 03/103697 | | 12/2003 |
| WO | 03/105760 | | 12/2003 |
| WO | 2004/037195 | | 5/2004 |
| WO | 2004/067548 | | 8/2004 |
| WO | 2004/078777 | | 9/2004 |
| WO | 2004/103390 | | 12/2004 |
| WO | 2005/077072 | | 8/2005 |
| WO | 2007/018619 | | 2/2007 |

OTHER PUBLICATIONS

O'Harte et al. NH2-Terminally Modified Gastric Inhibitory Polypeptide . . . Diabetes. Apr. 1999, vol. 48, pp. 758-765.*

Demuth, et al., *Chemical Abstracts* 127:69 abstract 341803D (1997).

Fujii et al., *Chem. Pharm. Bull.* 34(6):2397-2410 (1986) "Studies on Peptides. CXXXIX. Solution synthesis of a 42-residue peptide corresponding to the entire amino acid sequence of human glucose-dependent insulinotropic polypeptide (GIP)".

Gallwitz et al., *J Mol. Endocrinology* 10:259-268 (1993) "Binding specificity and signal transduction of receptors for glucagon-like peptide-1(7-36)amide and gastric inhibitory polypeptide on RINm5F insulinoma cells".

Gallwitz et al., *Regulatory Peptides* 63:17-22 (1996) "GLP-1/GIP chimeric peptides define the structural requirements for specific ligand-receptor interaction of GLP-1".

Gault et al., *Digestion* 60:504-505 (1999) "Stability of GIP and Amino-Terminally Modified GIP Analogues to DPP IV and Human Plasma," Scientific Meeting of the Bayliss & Starling Society, Belfast, N. Ireland, Sep. 5-8, 1999.

Gelling et al., "Minor N-terminal modification of glucose-dependent insulinotropic polypeptide (GIP) greatly reduces receptor binding and insulinotropic activity: evidence that N-terminal residues are essential for biological activity," Abstract P2-29, Tenth International Congress of Endocrinology, Jun. 12-13, 1996, San Francisco, USA.

Gelling et al., Endocrinology 138:2640-2643 (1997) "Localization of the domains involved in ligand binding and activation of the glucose-dependent insulin tropic polypeptide receptor".

Gelling et al., *Regulatory Peptides* 69:151-154 (1997) "$GIP_{6-30amide}$ contains the high affinity binding region of GIP and is a potent inhibitor of $GIP_{1.42}$ action in vitro".

Gelling, Ph.D. Thesis, Oct. 1998, "Structure-function studies of the gastric inhibitory polypeptide/glucose dependent insulinotropic polypeptide (GIP) receptor".

Jornvall et al., *FEBS Letters* 123:205-210 (1981) "Amino acid sequence and heterogeneity of gastric inhibitory polypeptide (GIP)".

Kühn-Wache et al., "Analogs of glucose-dependent insulinotropic polypeptide with increased dipeptidyl peptidase IV resistance," in Cellular Peptidases in Immune Functions and Diseases 2, Proceedings of an international conference. Sep. 12-14, 1999, Magdeburg-Herrenkrug, Germany, ed. Langer & Ansorge, Kluwer Academic/Plenum Publishers, 2000.

Kurtzhals et al., *Biochem. J.* 312:725-731 (1995) "Albumin binding of insulins acylated with fatty acids: characterization of the ligand-protein interaction and correlation between binding affinity and timing of the insulin effect in vivo".

McIntosh et al., *Acta Physiol. Scand.* 157:361-365 (1996) "GIP receptors and signal-transduction mechanisms".

Mentlein, *FEBS Letters* 234:251-256 (1988) "Proline residues in the maturation and degradation of peptide hormones and neuropeptides".

Mentlein et al., *Eur. J. Biochem.* 214:829-835 (1993) "Dipeptidyl-peptidase IV hydrolyses gastric inhibitory polypeptide, glucagon-like peptide-1(7-36)amide, peptide histidine methionine and is responsible for their degradation in human serum".

Mooney et al., *Digestion* 60:505 (1999) "Effect of $Tyr^1$-Glucitol GIP on Insulin Release and Glucose Homeostasis in Obese Diabetic Mice," Scientific Meeting of the Bayliss & Starling Society, Belfast, N. Ireland, Sep. 5-8, 1999.

O'Harte et al.,*Biochim. Biophys. Acta.* 1425:319-327 (1998) "Amino terminal glycation of gastric inhibitory polypeptide enhances its insulinotropic action on clonal pancreatic B-cells".

O'Harte et al., *Chemical Abstracts* 131:122 (1999) "$NH_2$—terminally modified gastric inhibitory polypeptide exhibits aminopeptidase resistance and enhanced anti-hyperglycemic activity".

O'Harte et al., *Diabetes* 48:758-765 (1999) "NH$_2$-terminally modified gastric inhibitory polypeptide exhibits aminopeptidase resistance and enhanced anti-hyperglycemic activity".

O'Harte et al., *J. Endocrinology* 165:639-648 (2000) "Improved glycaemic control in obese diabetic ob/ob mice using N-terminally modified gastric inhibitory polypeptide."

Rossowski et al., *Regulatory Peptides* 39:9-17 (1992) "Reduced gastric acid inhibitory effect of a pGIP(1-30)NH$_2$ fragment with potent pancreatic amylase inhibitory activity".

Schmidt et al., *Endocrinology* 120:835-837 (1987) "Commercially available preparations of porcine glucose-dependent insulinotropic polypeptide (GIP) contain a biologically inactive GIP-fragment and cholecystokinin-33/-39".

Al-Sabah et al., (2003), "A model for receptor-peptide binding at the glucagons-like peptide-1 (GLP-1) receptor through the analysis of truncated ligands and receptors," *British Journal of Pharmacology*, 140:339-346.

Andersen et al., (2002), "Medium-Dependence of the Secondary Structure of Exendin-4 and Glucagon-like-peptide-1," *Bioorganic & Medicinal Chemistry*, 10:79-85.

Conlon et al., (1998), "Purification and Characterization of Insulin, Glucagon, and Two Glucagon-Like Peptides with Insulin-Releasing Activity from the Pancreas of the Toad, *Bufo marinus*," *Endocrinology*, 139:3442-3448.

Delmeire et al., (2004), "Prior in vitro exposure to GLP-1 with or without GIP can influence the subsequent beta cell responsiveness," *Biochemical Pharmacology*, 68:33-39.

Demuth et al., (1997), "Method for lowering the blood glucose level in mammls," *Chemical Abstracts*, 1-Pharmacology, 127(25):69.

Doyle et al., (2001), "Insertion of a N-terminal 6-Aminohexanoic Acid after the 7 amino acid position of glucagons-like peptide-1 produces a long-acting hypoglycemic agent," *Endocrinology*, 142(10):4462-4468.

Doyle et al., (2003), "The importance of the nine-amino acid C-terminal sequence of exendin-4 for binding to the GLP-1 receptor and for biological activity," *Regulatory Peptides*, 114:153-158.

Elahi et al., (1994), "The insulinotropic actions of glucose-dependent insulintropic polypeptide (GIP) and glucagons-like peptide-1 (7-37) in normal and diabetic subjects," *Regulatory Peptides*, 51:63-74.

Eng, (1996), "Prolonged Effect of Exendin-4 on Hyperglycemia of db/b mice," *Diabetes*, 45:152A, Abstract 554.

Fehman et al., (1995), "Cell and Molecular Biology of teh Incretin Hormones Glucagon-Like Peptide-1 adn Glucose-Dependent Insulin Releaseing Polypeptide," *Endocrine Reviews*, 16(3):390-410.

Furman et al, (2004), "Targeting beta cell cyclic 3'5' adenosine monophosphate for the development of novel drugs for treating type 2 diabetes mellitus. A review." *Journal of Pharmacy and Pharmacology*, 56:1477-1492.

Gallwitz, B., (1993, "Binding specificity and signal transduction of receptors for glucagon-like peptide-1 (7-36)amide and gastric inhibitory polypeptide on RINm5F insulinoma cells," *Journal of Molecular Endocrinology*, 10:259-268.

Gallwitz, B.,(1996), "GLP-1/GIP chimeric peptides define the structural requirements for specific ligand-receptor interaction of GLP-1," *Regulatory Peptides*, 63:17-22.

Gault, V.A., (1999), "Stability of GIP and amino-terminally modified GIP analogues to DPP IV and human plasma," *Digestion*, 60:504-505.

Gault, V.A., (2003), "Improved Biological activity of Gly1- and Ser2- substituted analogues of glucose-dependent insulinotrophic polypeptides," *Journal of Endocrinology*, 176:133-141.

Gault, V.A., (2003), "DPP IV resistance and insulin releasing activity of a novel di-substituted analogue of glucose-dependent insulinotropic polypeptide, (Ser2-Asp13)GIP," *Cell Biology International*, 27:41-46.

Gault, V.A., (2003), "Defradation cylci adenosine monophosphate production, insulin secretion, and glycemic effects of two novel N-terminal Ala2-substituted analogs of glucose-dependent insulintropic polypeptide with preserved biological activity in vivo," *Metabolism*, 52(6):679-687.

Gault, V.A., (2007), "Characterisation and glucoregulatory actions of a novel acylated form of the (Pro3)GIP receptor antagonist in type 2 diabetes," *Biological Chemistry*, 388:173-179.

Gault, V.A., (2003), "Glucose-dependent insulinotropic polypeptide (GIP): anti-diabetic and anti-obesity potential?" *Neuropeptides*, 37:53-263.

Gault, V.A., (2003), "Glucose-dependent insulinotropic polypeptide analogues and their therapeutic potential for the treatment of obesity-diabetes," *Biochemical and Biophysical research Communications*, 308:207-213.

Green, B.D., (2004), "Comparative effects of GLP-1 and GIP and cAMP production, insulin secretion, and in vivo antidiabetic actions following substitution of Ala8/Ala2 with 2-aminobutyric acid," *Archives of Biochemistry and Biophysics*, 428:136-143.

Hinke, S.A., (2002), "Dipeptidyl peptidase IV-resistant [D-Ala2] glucose-dependent insulinotropic polypeptide (GIP) improves glucose tolerance in normal and obese diabetic rats," *Diabetes*, 51:652-661.

Hinke, A.S., (2003), "Structure-activity relationships of glucose-dependent insulintropic polypeptide (GIP)," *Biol. Chem.*, 384:403-407.

Hinke, S.A., (2004), "[Ser2]- and [Ser(P)2] Incretin Analogs: Comparison of dipeptidyl peptidase IV resistance and biological activities in vitro and in vivo," *J. Biol. Chem.*, 279(6):3998-4006.

Hinke, S.A., (2004), "In depth analysis of the N-terminal bioactive domain of gastric inhibitory polypeptide," *Life Sciences*, 75:1857-1870.

Holst, J.J., (1997), "The pathogenesis of NIDDM involves a defective expression of the GIP receptor," Diabetologia, 40:984-986.

Hudson, F.M., (2004), "Exenatide: NMR/CD evaluation of the medium dependence of conformation and aggregation state" *Biopolymers (Pept. Sci.)*, 76:98-308.

Hupe-Sodmann, K., (1995), "Characterisation of the processing by human neutral endopeptidase 24.11 of GLP-1(7-36) amide and comparison of the substrate specificity of the enzyme for other glucagon-like peptides," *Regulatory Peptides*, 58:149-156.

Irwin, N., (2005), "Degradation, insulin secretion, and antihyperglycemic actions of two palmitate-derivitized N-terminal pyroglutamyl analogues of glucose-dependent insulinotropic polypeptide," *J. Med. Chem.*, 48:1244-1250.

Kieffer, T.J., (1995), "Degradation of glucose-dependent insulintropic polypeptide and truncated glucagon-like peptide 1 in vitro adn in vivo dipeptidyl peptidase IV," *Endiocrinology*, 136(8):3585-3596.

Kuhn-Wache, K., (2000), "Analogs of glucose-dependent insulintropic polypeptide with increased dipeptidyl peptidase IV resistance," *Cellular Peptidases in Immune Function adn Diseases 2*, Edited by Langner and Ansorge, Kluwet Academic/Plenum Publishers, pp. 187-195.

Lin, J.C., (2004), "The helical alanine controversy: An (Ala)6 insertion dramatically increases helicity," *J. Am. Chem. Soc.*, 126:13679-13684.

Manhart, S., (2003), "Structure-function analysis of a series of novel GIP analogues containing different helical length linkers," *Biochemistry*, 42:3081-3088.

Meier, J.J., (2004), "Glucose-dependent insulintropic polypeptide/gastric inhibitory polypeptide," *Best Practice & Research Clinical Endocrinology & Metabolism*, 18(4):587-606.

Mier, J.J., (2004), "Stimulation of insulin secretion by intravenous bolus injection and continuous infusion of gastric inhibitory polypeptide in patients with type 2 diabetes and healthy control subjects," *Diabetes*, 53(Suppl. 3):S220-S224.

Montrose-Rafizadeh, C., (1997), "High potency antagonists of the pancreatic glucagon-like peptide-1 receptor," *J. Biol. Chem.*, 272:21201-21206.

Morrow, G.W., (1996), "The insulinotropic region of gastric inhibitory polypeptide; fragment analysis suggests the bioactive site lies between residues 19 and 30," *Can. J. Physiol. Pharmacol.*, 74:65-72.

Nauck, M.A., (1993), "Preserved incretin activity of glucagon-like peptide 1 [7-36 amide] but not of synthetic human gastric inhibitory polopeptide in patients with type-2 diabetes mellitus," *J. Clin. Invest.*, 91:301-307.

Neidigh, J.W., (2001), "Exendin-4 and glucagon-like-peptide-1: NMR structural comparisons in the solution and micelle-associated states," *Biochemistry*, 40:13188-13200.

O'Harte, F.P.M., (1997), "Effects of non-glycated and glycated glucagon-like peptide-1(7-36) amide on glucose metabolism in isolated mouse abdominal muscle," *Peptides*, 18:1327-1333.

O'Harte, F.P.M., (1998), "Glycation of glucagon-like peptide-1(7-36) amide: characterization and impaired action on rat insulin secreting cells," *Diabetologia*, 41:1187-1193.

O'Harte, F.P.M., (1998), "Amino terminal glycation of gastric inhibitory polypeptide enhances its insulintropic action on clonal pancreatic B-cells," *Biochimica et Biophysica Acta*, 1425:319-327.

O'Harte, F.P.M., (1999), "NH2-Terminally modified gastric inhibitory polypeptide exhibits amino-peptidase resistance and enhanced antihyperglycemic activity," *Diabetes*, 48:758-765.

O'Harte, F.P.M., (2001), "Degradation and glycemic effects of His7-glucitol glucagon-like peptide-1(7-36)amide in obese diabetic ob/ob mice," *Regulatory Peptides*, 96:95-104.

Pauly, R.P., (1996), "Investigation of glucose-dependent insulintropic polypeptide-(1-42) and glucagon-like peptide-1-(7-36) degradation in vitro by dipeptidyl peptidase IV using matrix-assisted laser desorption/ionization-time of flight mass spectrometry: A novel kinetic approach," *J. Biol. Chem.*, 271(38):23222-23229.

Pederson, R.A., (1996), "The enteroinsular axis in dipeptidyl peptidase IV-negative rats," Metabolism, 45(11):1335-1341.

Plamboeck, A., (2003), "Neutral endopeptidase 24.11 and dipeptidyl peptidase IV are both involved in regulating the metabolic stability of glucagon-like peptide-1 in vivo," Dipeptidyl Aminopeptidases in Health and Disease, Edited by Hildebrandt et al., Kluwer Academic/Plenum Publishers, pp. 303-312.

Siegel, E.G., (1999), "Comparison of the effect of native glucagon-like peptide I and dipeptidyl peptidase IV-resistant analogues on insulin release from rat pancreatic islets," *European Journal of Clinical Investigation*, 29:610-614.

Thum, A., (2002), "Endoproteolysis by isolated membrane peptidases reveal metabolic stability of glucagon-like peptide-1 analogs, exendins-3 and -4," *Exp. Clin. Endocrinol. Diabetes*, 110:113-118, 2002.

Wheller et al., (1995), "Functional Expression of the Rat Pancreatic Islet Glucose-Dependent Insulinotropic Polypeptide Receptor: Ligand Binding and Intracellular Signaling Properties," *Endocrinology*, 136(10):4629-4639.

Chang et al., (2003), "Aging and Insulin Secretion," *Am. J. Physical Endocrinol. Metad.*, 284:E7-E12.

Conlon et al., (1987), "Primary Structure of Glucagon from the Gut of the Common Dogfish," *FEBS Letters*, 213:50-56.

Gault et al., (2005), "Chemical Ablation of Gastric Inhibitory Polypeptide Receptor Action by Daily (Pro[3])GIP Administration Improves Glucose Tolerance and Ameliorates Insulin Resistance and Abnormalities of Islet Structure in Obesity Related Diabetes," *Diabetes*, 54:2436-2446.

Irwin et al., (2005), "A Novel, Long-Acting Agonist of Glucose-Dependent Insulinotropic Polypeptide Suitable for Once-Daily Administration in Type 2 Diabetes," *J. Pharmaco. Exp. Thera.*, 314:1187-1194.

Irwin et al., (2005), "Antidiabetic Potential of Two Novel Fatty Acid Derivatised, N-Terminally Modified Analogues of Glucose-Dependent Insulinotropic Polypeptide (GIP):N-AcGIP(LysPAL[16]) and N-AcGIP(LysPAL[37])," *Biol. Chem.*, 386:679-687.

Agersø et al., (2002), "The pharmacokinetics, pharmacodynamics, safety and tolerability of NN2211, a new long-acting GLP-1 derivative, in healthy men," *Diabetologia*, 45: 195-202.

Anini et al., (2003), "Role of leptin in the regulation of glucagon-like peptide-1 secretion," *Diabetes*, 52:252-259.

Bailey et al., (1982), "Influence of genetic background and age on the expression of the obese hyperglycaemic syndrome in Aston ob/ob mice," Int. J. Obesity, 6:11-21.

Bailey et al., (2003), "Animal syndromes resembling type 2 diabetes," in Textbook of Diabetes, 3rd ed. Pickup J.C. & Williams G., eds. Oxford, Blackwell Science Ltd., pp. 25.1-25.30.

Bailey et al., (1986), "Immunoreactive gastric inhibitory polypeptide and K cell hyperplasia in obese hyperglycaemic (ob/ob) mice fed high fat and high carbohydrate cafeteria diets," *Acta Endocrinol.*, 112:224-229.

Drucker et al., (2003), "Enhancing incretin action for the treatment of type 2 diabetes," *Diabetes Care*, 10:2929-2940.

Ehses et al., (2003), "Glucose-dependent insulinotropic polypeptide promotes beta-(INS-1) cell survival via cyclic adenosine monophosphate-mediated caspase-3 inhibition and regulation of p38 mitogen-activated protein kinase," *Endocrinology*, 144:4433-4445.

Flamez et al., (1998), "Mouse pancreatic beta-cells exhibit preserved glucose competence after disruption of the glucagon-like peptide-1 receptor gene," *Diabetes*, 47: 646-652.

Flatt et al., (1983), "Abnormalities of GIP in spontaneous syndromes of obesity and diabetes in mice," *Diabetes*, 32: 433-435.

Flatt et al., (1984), "Plasma immunoreactive gastric inhibitory polypeptide in obese hyperglycaemic (ob/ob) mice," *J. Endocrinol.*, 101: 249-256.

Flatt et al., (1981), "Development of glucose intolerance and impaired plasma insulin response to glucose in obese hyperglycaemic (ob/ob) mice," *Horm. Metab. Res.*, 13:556-560.

Flatt et al., (1992), "Defective insulin secretion in diabetes and insulinoma," in Nutrient Regulation of Insulin Secretion, Flatt P.R., ed. London, Portland Press, p. 341-386.

Flatt et al., (1981), "Abnormal plasma glucose and insulin responses in heterozygous lean (ob/+) mice," *Diabetologia*, 20:573-577.

Gault et al., (2002), "Characterization of the cellular and metabolic effects of a novel enzyme-resistant antagonist of glucose-dependent insulinotropic polypeptide," *Biochem. Biophys. Res. Commun.*, 290:1420-1426.

Gault et al., (2002), "Enhanced cAMP generation and insulin-releasing potency of two novel Tyr1-modified enzyme-resistant forms of glucose-dependent insulinotropic polypeptide is associated with significant antihyperglycaemic activity in spontaneous obesity-diabetes," *Biochem. J.*, 367: 913-920.

Gault et al., (2002), "Cyclic AMP production and insulin releasing activity of synthetic fragment peptides of glucose-dependent insulinotropic polypeptide," *Biosci. Rep.*, 22: 523-528.

Gault et al., (2002), "DPP IV resistance and insulin releasing activity of novel di-substituted analogue of glucose-dependant insulinotropic polypetide, (Ser2-Asp13)GIP," *Cell. Biol. Int.*, 27:41-46.

Gault et al., (2003), "Effects of the novel (Pro3)GIP antagonist and exendin(9-39)amide on GIP- and GLP-1-induced cyclic AMP generation, insulin secretion and postprandial insulin release in obese diabetic (ob/ob) mice: evidence that GIP is the major physiological incretin," *Diabetologia*, 46:222-230.

Gault et al., (2003), "Improved biological activity of Gly2- and Ser2-substituted analogues of glucose-dependent insulinotrophic polypeptide," *J. Endocrinol.*, 176:133-141.

Green et al., (2004), "Degradation, receptor binding, insulin secreting and antihyperglycaemic actions of palmitate-derivatised native and Ala8-substituted GLP-1 analogues," *Biol. Chem.*, 385: 169-177.

Green et al., (2004), "Structurally modified analogues of glucagon-like peptide-1 (GLP-1) and glucose-dependent insulinotropic polypeptide (GIP) as future antidiabetic agents," *Curr. Pharm. Des.*, 10(29):3651-62.

Gremlich et al., (1995), "Cloning, functional expression, and chromosomal localization of the human pancreatic islet glucose-dependent insulinotropic polypeptide receptor," *Diabetes*, 44: 1202-1208.

Hansotia et al., (2004), "Double incretin receptor knockout (DIRKO) mice reveal an essential role for the enteroinsular axis in transducing the glucoregulatory actions of DPP-IV inhibitors," *Diabetes*, 53:1326-1335.

Hinke et al., (2001), "Identification of a bioactive domain in the amino-terminus of glucose-dependent insulinotropic polypeptide (GIP)," *Biochim. Biophys. Acta*, 1547:143-55.

Hinke et al., (2002), "Dipeptidyl peptidase IV-resistant [D-Ala(2)]glucose-dependent insulinotropic polypeptide (GIP) improves glucose tolerance in normal and obese diabetic rats," *Diabetes*, 51:652-661.

Holst et al., (2004), "Role of incretin hormones in the regulation of insulin secretion in diabetic and nondiabetic humans," *Am. J. Physiol. Endocrinol. Metab.*, 287:E199-E206.

Holz et al., (1993), "Pancreatic beta-cells are rendered glucose-competent by the insulinotropic hormone glucagon-like peptide-1(7-37)," *Nature*, 361: 362-365.

Holz et al., (2003), "Glucagon-like peptide-1 synthetic analogs: new therapeutic agents for use in the treatment of diabetes mellitus," *Curr. Med. Chem.*, 10:2471-2483.

Irwin, (2004), "Effects of short-term chemical ablation of the GIP receptor on insulin secretion, islet morphology and glucose homeostasis in mice," *Biol. Chem.*, 385:845-852.

Kim et al., (2003), "Development and characterization of a glucagon-like peptide 1-albumin conjugate: the ability to activate the glucagon-like peptide 1 receptor in vivo," Diabetes, 52:751-759.

Kjems et al., (2003), "The influence of GLP-1 on glucose-stimulated insulin secretion: effects on beta-cell sensitivity in type 2 and nondiabetic subjects," *Diabetes*, 52:380-386.

Knudsen et al., (2000), "Potent derivatives of glucagon-like peptide-1 with pharmacokinetic properties suitable for once daily administration," *J. Med. Chem.*, 43:1664-1669.

Marshall et al., (1981), "Characterization of insulin-induced receptor loss and evidence for internalization of the insulin receptor," *Diabetes*, 30: 746-753.

McClenaghan et al., "Characterization of a novel glucose-responsive insulin-secreting cell line, BRIN-BD11, produced by electrofusion," (1996), *Diabetes*, 45:1132-1140.

Meier et al., (2002), "Gastric inhibitory polypeptide: the neglected incretin revisited," Regul. Pept., 107:1-13.

Pederson et al., (1998), "Enhanced glucose-dependent insulinotropic polypeptide secretion and insulinotropic action in glucagon-like peptide 1 receptor -/- mice," *Diabetes*, 47:1046-1052.

Pospisilik et al., (2003), "Dipeptidyl peptidase IV inhibitor treatment stimulates beta-cell survival and islet neogenesis in streptozotocin-induced diabetic rats," *Diabetes*, 52:741-750.

Preitner et al., (2004), "Gluco-incretins control insulin secretion at multiple levels as revealed in mice lacking GLP-1 and GIP receptors," *J. Clin. Invest.*, 113:635-645.

Trumper et al., (2001), "Glucose-dependent insulinotropic polypeptide is a growth factor for beta (INS-1) cells by pleiotropic signaling," *Mol. Endocrinol.*, 15:1559-1570.

Trumper et al., (2002), "Mechanisms of mitogenic and anti-apoptotic signaling by glucose-dependent insulinotropic polypeptide in beta(INS-1)-cells," *J. Endocrinol.*, 174:233-246.

Tseng et al., (1996), "Chronic desensitization of the glucose-dependent insulinotropic polypeptide receptor in diabetic rats," *Am. J. Physiol.*, 270: E661-E666.

Vilsboll et al., (2002), "Defective amplification of the late phase insulin response to glucose by GIP in obese Type II diabetic patients," Diabetologia, 45:1111-1119.

Wang et al., (1996), "GIP regulates glucose transporters, hexokinases, and glucose transporters, hexokinases, and glucose-induced insulin secretion in RIN 1046-38 cells, " *Mol. Cell. Endocrinol.*, 116:81-87.

Wheeler et al., (1995), "Functional expression of the rat pancreatic islet glucose-dependent insulinotropic polypeptide receptor: ligand binding and intracellular signaling properties," *Endocrinology*, 136:4629-4639.

Yip et al., (1998), "Functional GIP receptors are present on adipocytes," *Endocrinology*, 139:4004-4007.

Meier et al., (2004), "Gastric inhibitory polypeptide does not inhibit gastric emptying in humans," *Am. J. Physiol. Endocrinol. Metab.*, 286:E621-625.

Meier et al., (2003), "Similar insulin secretory response to a gastric inhibitory polypeptide bolus injection at euglycemia in first-degree relatives of patients with type 2 diabetes and control subjects," *Metabolism*, 52:1579-1585.

Miyawaki et al., (1999), "Glucose intolerance caused by a defect in the entero-insular axis: a study in gastric inhibitory polypeptide receptor knockout mice," *Proc. Nat. Acad. Sci. USA*, 96:14843-14847.

Miyawaki et al., (2002), "Inhibition of gastric inhibitory polypeptide signaling prevents obesity," *Nat. Med.*, 8:738-742.

Morgan et al., (1996), "The metabolic role of GIP: physiology and pathology," *Biochem. Soc. Trans.*, 24:585-591.

Morgan, L.M., (1992), "Insulin secretion and the enteroinsular axis," In: Nutrient regulation of insulin secretion, Flatt, P.R., ed., London, Portland Press, 1992, p. 1-22.

O'Harte et al., (1998), "Gastric inhibitory polypeptide and effects of glycation on glucose transport and metabolism in isolated mouse abdominal muscle," *J. Endocrinol.*, 156: 237-243.

O'Harte et al., (2002), "Improved stability, insulin-releasing activity and antidiabetic potential of two novel N-terminal analogues of gastric inhibitory polypeptide: N-acetyl-GIP and pGlu-GIP," *Diabetologia*, 45: 1281-1291.

Pamir et al., (2003), "Glucose-dependent insulinotropic polypeptide receptor null mice exhibit compensatory changes in the enteroinsular axis," *Am. J. Physiol. Endocrinol. Metab.*, 284:E931-939.

Brown et al., (1967), "Preparation of highly active enterogastrone," *Can. J. Physiol. Pharmacol.*, 47: 113-114.

Creutzfeld et al., (2001), "The entero-insular axis in type 2 diabetes—incretins as therapeutic agents," *Exp. Clin. Endocrinol. Diabetes*, 109 Suppl 2:S288-S303.

\* cited by examiner

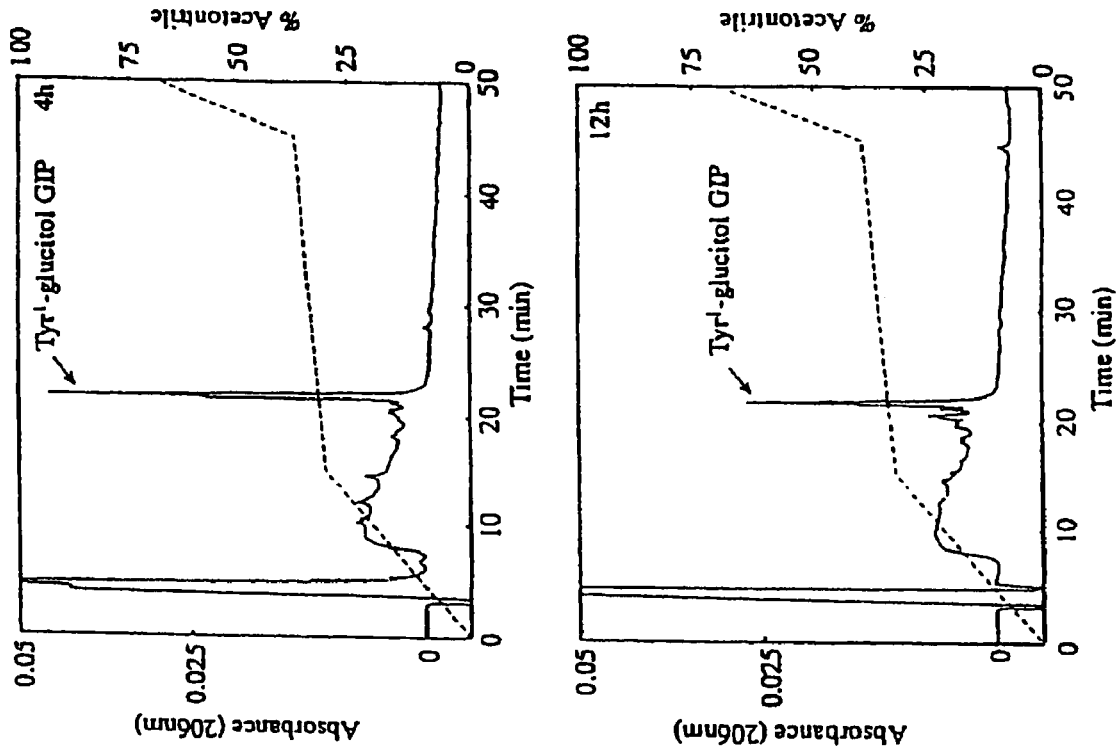
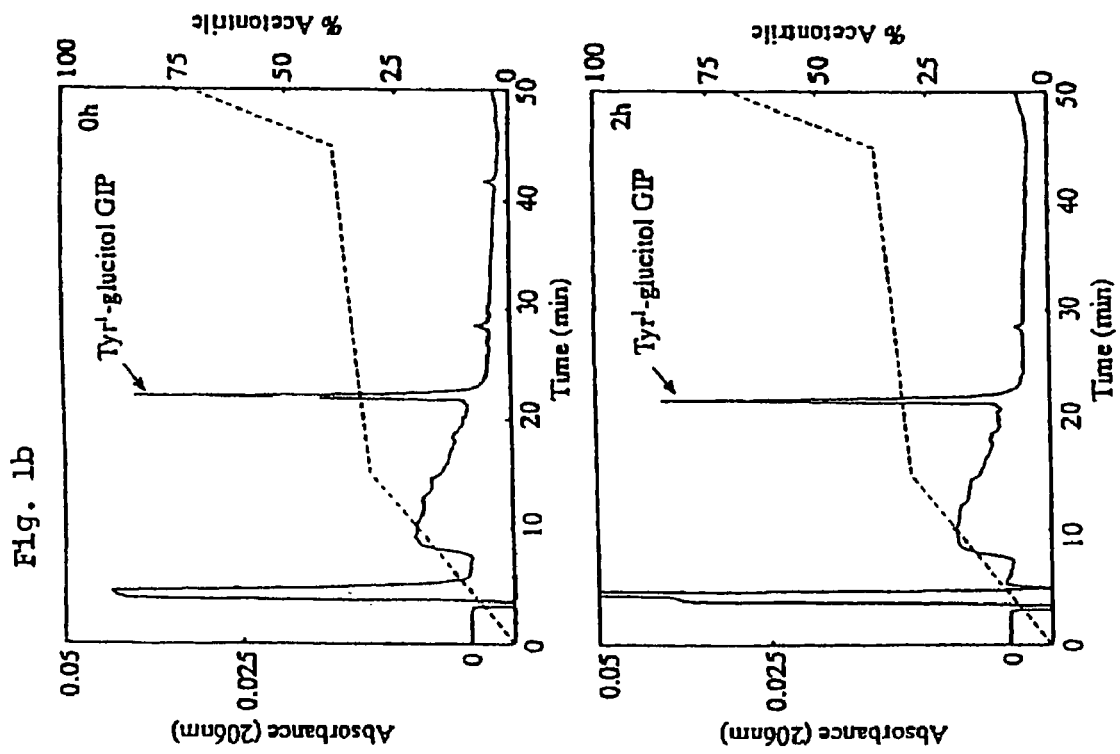
Fig. 1b

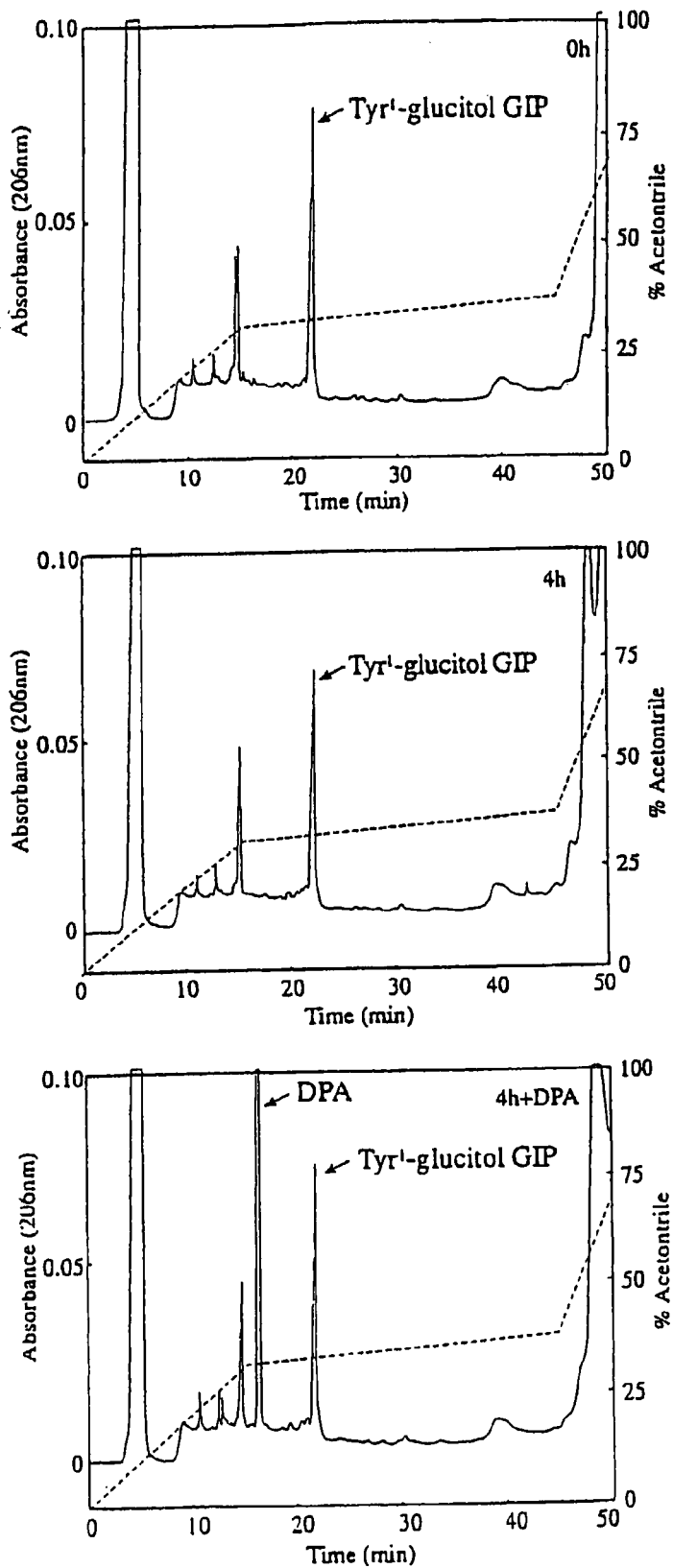

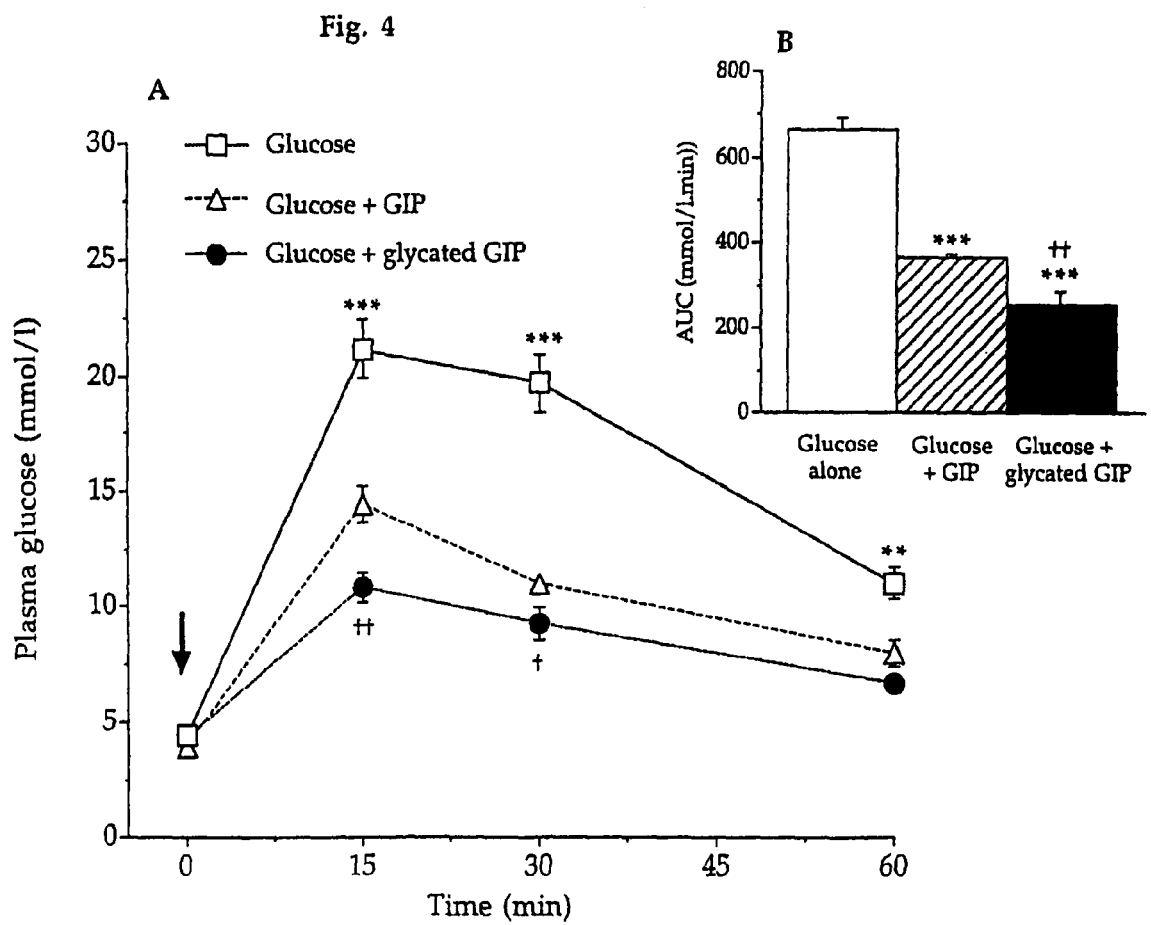

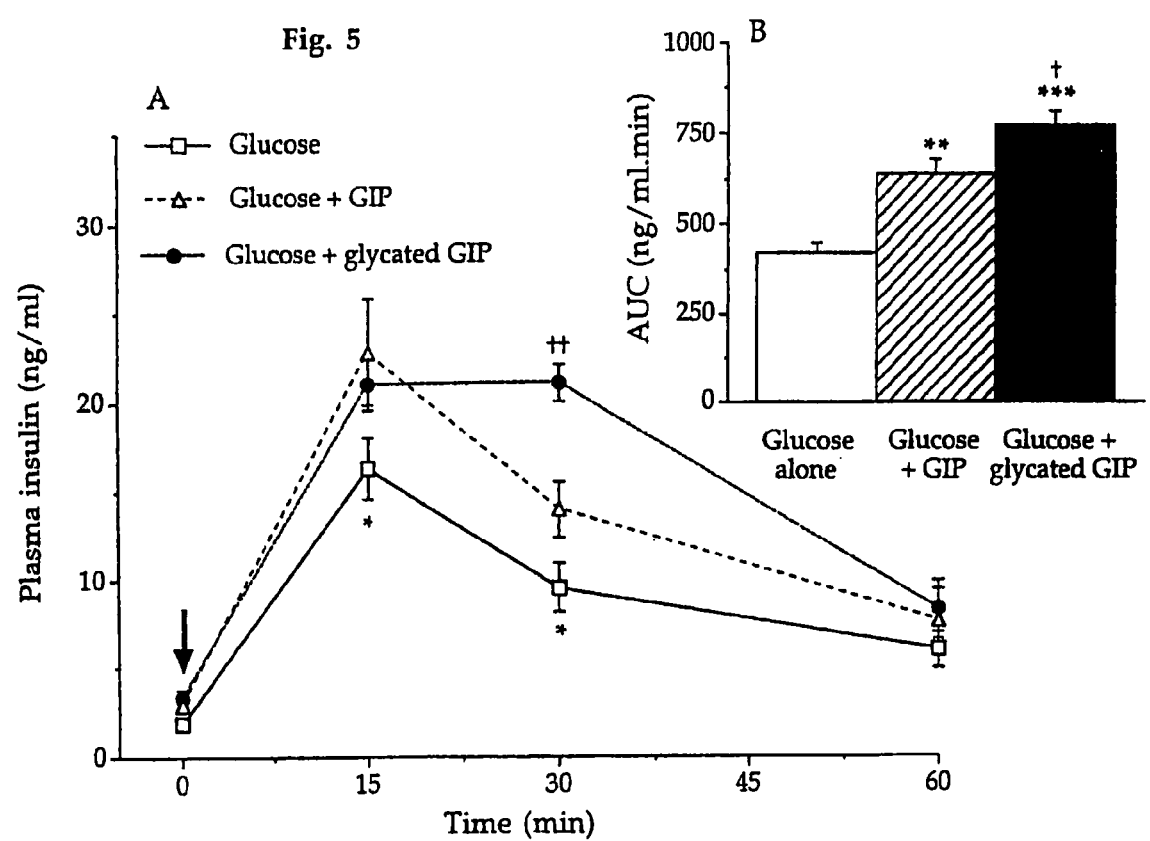

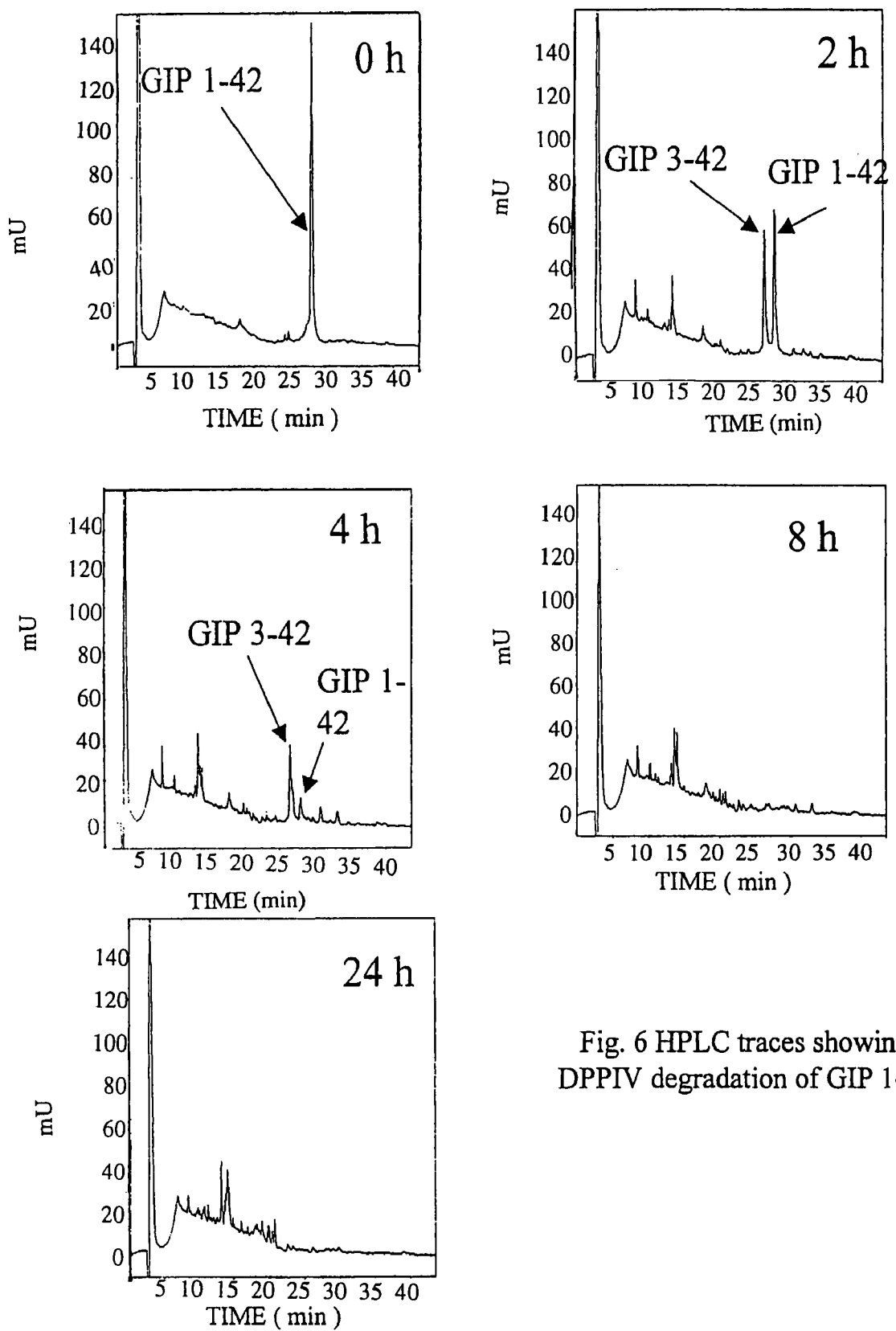
Fig. 6 HPLC traces showing DPPIV degradation of GIP 1-42

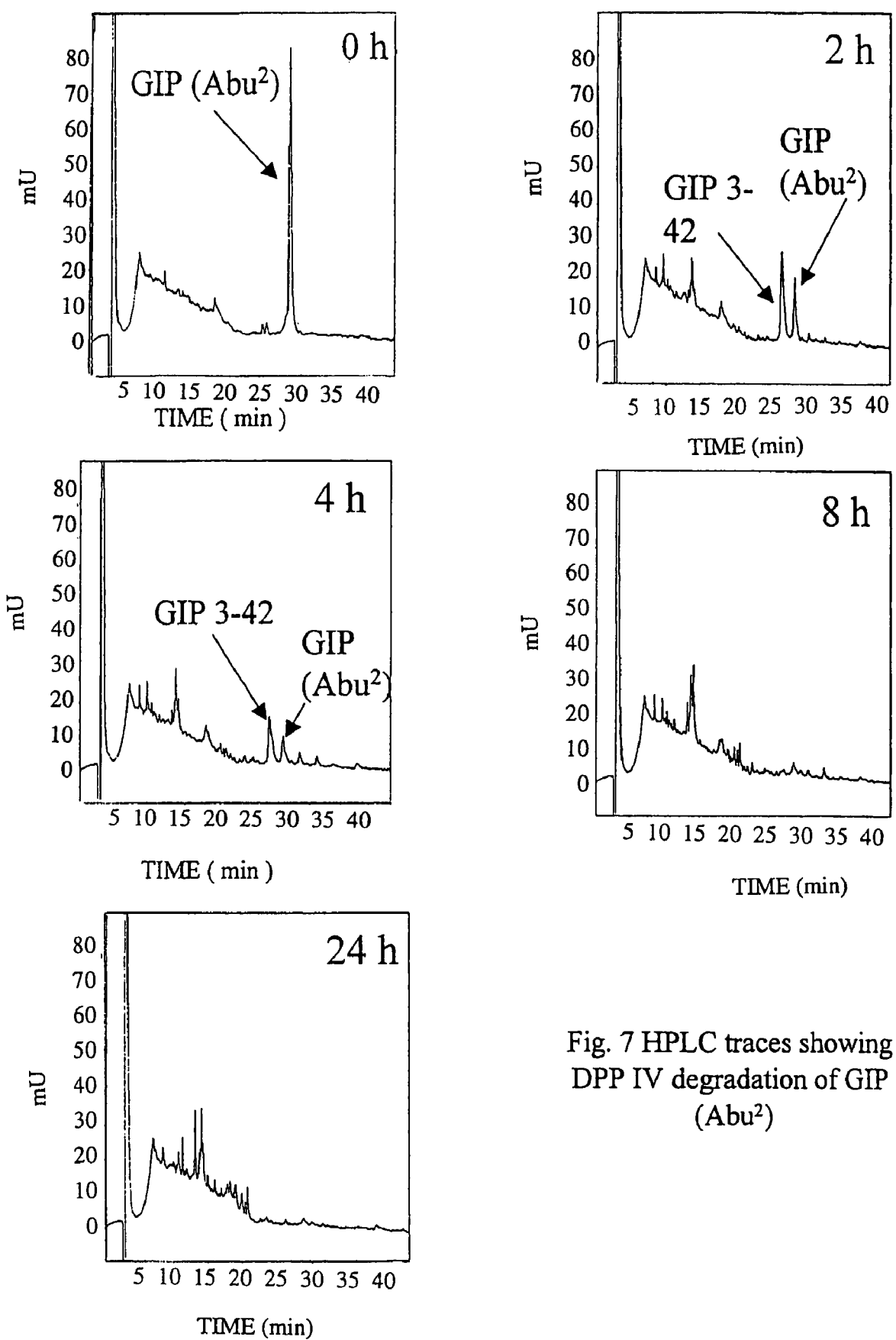
Fig. 7 HPLC traces showing DPP IV degradation of GIP (Abu$^2$)

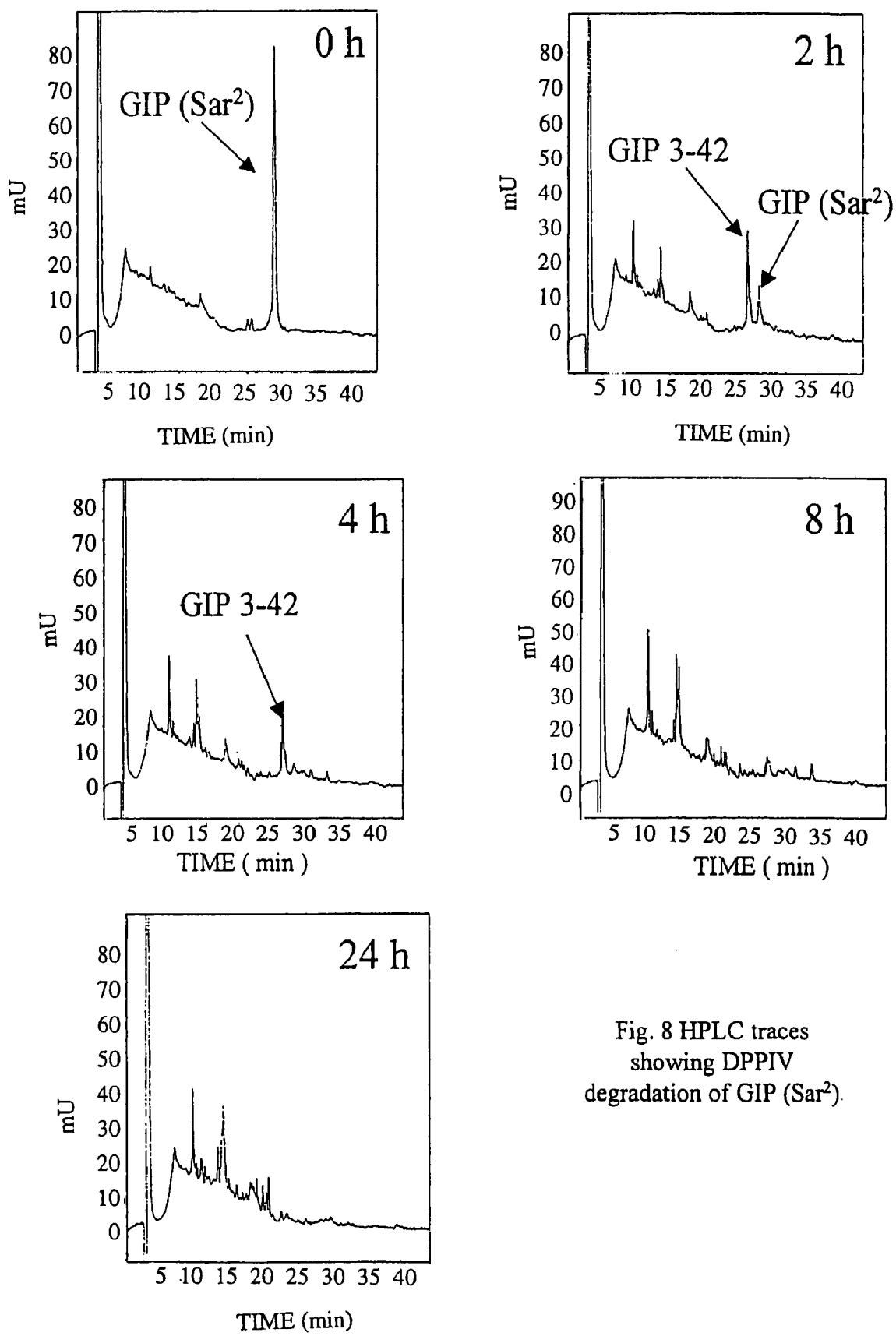
Fig. 8 HPLC traces showing DPPIV degradation of GIP (Sar$^2$)

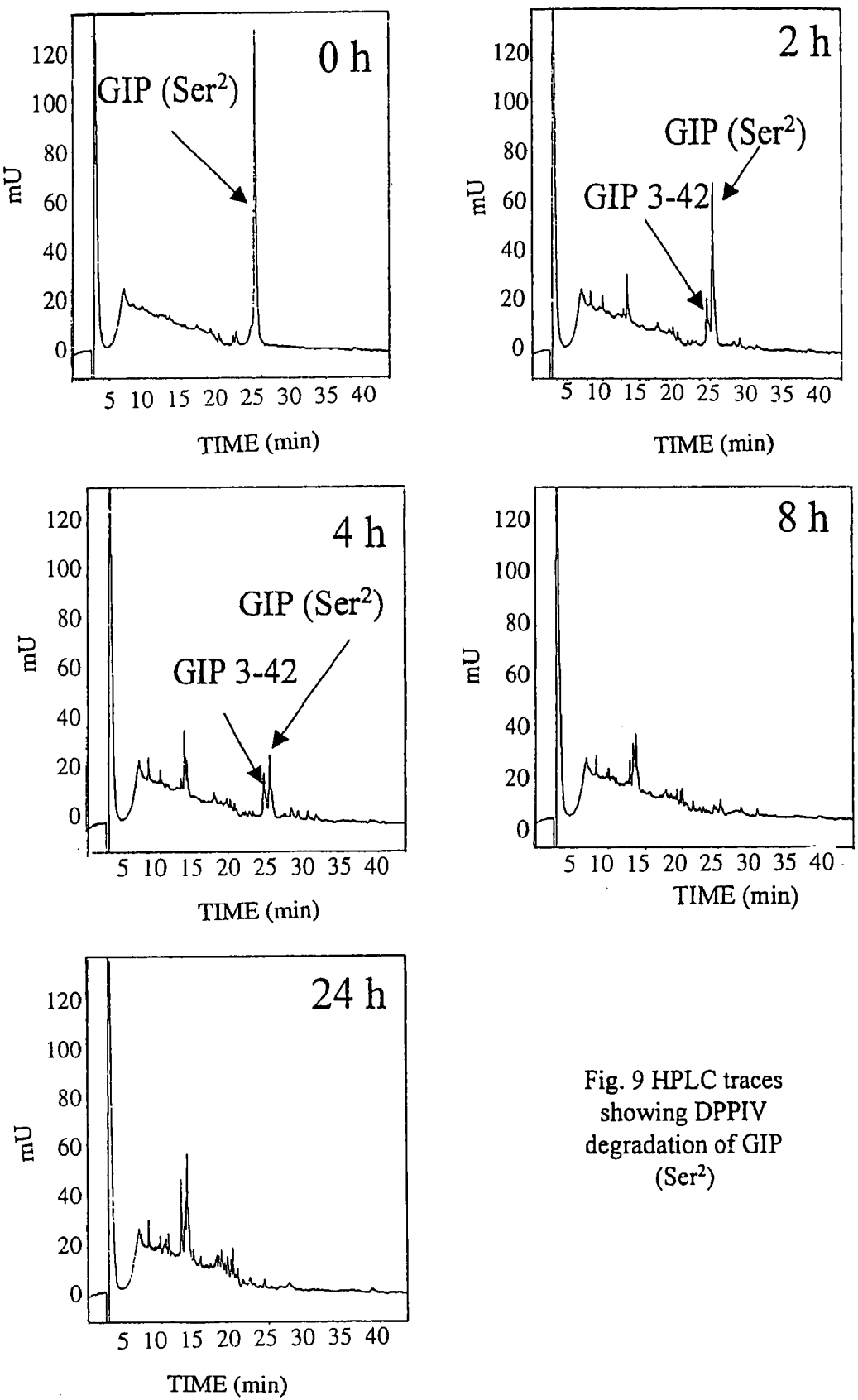
Fig. 9 HPLC traces showing DPPIV degradation of GIP (Ser$^2$)

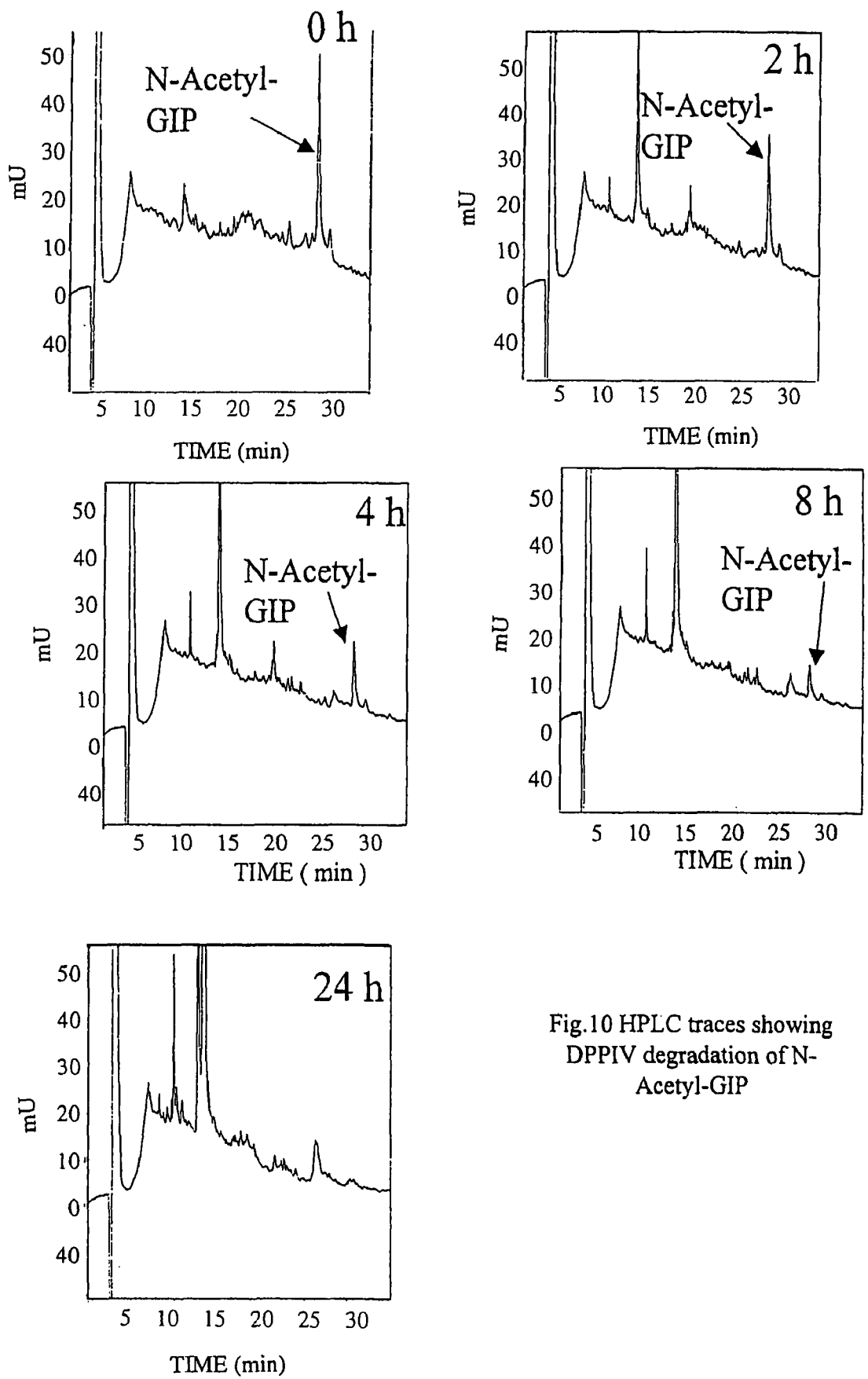
Fig.10 HPLC traces showing DPPIV degradation of N-Acetyl-GIP

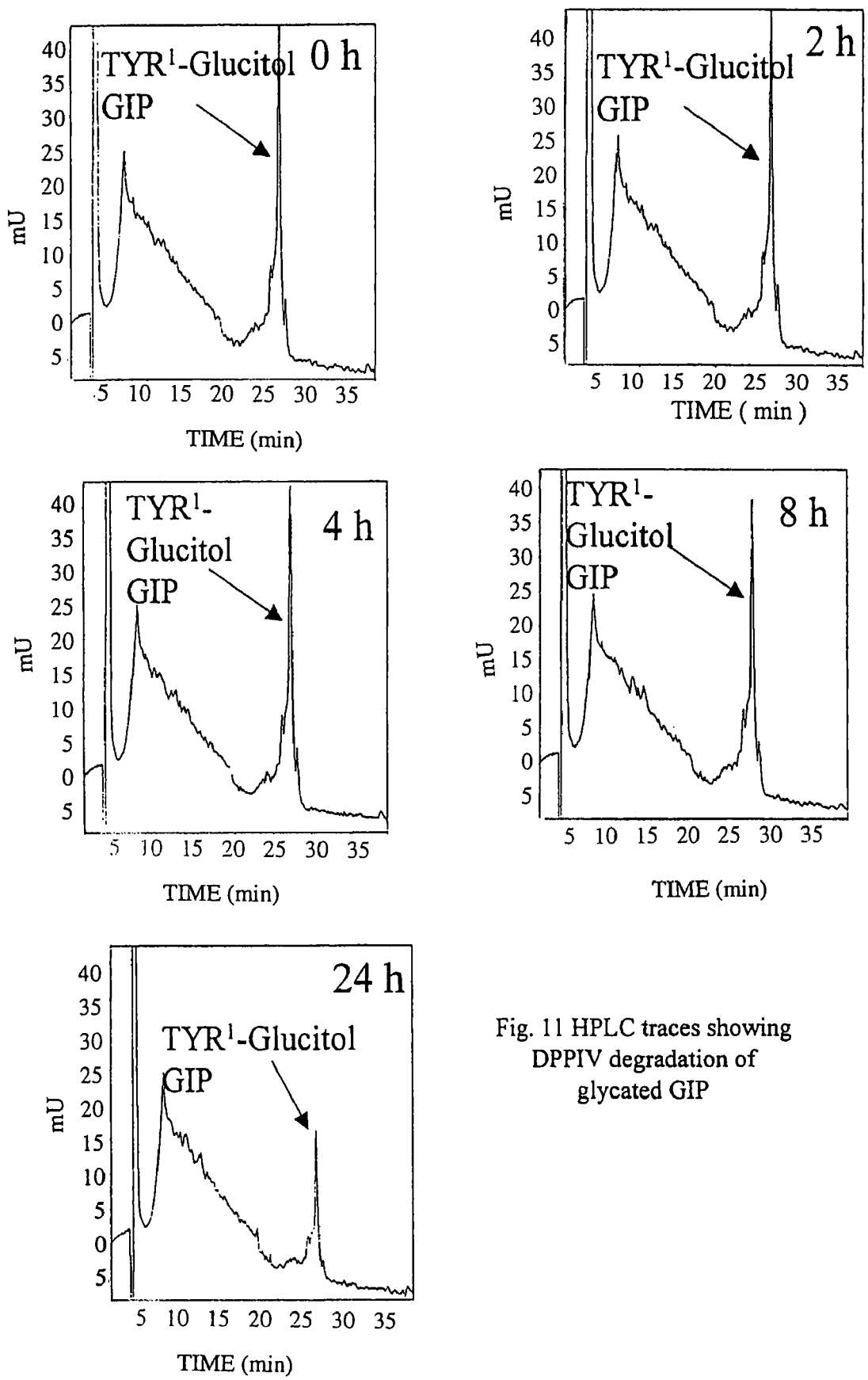
Fig. 11 HPLC traces showing DPPIV degradation of glycated GIP

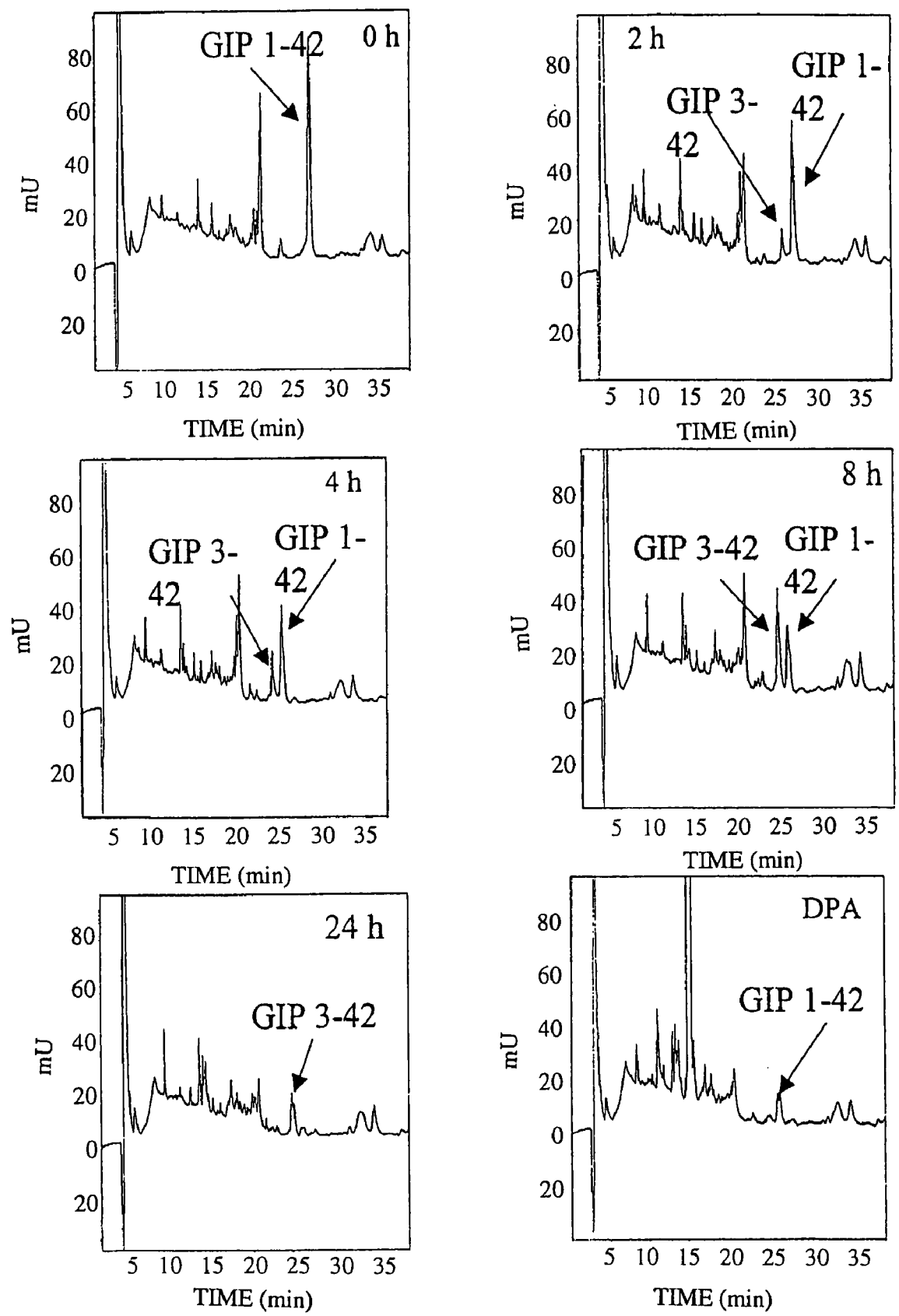
Fig.12. HPLC traces showing human plasma degradation of GIP

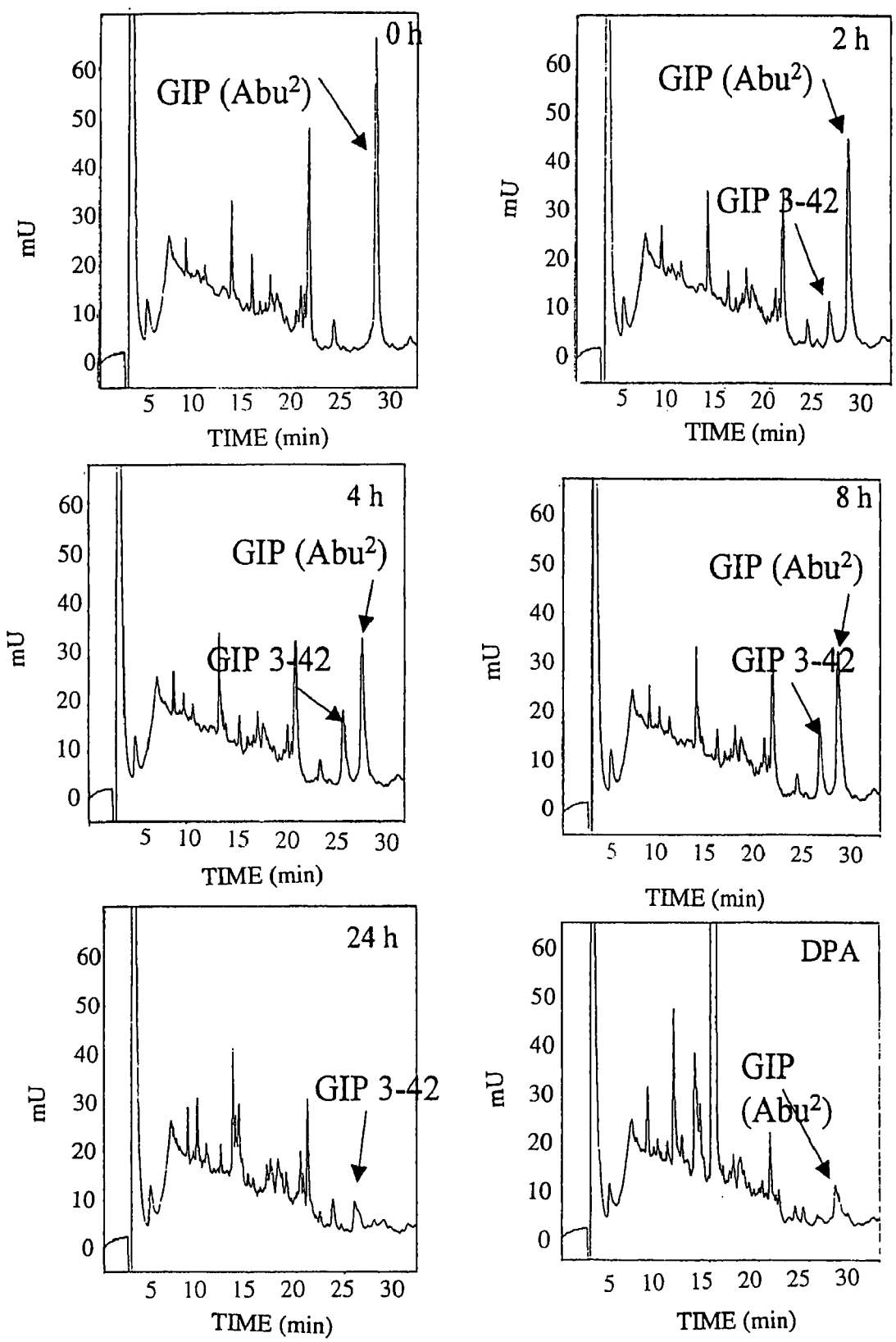
Fig. 13. HPLC traces showing human plasma degradation of GIP (Abu$^2$)

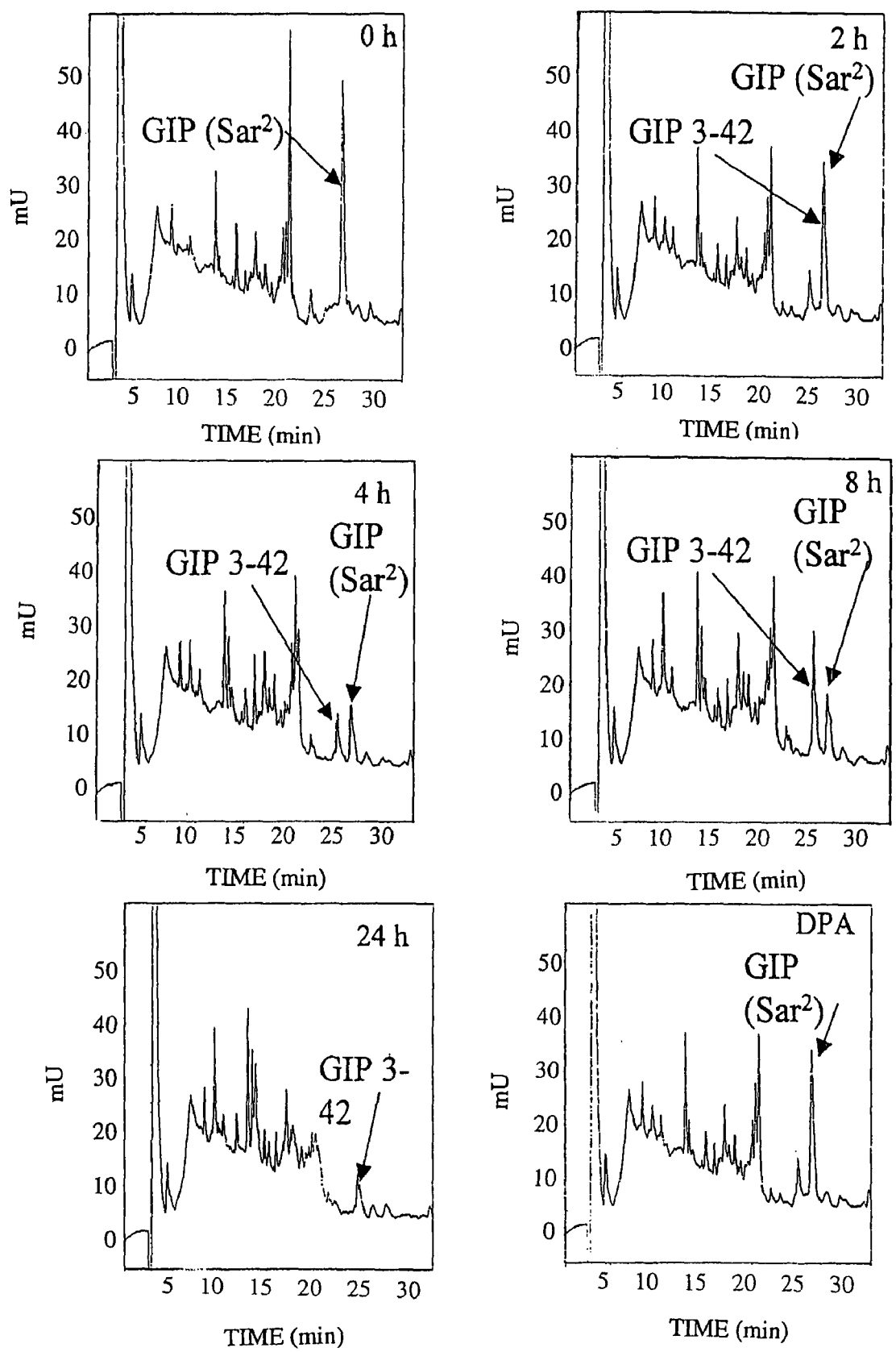
Fig. 14. HPLC traces showing human plasma degradation of GIP (Sar$^2$)

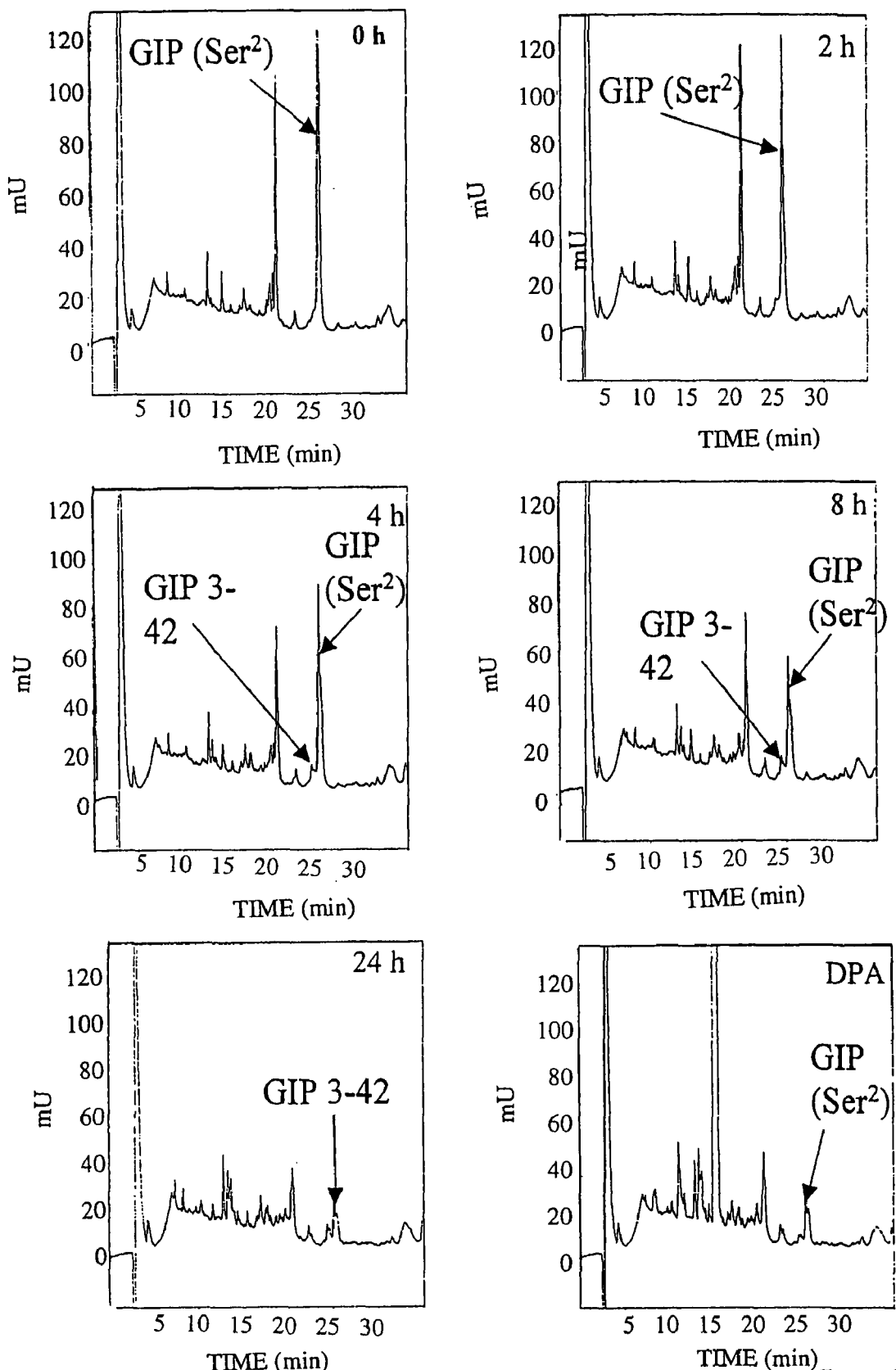
Fig. 15 HPLC traces showing human plasma degradation of GIP(Ser $^2$)

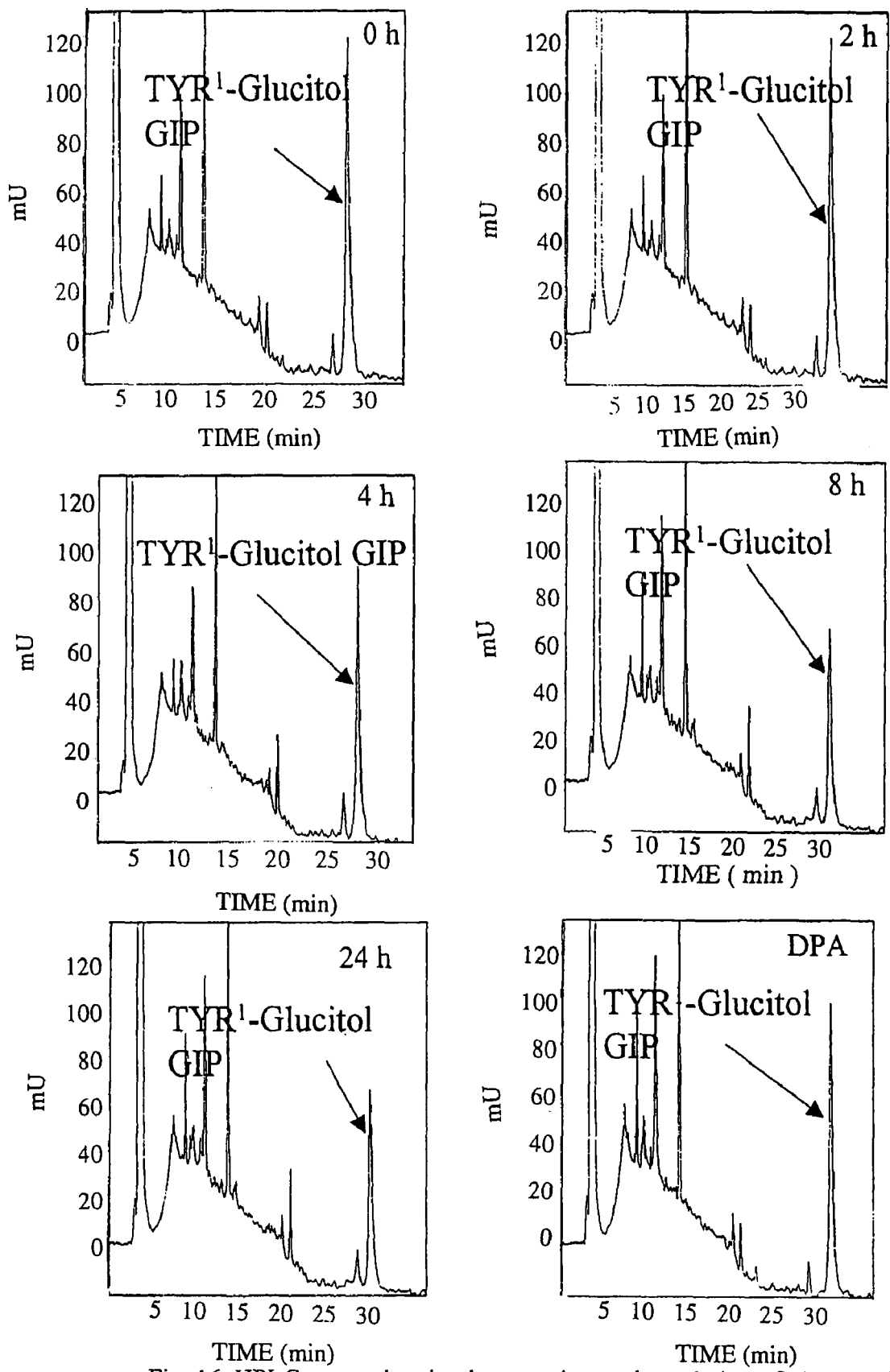
Fig. 16. HPLC traces showing human plasma degradation of glycated GIP.

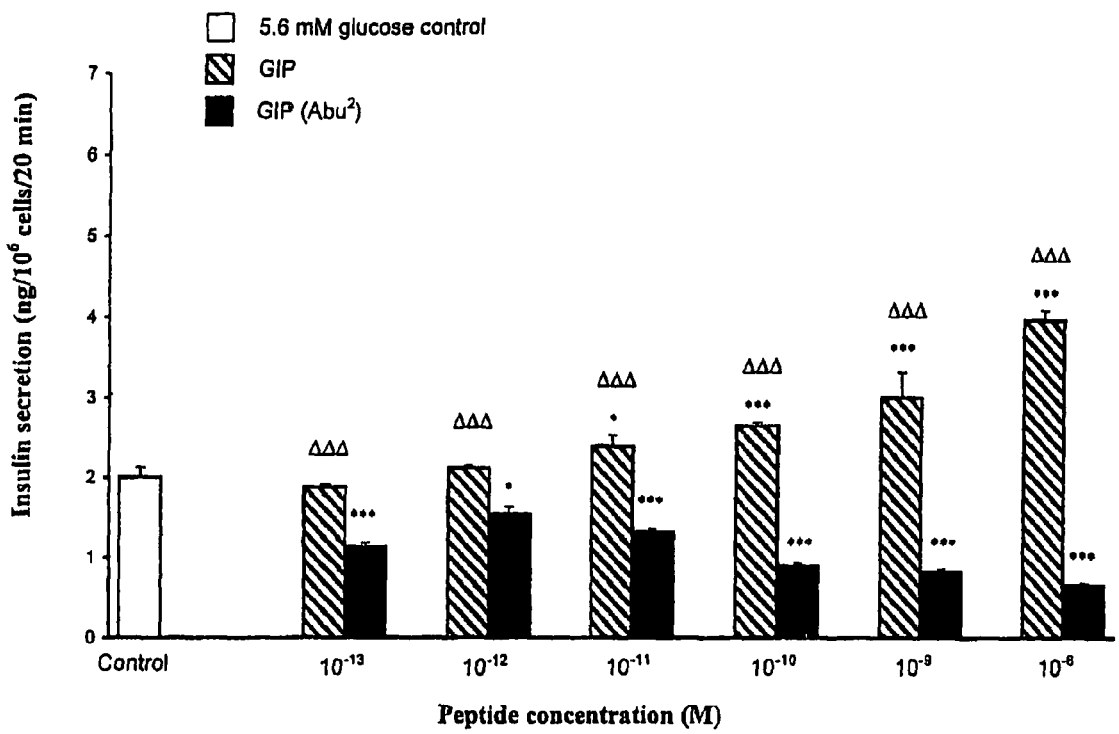
Fig. 17. Graph showing the effects of various concentrations of GIP and GIP (Abu$^2$) on insulin release from BRIN-BD11 cells incubated at 5.6 mM glucose
Values are means ± S.E.M. for 12 separate observations. *P< 0.05, P< 0.01, *P<0.001 compared to control (5.6mM glucose alone). $^{\Delta}$P<0.05, $^{\Delta\Delta}$P<0.01, $^{\Delta\Delta\Delta}$P<0.001 compared to GIP (Abu$^2$) at the same concentration.

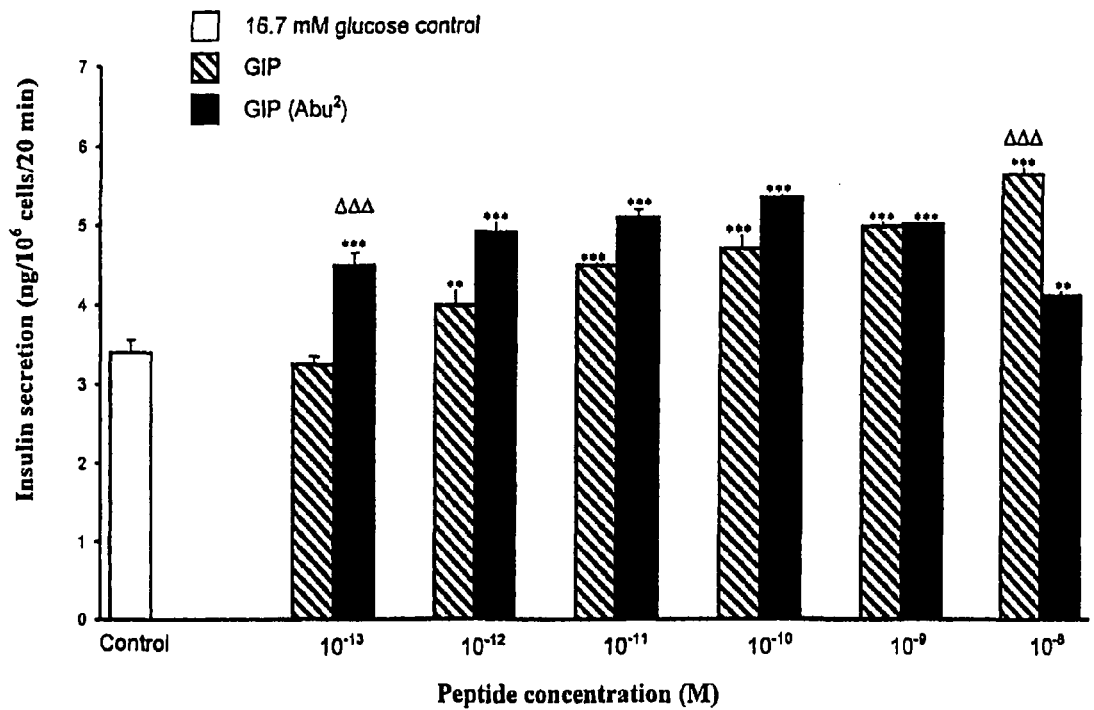
Fig. 18. Graph showing the effects of various concentrations of GIP and GIP (Abu$^2$) on insulin release from BRIN-BD11 cells incubated at 16.7 mM glucose
Values are means ± S.E.M. for 12 separate observations. *P< 0.05, P< 0.01, *P<0.001 compared to control (16.7 mM glucose alone). ΔP<0.05, ΔΔP<0.01, ΔΔΔP<0.001 compared to GIP (Abu$^2$) at the same concentration.

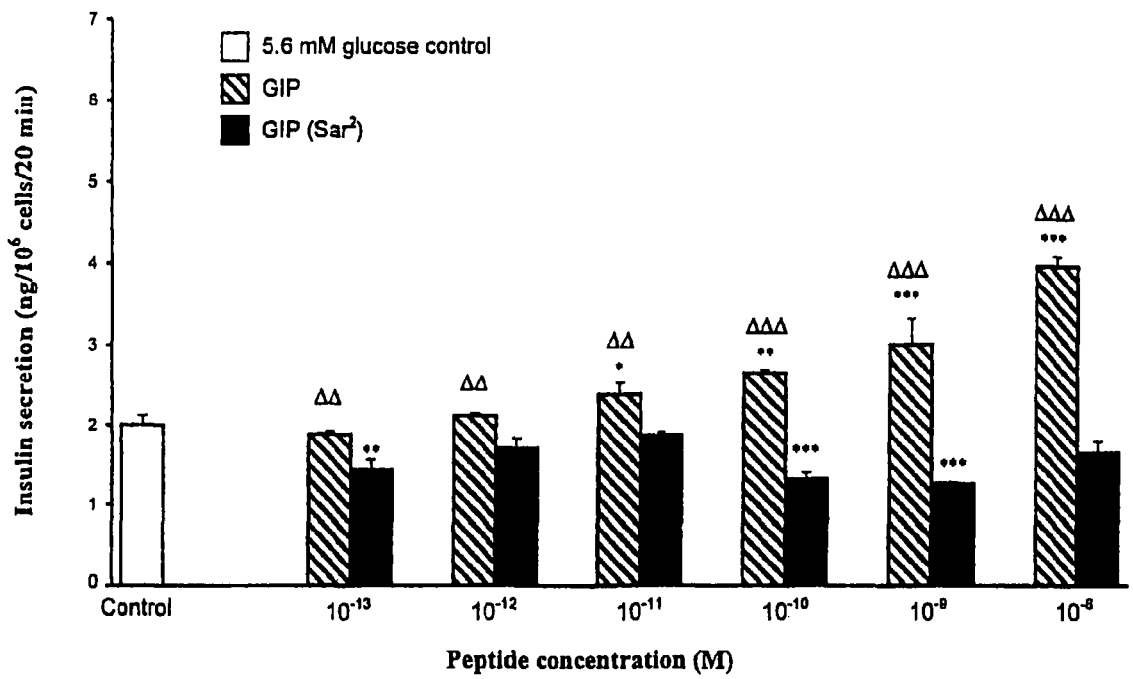
Fig.19. Graph showing the effects of various concentrations of GIP and GIP (Sar$^2$) on insulin release from BRIN-BD11 cells incubated at 5.6 mM glucose
Values are means ± S.E.M. for 12 separate observations. *P< 0.05, P< 0.01, *P<0.001 compared to control (5.6mM glucose alone). $^\Delta$P<0.05, $^{\Delta\Delta}$P<0.01, $^{\Delta\Delta\Delta}$P<0.001 compared to GIP (Sar$^2$) at the same concentration.

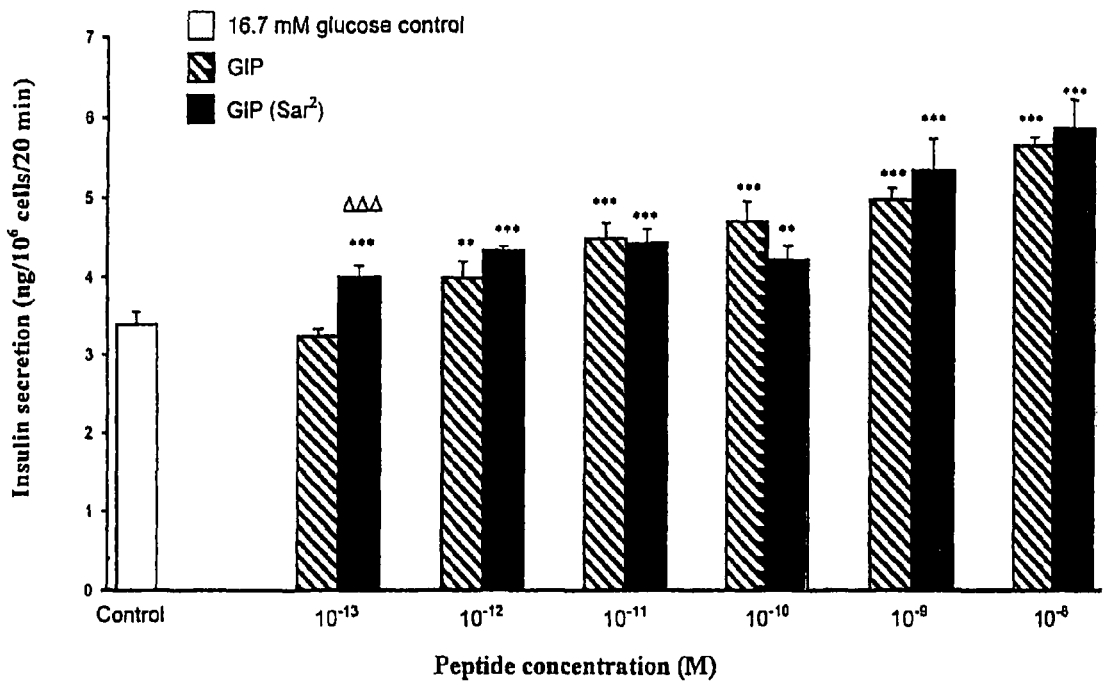
Fig. 20. Graph showing the effects of various concentrations of GIP and GIP (Sar$^2$) on insulin release from BRIN-BD11 cells incubated at 16.7 mM glucose
Values are means ± S.E.M. for 12 separate observations. $^*P< 0.05$, $^{}P< 0.01$, $^{*}P<0.001$ compared to control (16.7 mM glucose alone). $^\Delta P<0.05$, $^{\Delta\Delta}P<0.01$, $^{\Delta\Delta\Delta}P<0.001$ compared to GIP (Sar$^2$) at the same concentration.

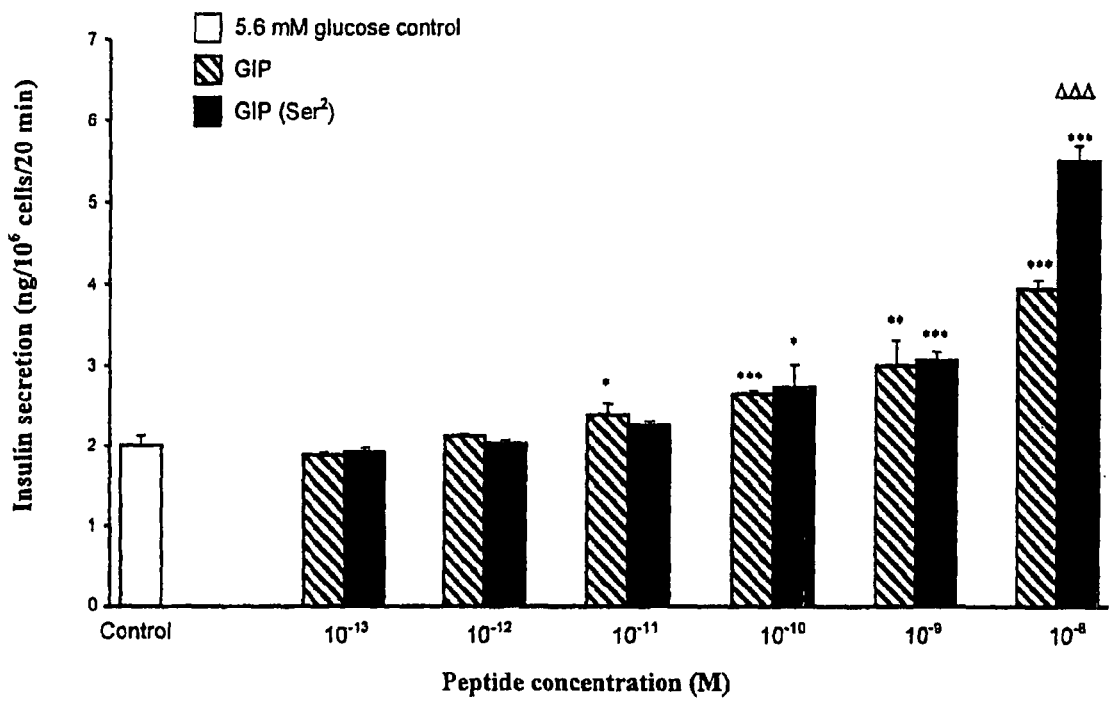

Fig.21. Graph showing the effects of various concentrations of GIP and GIP (Ser$^2$) on insulin release from BRIN-BD11 cells incubated at 5.6 mM glucose Values are means ± S.E.M. for 12 separate observations. $^*P< 0.05$, $^{}P< 0.01$, $^{*}P<0.001$ compared to control (5.6mM glucose alone). $^{\triangle}P<0.05$, $^{\triangle\triangle}P<0.01$, $^{\triangle\triangle\triangle}P<0.001$ compared to GIP (Ser$^2$) at the same concentration.

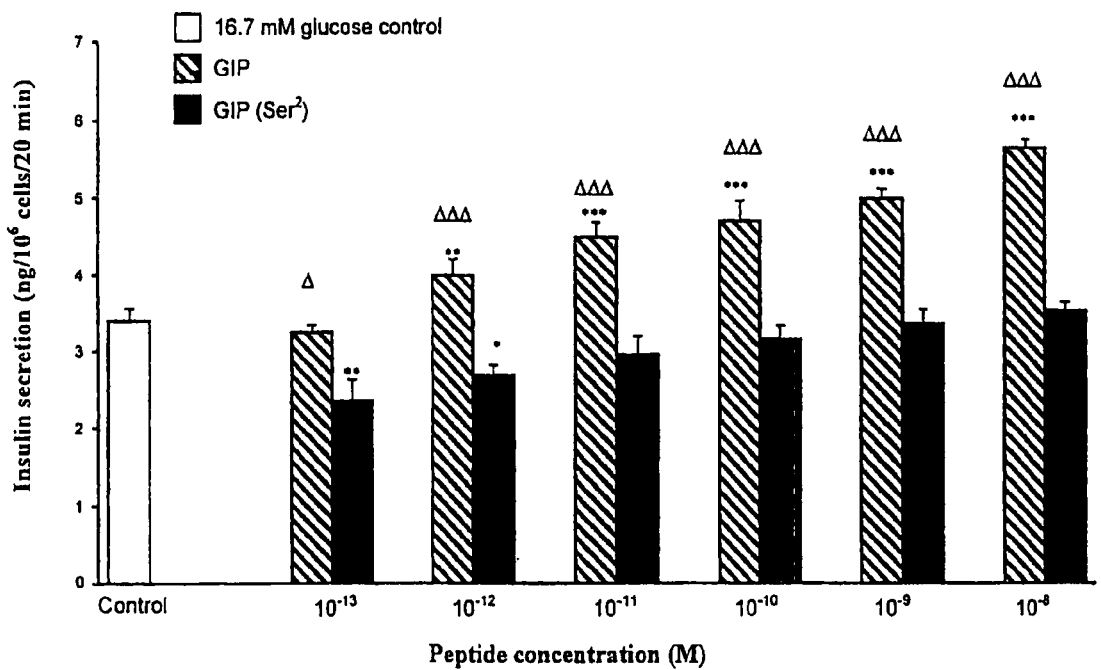
Fig. 22. Graph showing the effects of various concentrations of GIP and GIP (Ser$^2$) on insulin release from BRIN-BD11 cells incubated at 16.7 mM glucose
Values are means ± S.E.M. for 12 separate observations. $^*P< 0.05$, $^{}P< 0.01$, $^{*}P<0.001$ compared to control (16.7 mM glucose alone). $^\Delta P<0.05$, $^{\Delta\Delta}P<0.01$, $^{\Delta\Delta\Delta}P<0.001$ compared to GIP (Ser$^2$) at the same concentration.

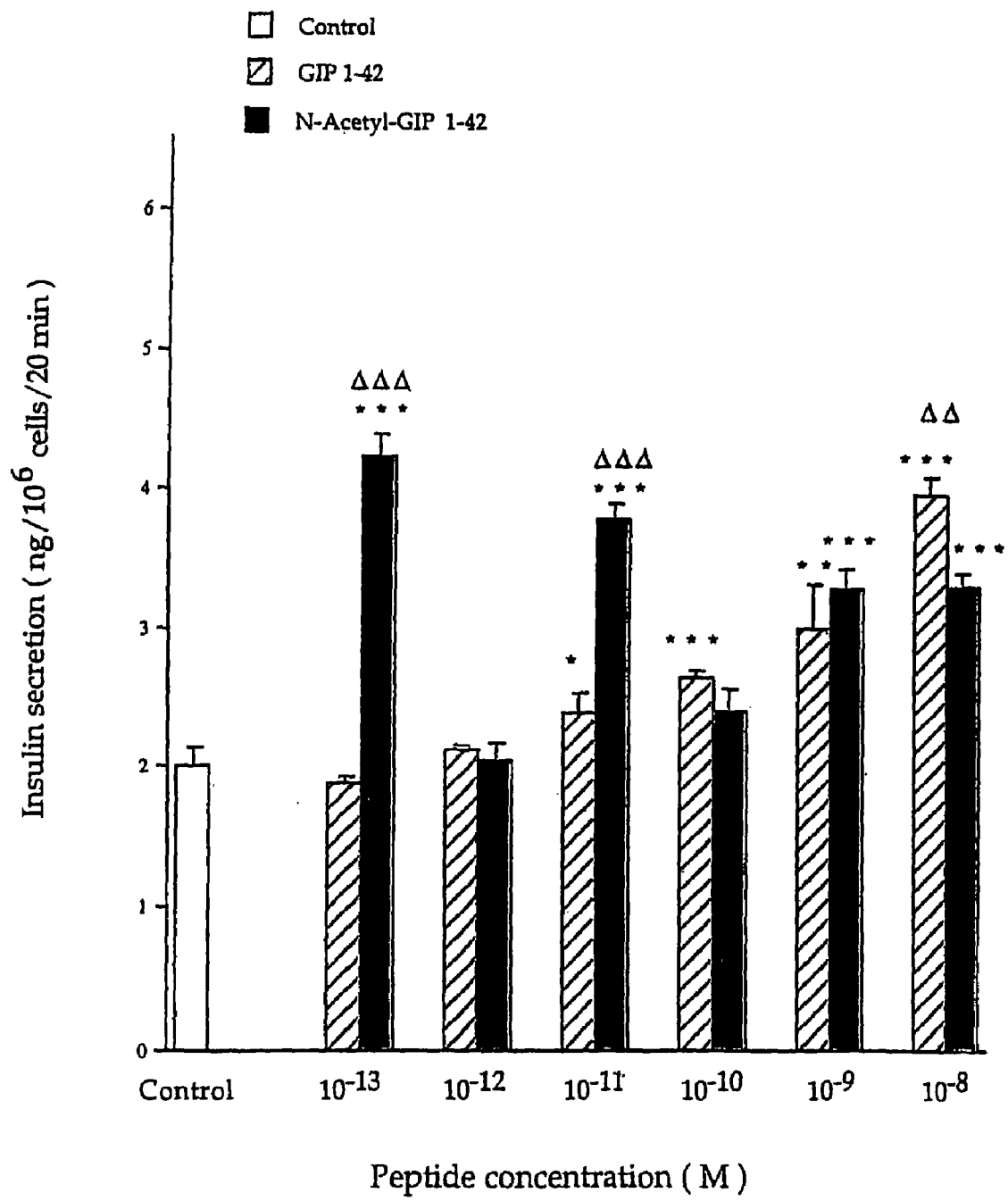
Fig. 23 Graph showing the effects of various concentrations of GIP 1-42 and N-Acetyl-GIP 1-42 on insulin release from BRIN-BD11 cells incubated at 5.6 mM glucose

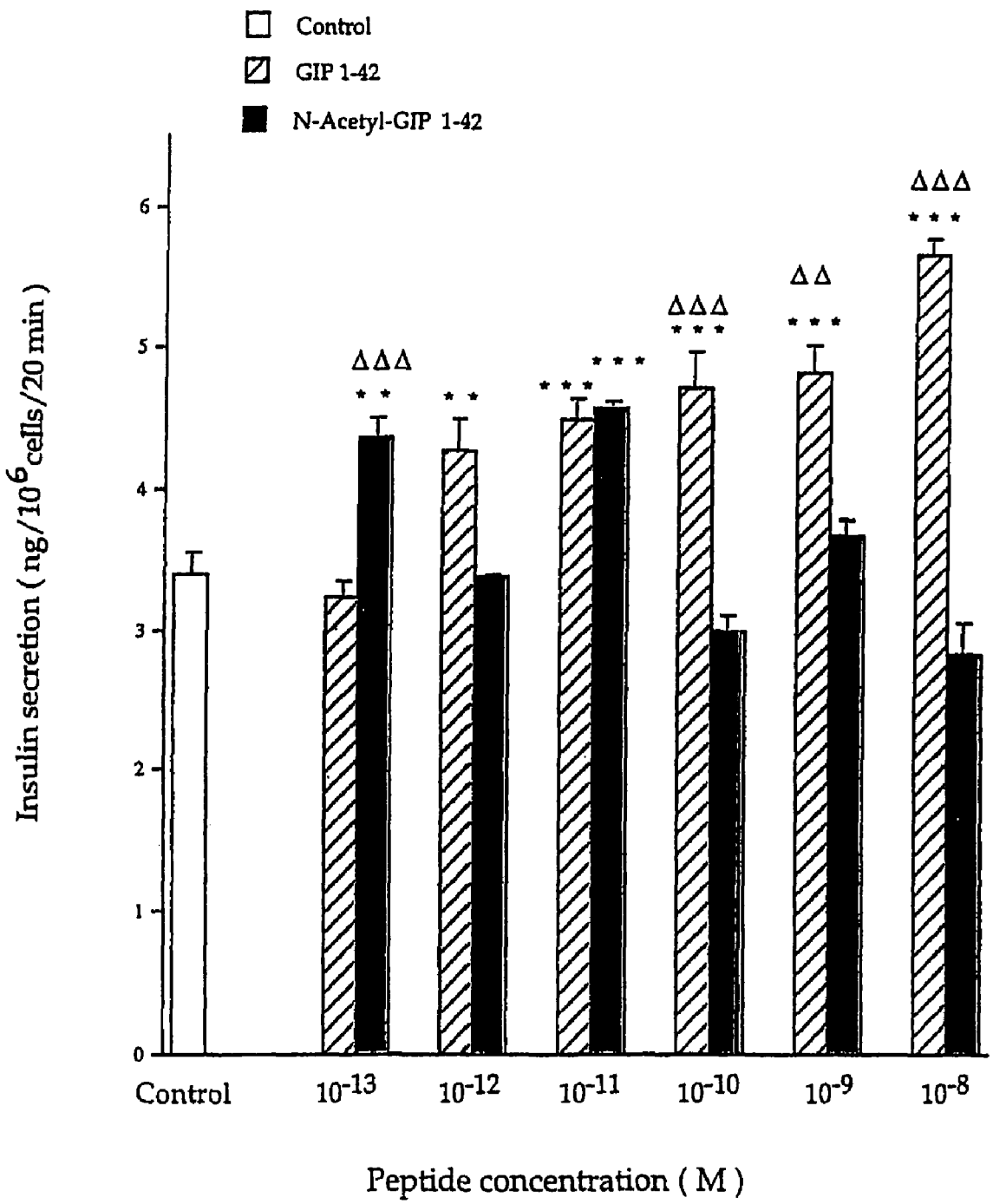
Fig. 24 Graph showing the effects of various concentrations of GIP 1-42 and N-Acetyl-GIP 1-42 on insulin release from BRIN-BD11 cells incubated at 16.7 mM glucose

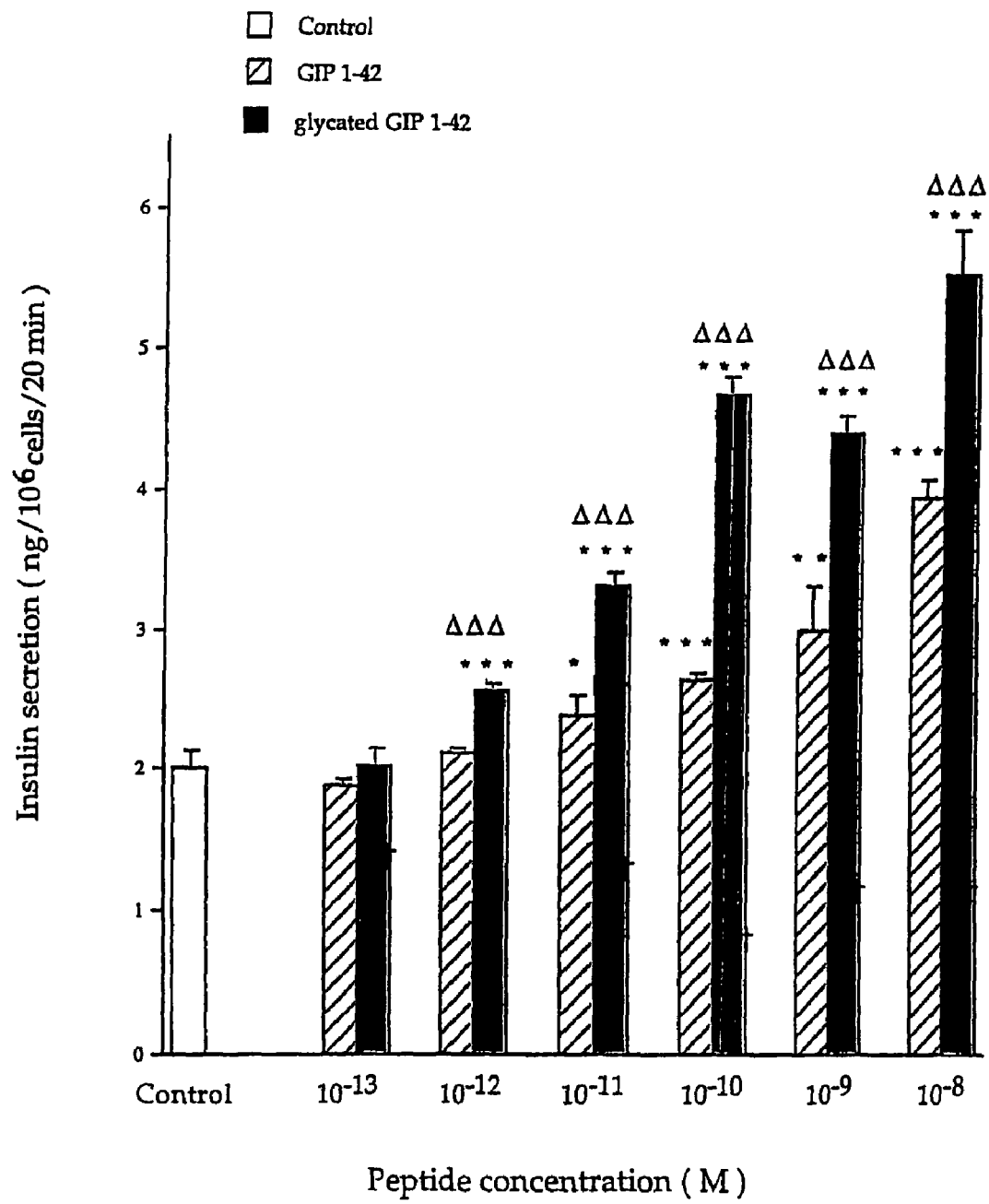
Fig. 25 Graph showing the effects of various concentrations of GIP 1-42 and glycated GIP 1-42 on insulin release from BRIN-BD11 cells incubated at 5.6 mM glucose

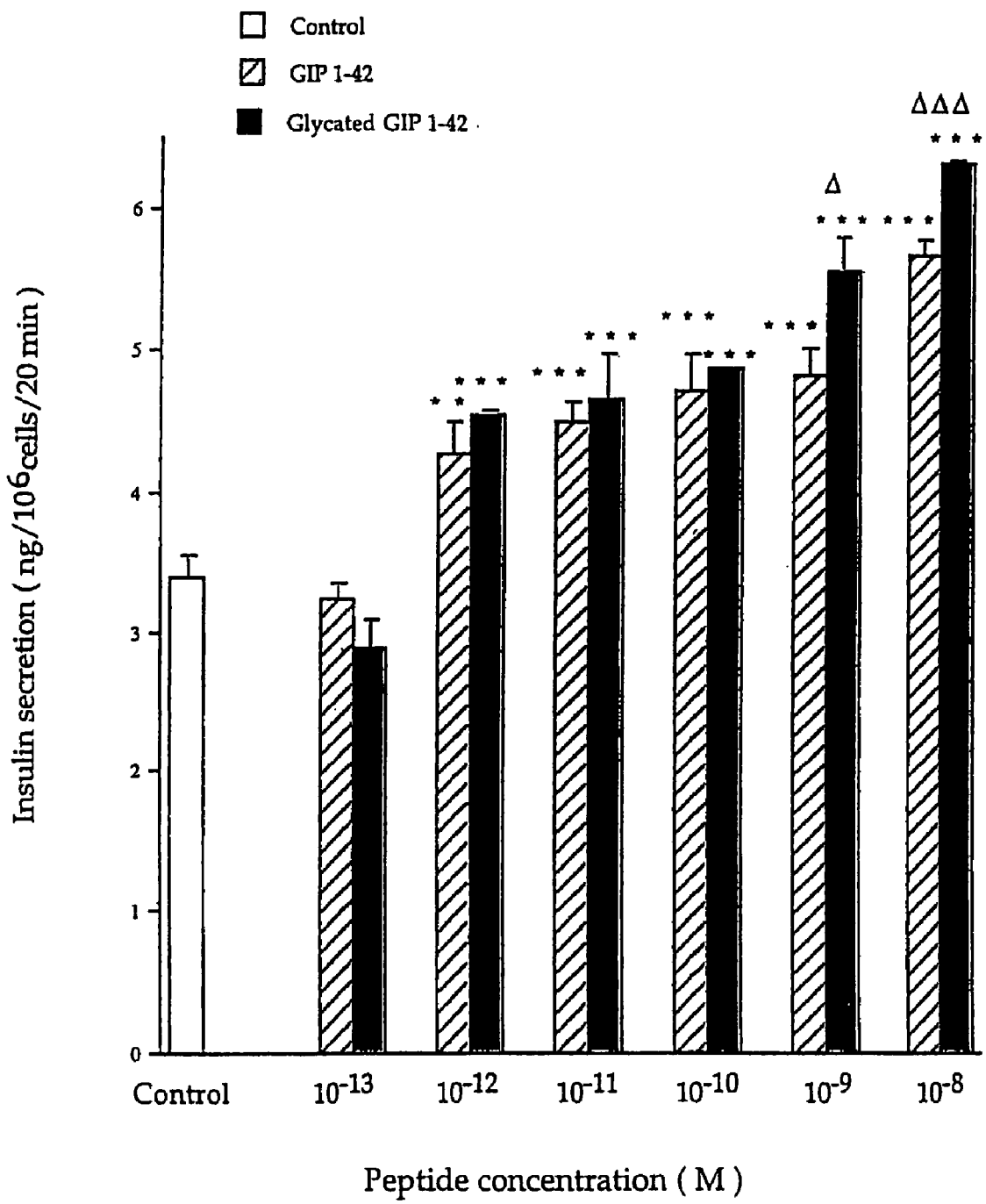
Fig. 26 Graph showing the effects of various concentrations of GIP 1-42 and glycated GIP 1-42 on insulin release from BRIN-BD11 cells incubated at 16.7 mM glucose

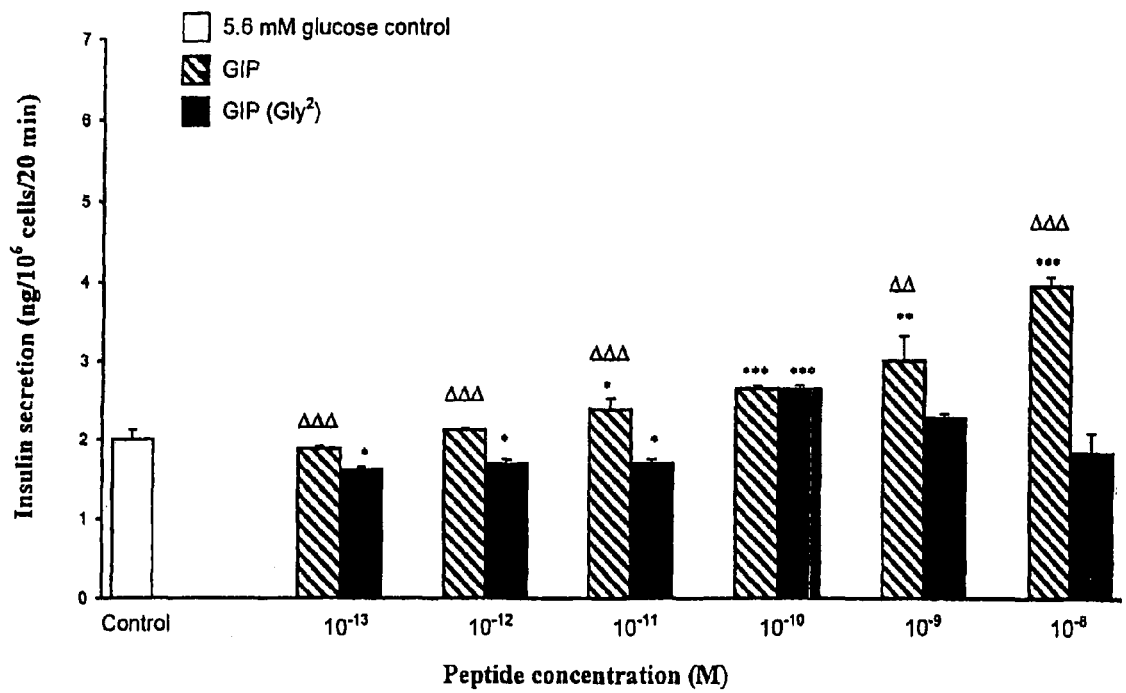
Fig. 27 Graph showing the effects of various concentrations of GIP and GIP (Gly$^2$) on insulin release from BRIN-BD11 cells incubated at 5.6 mM glucose
Values are means ± S.E.M. for 12 separate observations. $^*P< 0.05$, $^{}P< 0.01$, $^{*}P<0.001$ compared to control (5.6mM glucose alone). $^{\Delta}P<0.05$, $^{\Delta\Delta}P<0.01$, $^{\Delta\Delta\Delta}P<0.001$ compared to GIP (Gly$^2$) at the same concentration.

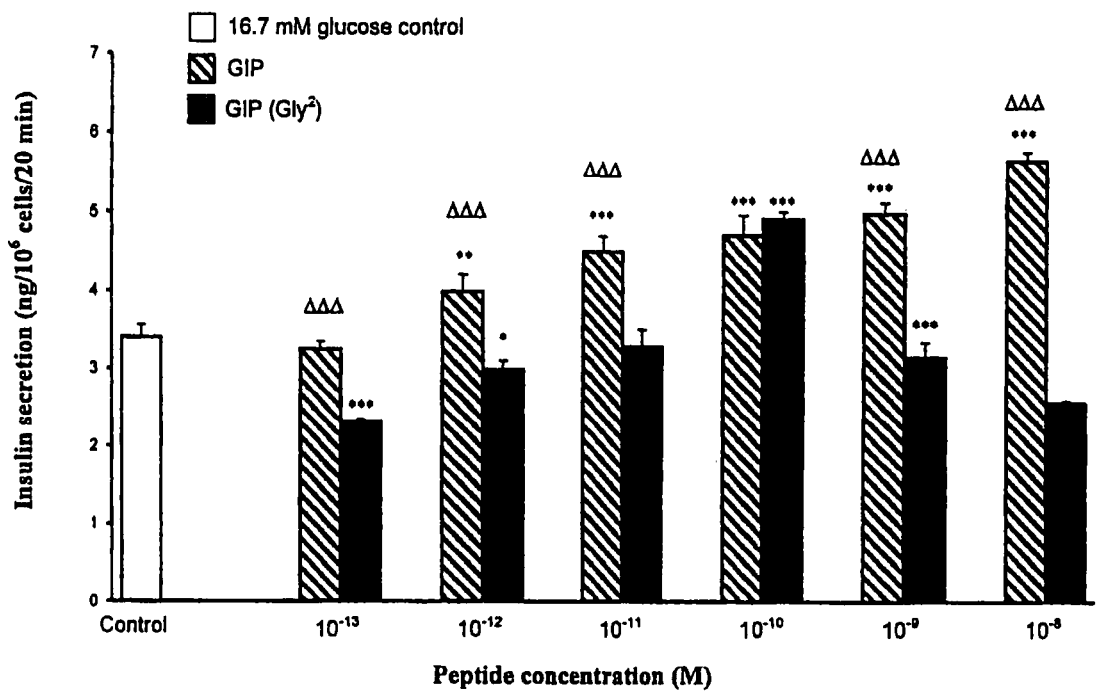
Fig. 28 Graph showing the effects of various concentrations of GIP and GIP (Gly$^2$) on insulin release from BRIN-BD11 cells incubated at 16.7 mM glucose
Values are means ± S.E.M. for 12 separate observations. *P< 0.05, P< 0.01, *P<0.001 compared to control (16.7 mM glucose alone). ΔP<0.05, ΔΔP<0.01, ΔΔΔP<0.001 compared to GIP (Gly$^2$) at the same concentration.

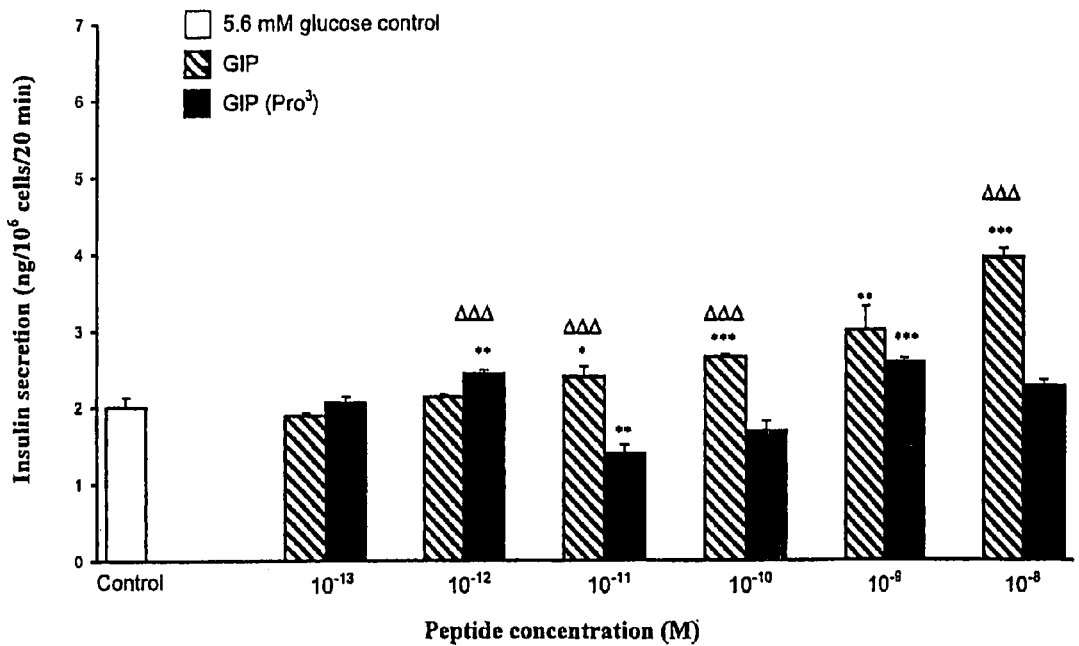
Fig. 29 Graph showing the effects of various concentrations of GIP and GIP (Pro$^3$) on insulin release from BRIN-BD11 cells incubated at 5.6 mM glucose
Values are means ± S.E.M. for 12 separate observations. $^*P< 0.05$, $^{}P< 0.01$, $^{*}P<0.001$ compared to control (5.6mM glucose alone). $^{\Delta}P<0.05$, $^{\Delta\Delta}P<0.01$, $^{\Delta\Delta\Delta}P<0.001$ compared to GIP (Pro$^3$) at the same concentration.

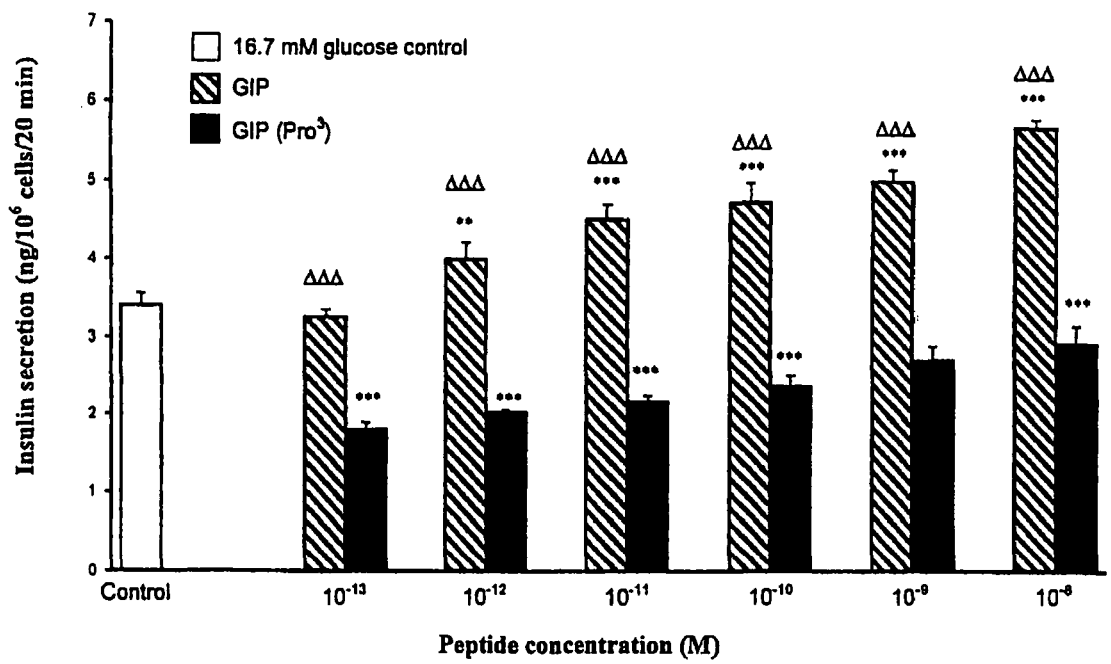

Fig. 30 Graph showing the effects of various concentrations of GIP and GIP (Pro$^3$) on insulin release from BRIN-BD11 cells incubated at 16.7 mM glucose Values are means ± S.E.M. for 12 separate observations. $^*P<0.05$, $^{}P<0.01$, $^{*}P<0.001$ compared to control (16.7 mM glucose alone). $^{\triangle}P<0.05$, $^{\triangle\triangle}P<0.01$, $^{\triangle\triangle\triangle}P<0.001$ compared to GIP (Pro$^3$) at the same concentration.

Fig. 31A

```
             5                    10                    15
NH2-Tyr-Ala-Glu-Gly-Thr-Phe-Ile-Ser-Asp-Tyr-Ser-Ile-Ala-Met-Asp- 20                    25                   30
  -Lys-Ile-His-Gln-Gln-Asp-Phe-Val-Asn-Trp-Leu-Leu-Ala-Gln-Lys- 35                    40
  Gly-Lys-Lys-Asn-Asp-Trp-Lys-His-Asn-Ile-Thr-Gln-COOH
```

(SEQ ID NO:1)

Fig. 31B

```
             5                    10                    15
NH2-Tyr-Ala-Glu-Gly-Thr-Phe-Ile-Ser-Asp-Tyr-Ser-Ile-Ala-Met-Asp- 20                    25                   30
  -Lys-Ile-ArgGln-Gln-Asp-Phe-Val-Asn-Trp-Leu-Leu-Ala-Gln-Lys- 35                    40
  Gly-Lys-Lys-Ser-Asp-Trp-Lys-His-Asn-Ile-Thr-Gln-COOH
```

(SEQ ID NO:2)

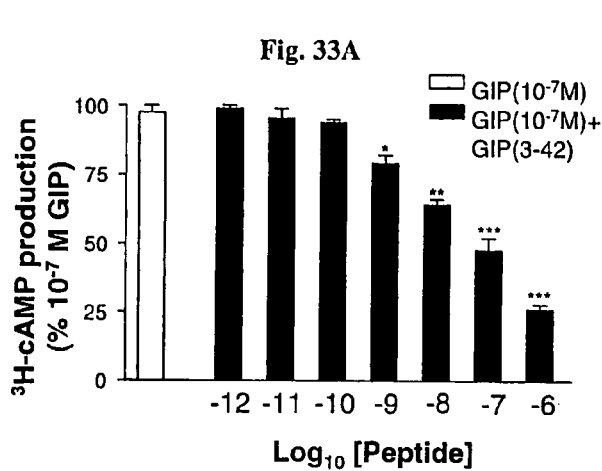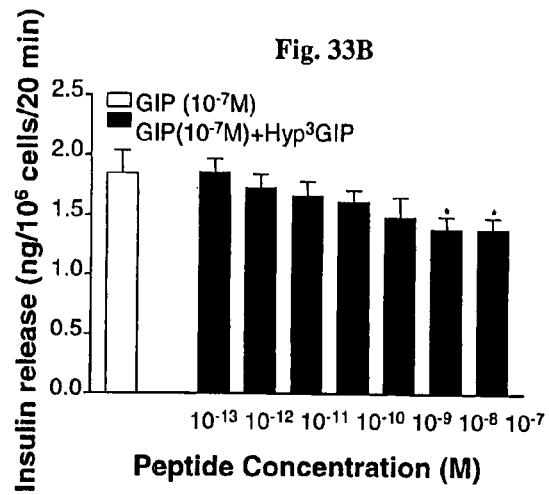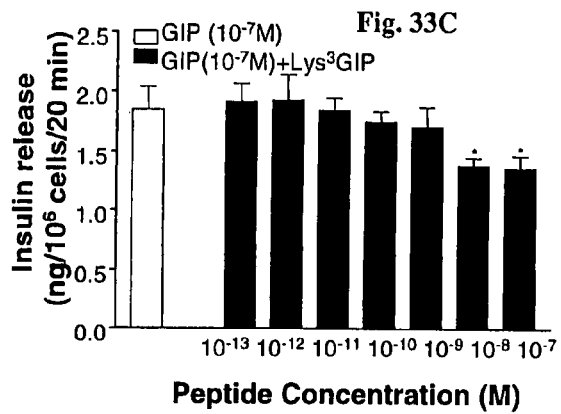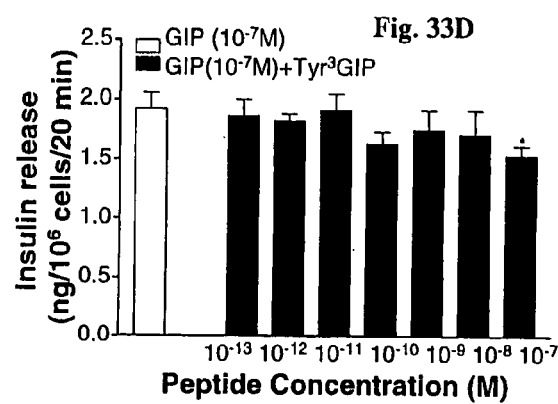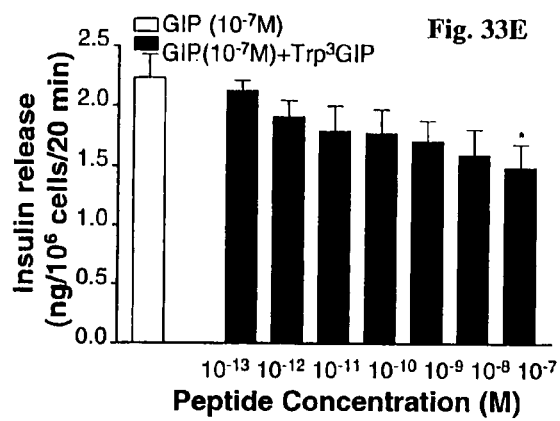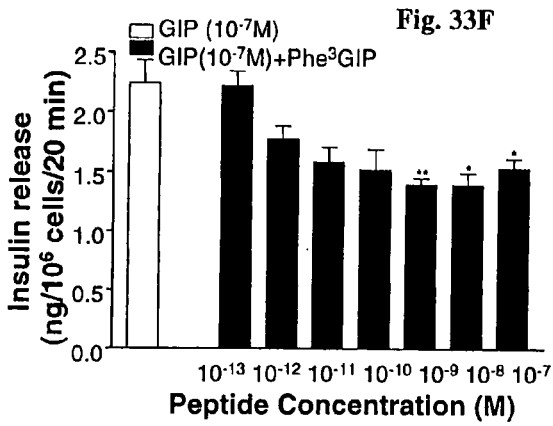

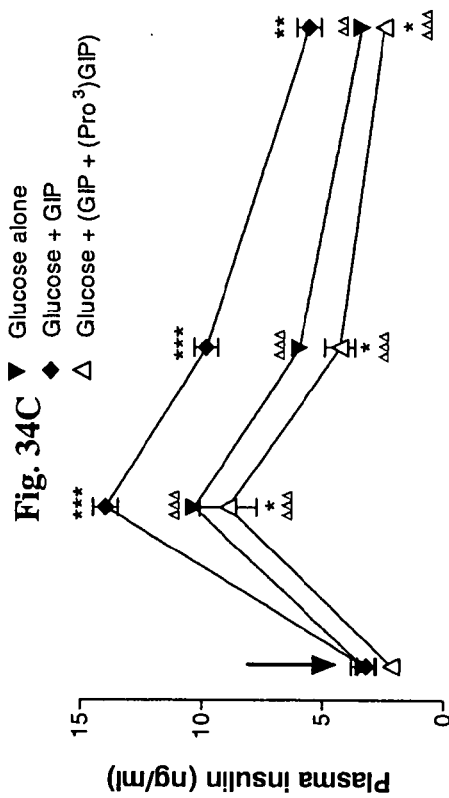
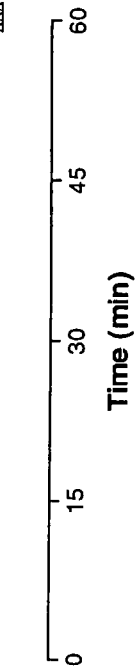
Fig. 34C
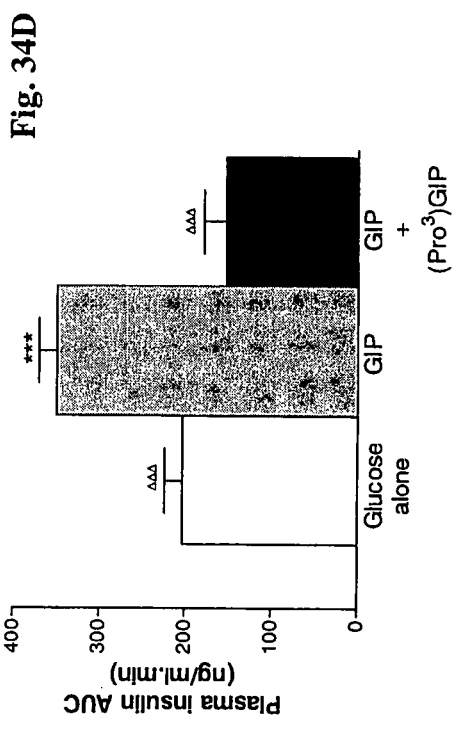
Fig. 34D
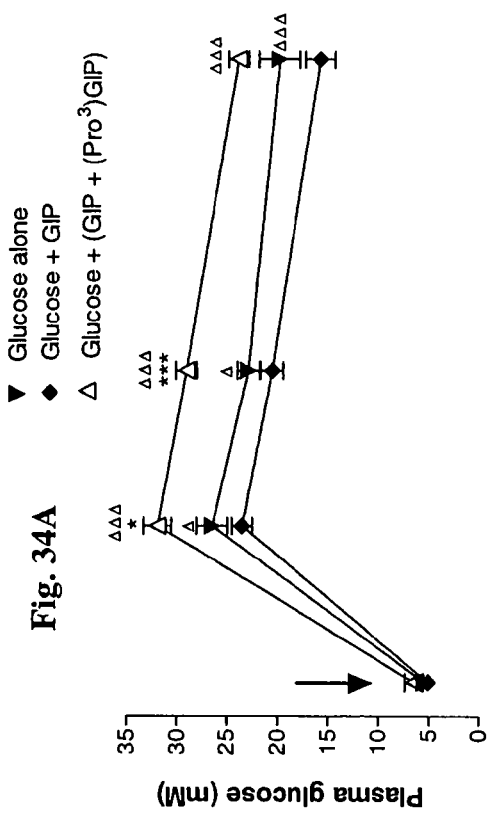
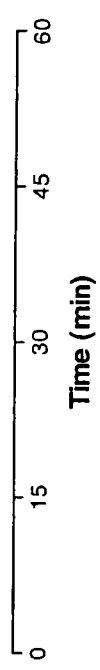
Fig. 34A
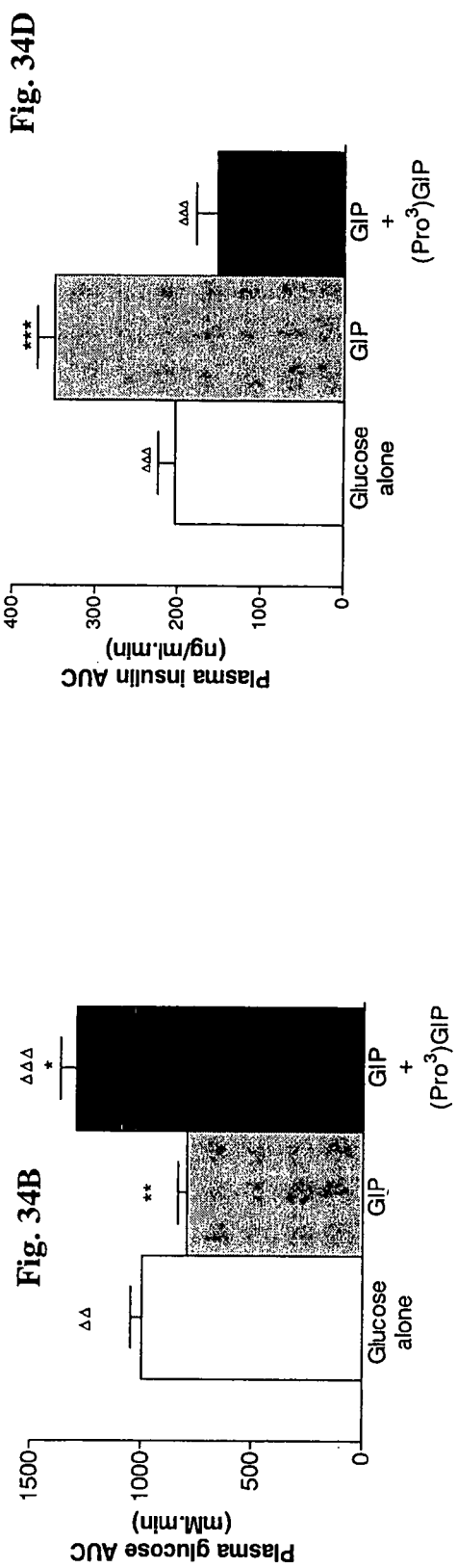
Fig. 34B

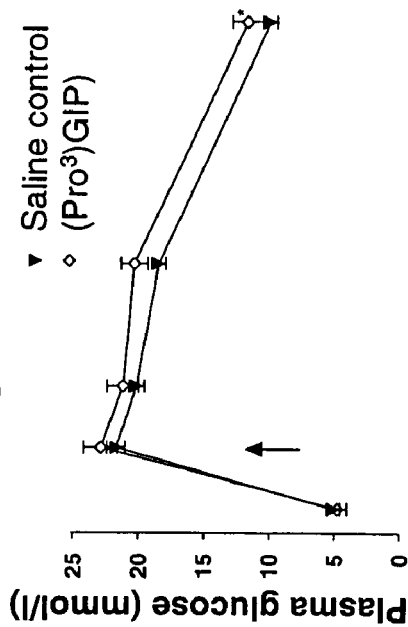
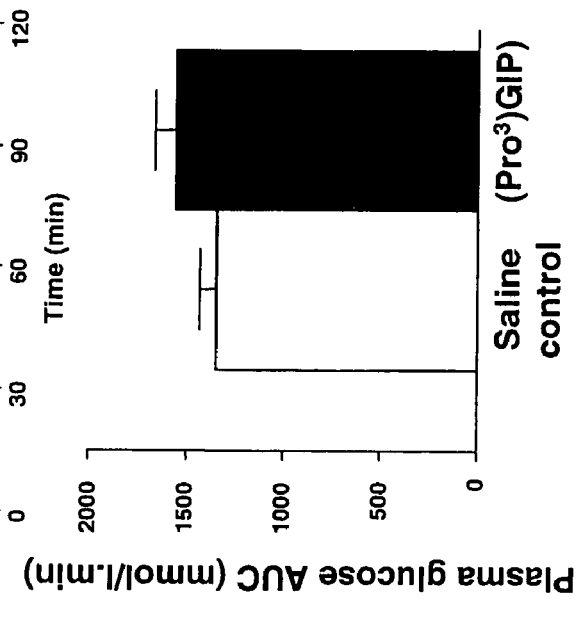
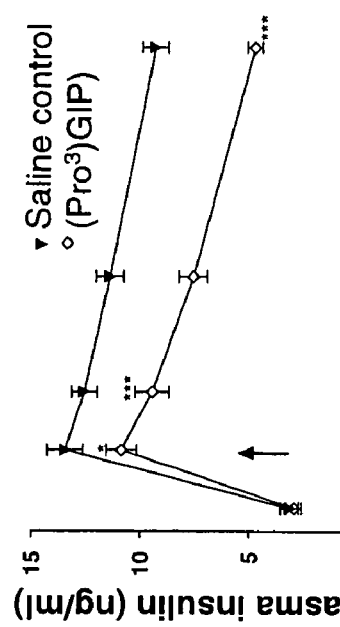
Fig. 35A
Fig. 35B
Fig. 35C
Fig. 35D

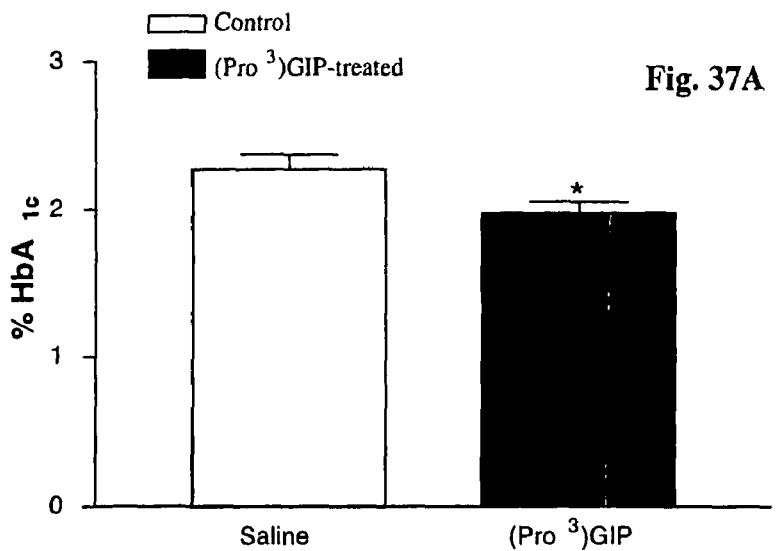
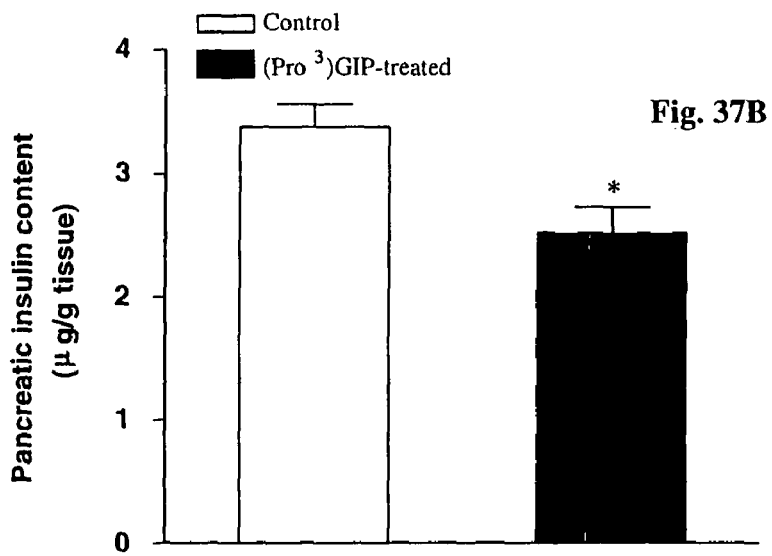
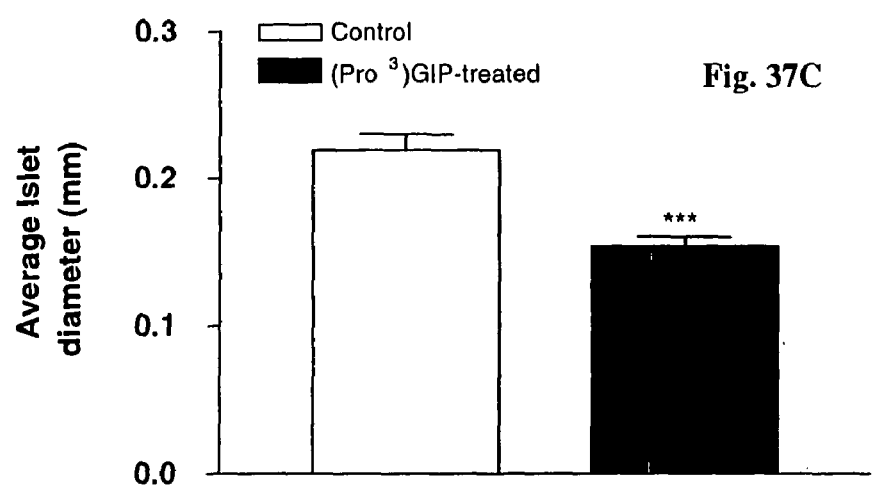
Fig. 37A
Fig. 37B
Fig. 37C

After 11 days treatment

After 9 days cessation of treatment

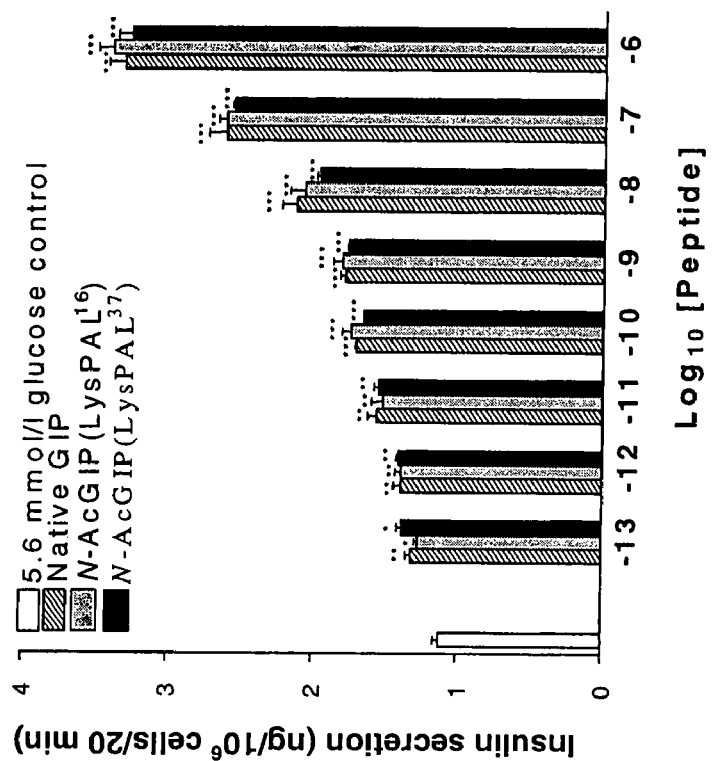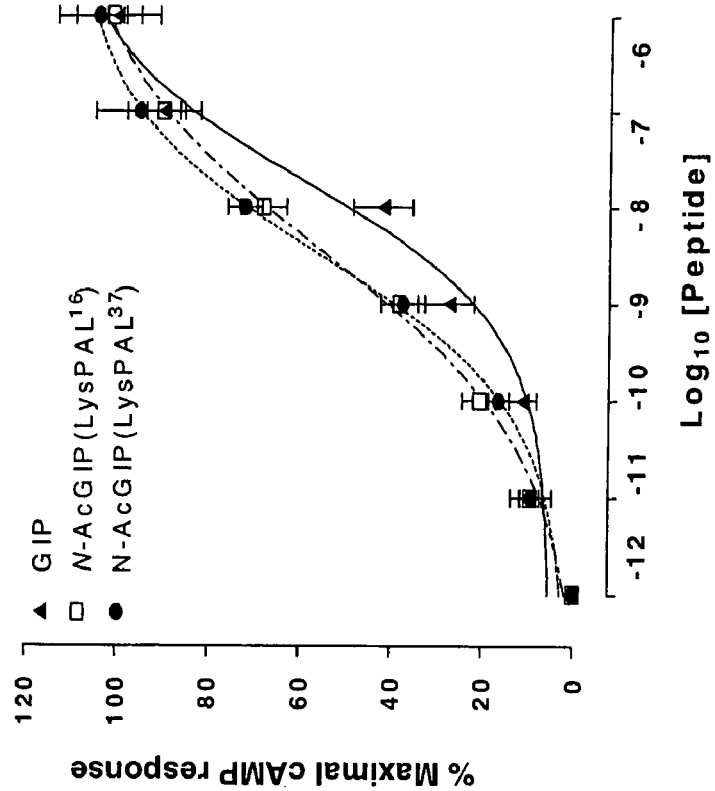
Fig. 50

PEPTIDE ANALOGUES OF GIP FOR TREATMENT OF DIABETES, INSULIN RESISTANCE AND OBESITY

CROSS-REFERENCE TO RELATED APPLICATIONS

This application is a continuation of U.S. application Ser. No. 11/090,787, filed Mar. 25, 2005, which is a continuation-in-part application of International Application No. PCT/GB2005/000710, which was filed Feb. 25, 2005, designated the United States and was published in English, which claims benefit of U.K. Application No. GB 0404124.0, filed Feb. 25, 2004. The entire teachings of the above applications and of U.S. application Ser. No. 09/937,687, filed Jan 8, 2002, International Application No. PCT/GB00/01089, filed Mar. 29, 2000, GB9907216.7, filed Mar. 29, 1999, and GB9917565.5, filed Jul. 27, 1999, are incorporated herein by reference.

FIELD OF THE INVENTION

The present invention relates to the release of insulin and the control of blood glucose concentration. More particularly the invention relates to antagonists of gastric inhibitory peptide (GIP) as pharmaceutical preparations for treatment of type 2 diabetes.

BACKGROUND

Obesity and diabetes are predicted to reach epidemic proportions throughout the world in the next 20 years and current treatments do not restore normal insulin sensitivity or glucose homeostasis, therein resulting in debilitating diabetic complications and premature death.

Gastric inhibitory polypeptide (GIP) and glucagon-like peptide-1(7-36)amide (truncated GLP-1; tGLP-1) are two important insulin-releasing hormones secreted from endocrine cells in the intestinal tract in response to feeding. Together with autonomic nerves they play a vital supporting role to the pancreatic islets in the control of blood glucose homeostasis and nutrient metabolism.

GIP is released from intestinal endocrine K-cells into the bloodstream following ingestion of carbohydrate, protein and particularly fat (Meier, J. J. et al., 2002, *Regul. Pept.* 107:1-13). GIP was initially discovered through its ability to inhibit gastric acid secretion (Brown, J. C. et al. 1969, *Can. J. Physiol. Pharmacol.* 47:113-114) but its major physiological role is now generally believed to be that of an incretin hormone that targets pancreatic islets to enhance insulin secretion and help reduce postprandial hyperglycemia (Creutzfeldt, W., 2001, *Exp. Clin. Endocrinol. Diabetes* 109: S288-S303). GIP acts through binding to specific G-protein coupled GIP receptors located on pancreatic beta-cells (Wheeler, M. B. et al., 1995, *Endocrinology* 136:4629-4639). Like its sister incretin hormone, glucagon-like peptide-1 (GLP-1), this ability to stimulate insulin secretion plus other potentially beneficial actions on pancreatic beta-cell growth and differentiation have led to much interest in using GIP or GLP-1 receptor agonists in the treatment of type 2 diabetes (Creutzfeldt, W., 2001, *Exp. Clin. Endocrinol. Diabetes* 109: S288-S303; Holz, G. G. et al., 2003, *Curr. Med. Chem.* 10:2471-2483).

Since GIP functions as a potent and natural stimulator of insulin secretion released from the intestine by feeding, it is widely expected that antagonists opposing GIP action will block the insulin-releasing actions of GIP and impair both oral glucose tolerance and the glycemic response to nutrient ingestion. In fact, all studies published to date indicate that GIP is a key physiological component of the enteroinsular axis and that functional ablation of GIP leads to impaired glucose homeostasis moving the metabolic characteristic towards a type 2 diabetes phenotype (Gault, V. A. et al., 2002, *Biochem. Biophys. Res. Commun.* 290:1420-1426).

Dipeptidyl peptidase IV (DPP IV; EC 3.4.14.5) has been identified as a key enzyme responsible for inactivation of GIP and tGLP-1 in serum. This occurs through the rapid removal of the N-terminal dipeptides $Tyr^1$-$Ala^2$ and $His^7$-$Ala^8$ giving rise to the main metabolites GIP(3-42) and GLP-1(9-36) amide, respectively. These truncated peptides are reported to lack biological activity or to even serve as antagonists at GIP or tGLP-1 receptors. The resulting biological half-lives of these incretin hormones in vivo are therefore very short, estimated to be no longer than 5 minutes. DPP IV is completely inhibited in serum by the addition of diprotin A (DPA, 0.1 mmol/l).

In situations of normal glucose regulation and pancreatic B-cell sensitivity, this short duration of action is advantageous in facilitating momentary adjustments to homeostatic control. However, the current goal of a possible therapeutic role of incretin hormones, particularly tGLP-1 in non-insulin dependent diabetes (NIDDM) therapy is frustrated by a number of factors in addition to finding a convenient route of administration. Most notable of these are rapid peptide degradation and rapid absorption (peak concentrations are reached in 20 minutes) and the resulting need for both high dosage and precise timing with meals. Recent therapeutic strategies have focused on precipitated preparations to delay peptide absorption and inhibition of GLP-1 degradation using specific inhibitors of DPP IV. A possible therapeutic role is also suggested by the observation that a specific inhibitor of DPP IV, isoleucine thiazolidide, lowered blood glucose and enhanced insulin secretion in glucose-treated diabetic obese Zucker rats presumably by protecting against catabolism of the incretin hormones tGLP-1 and GIP.

Studies have indicated that tGLP-1 infusion restores pancreatic B-cell sensitivity, insulin secretory oscillations and improved glycemic control in various groups of patients with impaired glucose tolerance (IGT) or NIDDM. Longer term studies also show significant benefits of tGLP-1 injections in NIDDM and possibly IDDM therapy, providing a major incentive to develop an orally effective or long-acting tGLP-1 analogue. Several attempts have been made to produce structurally modified analogues of tGLP-1 which are resistant to DPP IV degradation. A significant extension of serum half-life is observed with $His^7$-glucitol tGLP-1 and tGLP-1 analogues substituted at position 8 with Gly, Aib (amino isobutyric acid), Ser or Thr. However, these structural modifications seem to impair receptor binding and insulinotrophic activity thereby compromising part of the benefits of protection from proteolytic degradation. In recent studies using $His^7$-glucitol tGLP-1, resistance to DPP IV and serum degradation was accompanied by severe loss of insulin releasing activity.

GIP shares not only the same degradation pathway as tGLP-1 but many similar physiological actions, including stimulation of insulin and somatostatin secretion, and the enhancement of glucose disposal. These actions are viewed as key aspects in the antihyperglycemic properties of tGLP-1, and there is therefore good expectation that GIP may have similar potential as NIDDM therapy. Indeed, compensation by GIP is held to explain the modest disturbances of glucose homeostasis observed in tGLP-1 knockout mice. Apart from early studies, the anti-diabetic potential of GIP has not been explored and tGLP-1 may seem more attractive since it is viewed by some as a more potent insulin secretagogue when infused at so called physiological concentrations estimated by radioimmunoassay (RIA).

There is therefore a need for a diabetes treatment that includes an analogue of GIP which can cause release of insulin, yet also be resistant to rapid degradation by DPP IV.

SUMMARY OF THE INVENTION

Disclosed herein are GIP antagonist peptides which are resistant to rapid degradation by DPP IV.

The invention includes a peptide analogue of GIP(1-42) (SEQ ID NO:1), which includes at least 12 amino acid residues from the N-terminal end of GIP(3-42). The invention also includes a peptide analogue of GIP(1-42) (SEQ ID NO:1), which includes at least 12 amino acid residues from the N-terminal end of GIP(1-42) and having an amino acid substitution at $Glu^3$.

The amino acid substituted at $Glu^3$ can be selected from the group consisting of: proline, hydroxyproline, lysine, tyrosine, phenylalanine and tryptophan. Specifically, a proline can be substituted for $Glu^3$. The peptide analogue can further include modification by fatty acid addition at an epsilon amino group of at least one lysine residue. The lysine residue can be $Lys^6$, or $Lys^{37}$.

The peptide analogue of GIP(1-42) (SEQ ID NO:1) can include at least 12 amino acid residues from the N-terminal end of GIP(1-42), and an amino acid modification at amino acid residues 1, 2 or 3. The N-terminal amino acid residue can be acetylated. It can further comprising modification by fatty acid addition at an epsilon amino group of at least one lysine residue. The modification can be the linking of, e.g., a C-8, a C-10, a C-12, a C-14, a C-16, a C-18 or a C-20 palmitate group to the epsilon amino group of a lysine residue. The lysine residue can be $Lys^{16}$, or $Lys^{37}$.

The invention also includes a peptide analogue of GIP(1-42) (SEQ ID NO:1), wherein the analogue comprises a base peptide consisting of one of the following: GIP(1-12), GIP(1-13), GIP(1-14), GIP(1-15), GIP(1-16), GIP(1-17), GIP(1-18), GIP(1-19), GIP(1-20), GIP(1-21), GIP(1-22), GIP(1-23), GIP(1-24), GIP(1-25), GIP(1-26), GIP(1-27), GIP(1-28), GIP(1-29), GIP(1-30), GIP(1-31), GIP(1-32), GIP(1-33), GIP(1-34), GIP(1-35), GIP(1-36), GIP(1-37), GIP(1-38), GIP(1-39), GIP(1-40), GIP(1-41) and GIP(1-42), where the base peptide possesses one or more of the following modifications: (1) an amino acid substitution at $Glu^3$; (2) a modification by fatty acid addition at an epsilon amino group of at least one lysine residue; and (3) a modification by N-terminal acetylation. Such a peptide analogue can have a proline substituted for $Glu^3$. It can also have a modification in the form of a C-16 palmitate group linked to the epsilon amino group of a lysine residue. The modification can be the linking of, e.g., a C-8, a C-10, a C-12, a C-14, a C-16, a C-18 or a C-20 palmitate group to the epsilon amino group of a lysine residue. The lysine residue can be $Lys^{16}$, or $Lys^{37}$.

The invention further includes a peptide analogue of GIP(1-42) (SEQ ID NO:1), comprising at least 12 amino acid residues from the N-terminal end of GIP(3-42), wherein the peptide analogue is resistant to degradation by enzyme DPP IV when compared to naturally-occurring GIP.

Also included is a peptide analogue of GIP(1-42) (SEQ ID NO:1), comprising at least 12 amino acid residues from the N-terminal end of GIP(1-42) and having an amino acid substitution at $Glu^3$, wherein the peptide analogue is resistant to degradation by enzyme DPP IV when compared to naturally-occurring GIP.

In addition, the invention includes a peptide analogue of GIP(1-42) (SEQ ID NO:1), comprising at least 12 amino acid residues from the N-terminal end of GIP(3-42), wherein the peptide analogue modulates insulin secretion.

The invention also includes a peptide analogue of GIP(1-42) (SEQ ID NO:1), comprising at least 12 amino acid residues from the N-terminal end of GIP(1-42) and having an amino acid substitution at $Glu^3$, wherein the peptide analogue modulates insulin secretion.

The invention also includes use of any of the analogues in the preparation of a medicament for the treatment of obesity, insulin resistance, insulin resistant metabolic syndrome (Syndrome X) or type 2 diabetes.

The invention also includes a pharmaceutical composition including the peptide analogues. The pharmaceutical composition can further comprise a pharmaceutically acceptable carrier. The peptide analogue can be in the form of a pharmaceutically acceptable salt, or a pharmaceutically acceptable acid addition salt.

In a further aspect, the invention includes a method of treating insulin resistance, obesity, or type 2 diabetes, where the method comprises administering to a mammal in need of such treatment a therapeutically effective amount of the pharmaceutical composition.

According to the present invention there is provided an effective peptide analogue of the biologically active GIP(1-42) which has improved characteristics for treatment of Type 2 diabetes wherein the analogue comprises at least 15 amino acid residues from the N terminus of GIP(1-42) and has at least one amino acid substitution or modification at position 1-3 and not including $Tyr^1$ glucitol GIP(1-42).

The structures of human and porcine GIP(1-42) are shown below. The porcine peptide differs by just two amino acid substitutions at positions 18 and 34.

The analogue may include modification by fatty acid addition at an epsilon amino group of at least one lysine residue.

The invention includes $Tyr^1$ glucitol GIP(1-42) having fatty acid addition at an epsilon amino group of at least one lysine residue.

Analogues of GIP(1-42) may have an enhanced capacity to stimulate insulin secretion, enhance glucose disposal, delay glucose absorption or may exhibit enhanced stability in plasma as compared to native GIP. They also may have enhanced resistance to degradation.

Any of these properties will enhance the potency of the analogue as a therapeutic agent.

Analogues having D-amino acid substitutions in the 1, 2 and 3 positions and/or N-glycated, N-alkylated, N-acetylated or N-acylated amino acids in the 1 position are resistant to degradation in vivo.

Various amino acid substitutions at second and third amino terminal residues are included, such as GIP(1-42)$Gly^2$, GIP(1-42)$Ser^2$, GIP(1-42)$Abu^2$, GIP(1-42)$Aib^2$, GIP(1-42)D-$Ala^2$, GIP(1-42)$Sar^2$, and GIP(1-42)$Pro^3$.

Amino-terminally modified GIP analogues include N-glycated GIP(1-42), N-alkylated GIP(1-42), N-acetylated GIP(1-42), N-acetyl-GIP(1-42) and N-isopropyl GIP(1-42).

Other stabilized analogues include those with a peptide isostere bond between amino terminal residues at position 2 and 3. These analogues may be resistant to the plasma enzyme dipeptidyl-peptidase IV (DPP IV) which is largely responsible for inactivation of GIP by removal of the amino-terminal dipeptide $Tyr^1$-$Ala^2$.

In particular embodiments, the invention provides a peptide which is more potent than human or porcine GIP in moderating blood glucose excursions, said peptide consisting of GIP(1-42) or N-terminal fragments of GIP(1-42) consisting of up to between 15 to 30 amino acid residues from the N-terminus (i.e., GIP(1-15) GIP(1-3)) with one or more modifications selected from the group consisting of:

(a) substitution of $Ala^2$ by Gly;
(b) substitution of $Ala^2$ by Ser;
(c) substitution of $Ala^2$ by Abu;
(d) substitution of $Ala^2$ by Aib;
(e) substitution of $Ala^2$ by D-Ala;
(f) substitution of $Ala^2$ by Sar (sarcosine);
(g) substitution of $Glu^3$ by Pro;
(h) modification of $Tyr^1$ by acetylation;
(i) modification of $Tyr^1$ by acylation;
(j) modification of $Tyr^1$ by alkylation;
(k) modification of $Tyr^1$ by glycation;
(l) conversion of $Ala^2$-$Glu^3$ bond to a psi $[CH_2NH]$ bond;
(m) conversion of $Ala^2$-$Glu^3$ bond to a stable peptide isotere bond; and
(n) (n-isopropyl-H) 1GIP.

The invention also provides the use of $Tyr^1$-glucitol GIP in the preparation of a medicament for the treatment of diabetes.

The invention further provides improved pharmaceutical compositions including analogues of GIP with improved pharmacological properties.

Other possible analogues include certain commonly encountered amino acids, which are not encoded by the genetic code, for example, beta-alanine (beta-ala), or other omega-amino acids, such as 3-amino propionic, 4-amino butyric and so forth, ornithine (Orn), citrulline (Cit), homoarginine (Har), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya) and methionine sulfoxide (MSO), substitution of the D form of a neutral or acidic amino acid or the D form of tyrosine for tyrosine.

According to the present invention there is also provided a pharmaceutical composition useful in the treatment of diabetes type II which comprises an effective amount of the peptide as described herein, in admixture with a pharmaceutically acceptable excipient.

The invention also provides a method of N-terminally modifying GIP or analogues thereof the method comprising the steps of synthesizing the peptide from the C terminal to the penultimate N terminal amino acid, adding tyrosine to a bubbler system as a F-moc protected Tyr(tBu)-Wang resin, deprotecting the N-terminus of the tyrosine and reacting with the modifying agent, allowing the reaction to proceed to completion, cleaving the modified tyrosine from the Wang resin and adding the modified tyrosine to the peptide synthesis reaction.

Preferably the agent is glucose, acetic anhydride or pyroglutamic acid.

The invention will now be demonstrated with reference to the following non-limiting examples and the accompanying figures wherein.

BRIEF DESCRIPTION OF THE DRAWINGS

FIG. 1b illustrates degradation of GIP and $Tyr^1$ glucitol GIP by DPP IV.
FIG. 2b illustrates degradation of GIP and $Tyr^1$ glucitol GIP by human plasma.
FIG. 4 shows the effects of GIP and glycated GIP on plasma glucose homeostasis.
FIG. 5 shows effects of GIP on plasma insulin responses.
FIG. 6 illustrates DPP-IV degradation of GIP (1-42).
FIG. 7 illustrates DPP-IV degradation of GIP ($Abu^2$).
FIG. 8 illustrates DPP-IV degradation of GIP ($Sar^2$).
FIG. 9 illustrates DPP-IV degradation of GIP ($Ser^2$).
FIG. 10 illustrates DPP-IV degradation of N-Acetyl-GIP.
FIG. 11 illustrates DPP-IV degradation of glycated GIP.
FIG. 12 illustrates human plasma degradation of GIP.
FIG. 13 illustrates human plasma degradation of GIP ($Abu^2$).
FIG. 14 illustrates human plasma degradation of GIP ($Sar^2$).
FIG. 15 illustrates human plasma degradation of GIP ($Se^2$).
FIG. 16 illustrates human plasma degradation of glycated GIP.
FIG. 17 shows the effects of various concentrations of GIP 1-42 and GIP ($Abu^2$) on insulin release from BRIN-BD11 cells incubated at 5.6 mM glucose.
FIG. 18 shows the effects of various concentrations of GIP 1-42 and GIP ($Abu^2$) on insulin release from BRIN-BD11 cells incubated at 16.7 mM glucose.
FIG. 19 shows the effects of various concentrations of GIP 1-42 and GIP ($Sar^2$) on insulin release from BRIN-BD11 cells incubated at 5.6 mM glucose.
FIG. 20 shows the effects of various concentrations of GIP 1-42 and GIP ($Sar^2$) on insulin release from BRIN-BD11 cells incubated at 16.7 mM glucose.
FIG. 21 shows the effects of various concentrations of GIP 1-42 and GIP ($Ser^2$) on insulin release from BRIN-BD11 cells incubated at 5.6 mM glucose.
FIG. 22 shows the effects of various concentrations of GIP 1-42 and GIP ($Ser^2$) on insulin release from BRIN-BD11 cells incubated at 16.7 mM glucose.
FIG. 23 shows the effects of various concentrations of GIP 1-42 and N-Acetyl-GIP 1-42 on insulin release from BRIN-BD11 cells incubated at 5.6 mM glucose.
FIG. 24 shows the effects of various concentrations of GIP 1-42 and N-Acetyl-GIP 1-42 on insulin release from BRIN-BD11 cells incubated at 16.7 mM glucose.
FIG. 25 shows the effects of various concentrations of GIP 1-42 and glycated GIP 1-42 on insulin release from BRIN-BD11 cells incubated at 5.6 mM glucose.
FIG. 26 shows the effects of various concentrations of GIP 1-42 and glycated GIP 1-42 on insulin release from BRIN-BD11 cells incubated at 16.7 mM glucose.
FIG. 27 shows the effects of various concentrations of GIP 1-42 and GIP ($Gly^2$) on insulin release from BRIN-BD11 cells incubated at 5.6 mM glucose.
FIG. 28 shows the effects of various concentrations of GIP 1-42 and GIP ($Gly^2$) on insulin release from BRIN-BD11 cells incubated at 16.7 mM glucose.
FIG. 29 shows the effects of various concentrations of GIP 1-42 and GIP ($Pro^3$) on insulin release from BRIN-BD11 cells incubated at 5.6 mM glucose.
FIG. 30 shows the effects of various concentrations of CIP 1-42 and GIP ($Pro^3$) on insulin release from BRIN-BD11 cells incubated at 16.7 mM glucose.
FIG. 31a shows the primary structure of human gastric inhibitory polypeptide (GIP) (SEQ ID NO:1),
and FIG. 31b shows the primary structure of porcine gastric inhibitory polypeptide (GIP) (SEQ ID NO:2).

FIGS. 33A-33F are a set of six bar graphs showing the effects of Glu$^3$-substituted forms of GIP and GIP(3-42) on GIP-stimulated insulin secretion in vitro.

FIGS. 34A through 34D are a set of two line graphs (FIGS. 34A, 34C) and two bar graphs (FIGS. 34B, 34D) showing that acute administration of (Pro$^3$)GIP completely antagonises the actions of GIP on glucose tolerance (FIGS. 34A, 34B) and plasma insulin (FIGS. 34C, 34D) responses in obese diabetic ob/ob mice.

FIGS. 35A through 35D are a set of two line graphs (FIGS. 35A, 35C) and two bar graphs (FIGS. 35B, 35D) showing that acute administration of (Pro$^3$)GIP impairs physiological meal-stimulated insulin release and worsens glycemic excursion in obese diabetic ob/ob mice.

FIGS. 37A through 37C are a set of three bar graphs showing that chronic administration of (Pro$^3$)GIP for 11 days decreases glycated $HbA_{1c}$, pancreatic insulin content and associated islet hypertrophy of obese diabetic ob/ob mice.

FIGS. 50A and 50B are a line graph and a bar graph, respectively, showing intracellular cyclic AMP production (FIG. 50A) by GIP (▲) and fatty acid derivatised GIP analogues N-AcGIP(LysPAL$^{16}$) (□) and N-AcGIP(LysPAL$^{37}$) (●), and insulin-releasing activity of glucose (5.6 mmo/l glucose; white bars), GIP (lined bars) and fatty acid derivatised GIP analogues (FIG. 50B) N-AcGIP(LysPAL$^{16}$) (grey bars) and N-AcGIP(LysPAL$^{37}$) (black bars) in the clonal pancreatic beta cell line, BRIN-BD11.

DETAILED DESCRIPTION

Figure 1A:
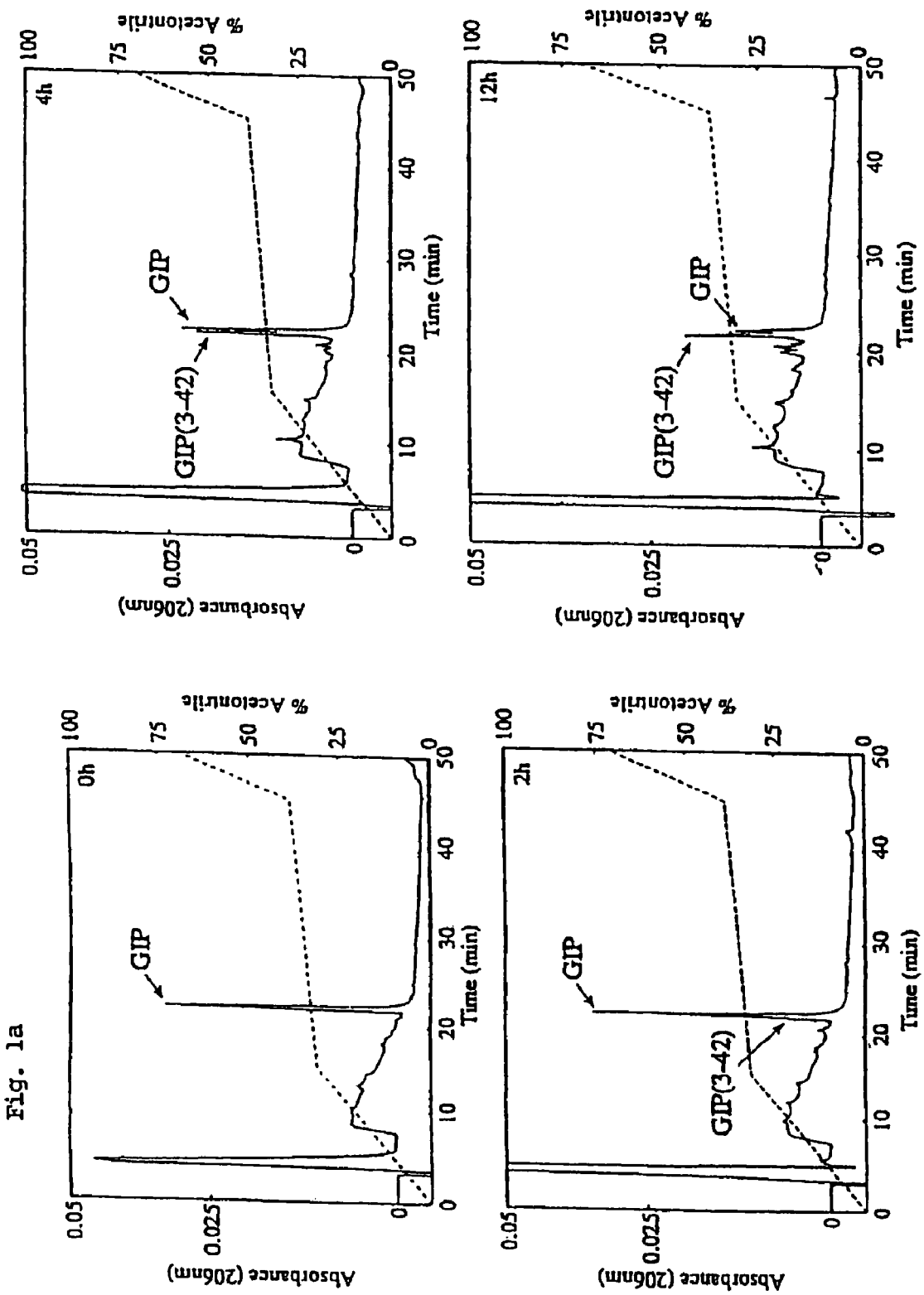
FIG. 1a illustrates degradation of GIP by DPP IV.

The peptide analogues disclosed herein display resistance to degradation by the enzyme DPP IV. These analogues include those with alterations at residues 1, 2 and/or 3 of the native GIP(1-42) peptide, where the alterations interfere with or delay cleavage by DPP IV. The alterations can include chemical modification of one or more of the first three amino acids, such as by acylation, acetylation, alkylation, glycation, conversion of a bond between two amino acids, such as to a psi-[CH$_2$NH] bond, or to a stable isotere bond, or addition of an isopropyl group. The alterations can also include amino acid substitutions at the 1, 2, and/or 3 position, to either a different naturally-occurring amino acid, or an amino acid not encoded by the genetic code. Other alterations are also possible, and the object is to prevent cleavage of the peptide by DPP IV, yet still allow for insulin secretion. This may be accomplished by alterations at other regions of the peptide, such as by alterations that alter the three-dimensional structure to prevent DPP IV cleavage, yet still allow insulin secretion.

Preferred alterations include chemical modifications of residues 1, 2, and 3, amino acid substitutions at residues 1, 2, and 3, and chemical modifications of lysine residues throughout the protein.

Particularly preferred alterations include acetylation of $Tyr^1$ and linkage of a C-16 palmitate group to the epsilon amino group of a lysine residue (especially $Lys^{16}$ or $Lys^{37}$), or substitution of $Glu^3$, especially by proline. The modification can also be the linking of, e.g., a C-8, a C-10, a C-12, a C-14, a C-18 or a C-20 palmitate group to the epsilon amino group of a lysine residue.

It has been found that longer-term, as opposed to acute, GIP receptor antagonism using $Glu^3$-substituted forms of GIP, such as $(Pro^3)$GIP, improve obesity-related insulin resistance and associated glucose intolerance. This has uncovered an unexpected approach to the therapy of obesity, insulin resistance and type 2 diabetes.

As described in Example 1 below, an N-terminally modified version of the GIP protein was prepared, as were analogues of the modified protein. The protein and its analogues were then evaluated in Example 2 for their antihyperglycemic and insulin-releasing properties in vivo, and were found to exhibit a substantial resistance to amino peptidase degradation and increased glucose lowering activity relative to native GIP.

The 42 amino acid GIP is an important incretin hormone released into the circulation from endocrine K-cells of the duodenum and jejunum following ingestion of food. The high degree of structural conservation of GIP among species supports the view that this peptide plays an important role in metabolism. Secretion of GIP is stimulated directly by actively transported nutrients in the gut lumen without a notable input from autonomic nerves. The most important stimulants of GIP release are simple sugars and unsaturated long chain fatty acids, with amino acids exerting weaker effects. As with tGLP-1, the insulin-releasing effect of GIP is strictly glucose-dependent. This affords protection against hypoglycemia and thereby fulfills one of the most desirable features of any current or potentially new antidiabetic drug.

The present results demonstrate for the first time that $Tyr^1$-glucitol GIP displays profound resistance to serum and DPP IV degradation. Using ESI-MS the present study showed that native GIP was rapidly cleaved in vitro to a major 4748.4 Da degradation product corresponding to GIP(3-42), which confirmed previous findings using matrix-assisted laser desorption ionization time-of-flight mass spectrometry. Serum degradation was completely inhibited by diprotin A (Ile-Pro-Ile), a specific competitive inhibitor of DPP IV, confirming this as the main enzyme for GIP inactivation in vivo. In contrast, $Tyr^1$-glucitol GIP remained almost completely intact after incubation with serum or DPP IV for up to 12 hours. This indicates that glycation of GIP at the amino-terminal $Tyr^1$ residue masks the potential cleavage site from DPP IV and prevents removal of the $Tyr^1$-$Ala^2$ dipeptide from the N-terminus preventing the formation of GIP(3-42).

Consistent with in vitro protection against DPP IV, administration of $Tyr^1$-glucitol GIP significantly enhanced the antihyperglycemic activity and insulin-releasing action of the peptide when administered with glucose to rats. Native GIP enhanced insulin release and reduced the glycemic excursion as observed in many previous studies. However, amino-terminal glycation of GIP increased the insulin-releasing and antihyperglycemic actions of the peptide by 62% and 38% respectively, as estimated from insulin area under the curve (AUC) measurements. Detailed kinetic analysis is difficult due to necessary limitation of sampling times, but the greater insulin concentrations following $Tyr^1$-glucitol GIP as opposed to GIP at 30 minutes post-injection is indicative of a longer half-life. The glycemic rise was modest in both peptide-treated groups and glucose concentrations following injection of $Tyr^1$-glucitol GIP were consistently lower than after GIP. Since the insulinotropic actions of GIP are glucose-dependent, it is likely that the relative insulin-releasing potency of $Tyr^1$-glucitol GIP is greatly underestimated in the present in vivo experiments.

In vitro studies in the laboratory of the present inventors using glucose-responsive clonal B-cells showed that the insulin-releasing potency of $Tyr^1$ glucitol GIP was several orders of magnitude greater than GIP and that its effectiveness was more sensitive to change of glucose concentrations within the physiological range. Together with the present in vivo observations, this suggests that N-terminal glycation of GIP confers resistance to DPP IV degradation whilst enhancing receptor binding and insulin secretory effects on the B-cell. These attributes of $Tyr^1$-glucitol GIP are fully expressed in vivo where DPP IV resistance impedes degradation of the peptide to GIP(3-42), thereby prolonging the half-life and enhancing effective concentrations of the intact biologically active peptide. It is thus possible that glycated GIP is enhancing insulin secretion in vivo both by enhanced potency at the receptor as well as improving DPP IV resistance. Thus numerous studies have shown that GIP (3-42) and other N-terminally modified fragments, including GIP(4-42), and GIP(17-42) are either weakly effective or inactive in stimulating insulin release. Furthermore, evidence exists that N-terminal deletions of GIP result in receptor antagonist properties in GIP receptor transfected Chinese hamster kidney cells [9], suggesting that inhibition of GIP catabolism would also reduce the possible feedback antagonism at the receptor level by the truncated GIP(3-42).

In addition to its insulinotopic actions, a number of other potentially important extrapancreatic actions of GIP may contribute to the enhanced antihyperglycemic activity and other beneficial metabolic effects of $Tyr^1$-glucitol GIP. These include the stimulation of glucose uptake in adipocytes, increased synthesis of fatty acids and activation of lipoprotein lipase in adipose tissue. GIP also promotes plasma triglyceride clearance in response to oral fat loading. In liver, GIP has been shown to enhance insulin-dependent inhibition of glycogenolysis. GIP also reduces both glucagon-stimulated lipolysis in adipose tissue as well as hepatic glucose production. Finally, recent findings indicate that GIP has a potent effect on glucose uptake and metabolism in mouse isolated diaphragm muscle. This latter action may be shared with tGLP-1 and both peptides have additional benefits of stimulating somatostatin secretion and slowing down gastric emptying and nutrient absorption.

This study demonstrates that the glycation of GIP at the aminoterminal $Tyr^1$ residue limits GIP catabolism through impairment of the proteolytic actions of serum peptidases and thus prolongs its half-life in vivo. This effect is accompanied by enhanced antihyperglycemic activity and raised insulin concentrations in vivo, suggesting that such DPP IV resistant analogues are potentially useful therapeutic agents for NIDDM. $Tyr^1$-glucitol GIP appears to be particularly interesting in this regard since such amino-terminal modification of GIP enhances rather than impairs glucose-dependent insulinotropic potency as was observed recently for tGLP-1.

As shown in Table 1 in Example 3, glycated GIP, acetylated GIP, GIP(Ser$^2$) are GIP(Abu$^2$) more resistant than native GIP to in vitro degradation with DPP IV. From these data GIP (Sar$^2$) appears to be less resistant. As shown in Table 2, all analogues tested exhibited resistance to plasma degradation, including GIP(Sar$^2$) which from DPP IV data appeared least resistant of the peptides tested. DPA substantially inhibited degradation of GIP and all analogues tested with complete abolition of degradation in the cases of GIP(Abu$^2$), GIP(Ser$^2$) and glycated GIP. This indicates that DPP IV is a key factor in the in vivo degradation of GIP.

As shown in FIGS. 17-30, the glycated GIP analogue exhibited a considerably greater insulinotropic response relative to native GIP. N-terminal acetylated GIP exhibited a similar pattern and the GIP(Ser$^2$) analogue also evoked a strong response. From these tests, GIP(Gly$^2$) and GIP(Pro$^3$) appeared to the least potent analogues in terms of insulin release. Other stable analogues tested, namely GIP(Abu$^2$) and GIP(Sar$^2$), exhibited a complex pattern of responsiveness dependent on glucose concentration and dose employed. Thus, very low concentrations were extremely potent under hyperglycemic conditions (16.7 mM glucose). This suggests that even these analogues may prove therapeutically useful in the treatment of type 2 diabetes where insulinotropic capacity combined with in vivo degradation dictates peptide potency.

A major limitation to the possible therapeutic use of both GIP and GLP-1 as insulin-releasing agents for the treatment of diabetes is their rapid degradation in vivo by dipeptidylpeptidase-IV (DPP-IV; EC 3.4.14.5). This enzyme rapidly removes the amino-terminal dipeptide from the two peptides producing GIP(3-42) and GLP-1(9-36), which lack biological activity (Gault, V. A. et al., 2002, *Biochem. Biophys. Res. Commun.* 290:1420-1426). In searching for stable amino-terminally modified forms of GIP and GLP-1, it was discovered that a novel synthetic GIP analogue with a single proline substitution at position 3 close to the cleavage site, (Pro$^3$)GIP, functioned as a potent GIP receptor antagonist.

As shown in Example 4, below, (Pro$^3$)GIP, other Glu$^3$-substituted forms of GIP and GIP(3-42) are potent GIP receptor antagonists both in vitro and in vivo. Experiments evaluating the effects of chronic GIP receptor antagonism in normal mice using (Pro$^3$)GIP demonstrated a substantial but reversible deterioration of glucose tolerance. This is entirely consistent with the widely recognised physiological role of GIP as an important insulin-releasing intestinal hormone involved in the regulation of glucose disposal following feeding (Meier, J. J. et al., 2002, *Regul. Pept.* 107:1-13).

Most notably, and in complete contrast to normal mice, the experiments disclosed herein show that chronic (Pro$^3$)GIP administration to obese diabetic ob/ob mice for 11 days does not worsen glucose intolerance and diabetes status at all. Surprisingly, GIP receptor antagonism in this obese insulin resistant model was associated with highly substantial improvements of glycated HbA$_{1c}$, plasma glucose and insulin concentrations, glucose tolerance and insulin sensitivity. Pancreatic insulin content was also decreased and the characteristic islet hypertrophy of the obese mutant was partially reversed. These latter observations indicate a decreased secretory demand for endogenous insulin following (Pro$^3$) GIP as a result of improved insulin resistance.

Indeed, insulin sensitivity tests conducted in ob/ob mice 11 days into (Pro$^3$)GIP treatment revealed a substantial improvement in tissue insulin insensitivity, which more than compensated for the functional ablation of the insulin-releasing GIP component of the enteroinsular axis. The exact mechanism responsible for this effect on insulin sensitivity is unknown but ablation of direct action of circulating GIP on adipose tissue metabolism is a likely candidate. Also noteworthy was the fact that all these beneficial actions of (Pro$^3$)GIP in obese diabetic ob/ob mice were reversed within 9 days cessation of treatment.

These results clearly indicate that (Pro$^3$)GIP and other analogues based on Glu$^3$-substituted or N-terminally truncated forms of the gastrointestinal hormone GIP can offer an important therapeutic means of alleviating insulin resistance for the treatment of obesity, the so-called insulin resistant (metabolic) syndrome and type 2 diabetes in humans.

Some studies have attempted to enhance incretin action using DPP IV inhibitors or stable analogs of GLP-1 and GIP for the treatment of type 2 diabetes (Green, B. D. et al., 2004, *Curr. Pharm. Des.* 10: In Press; Drucker, D. J. et al., *Diabetes Care* 10:2929-2940). Such an approach is reliant on the possibility that incretin action is defective in diabetes and that the underlying defects responsible for metabolic disarray might be over-ridden by exogenous GLP-1 or GIP administration. There is some evidence for a beneficial and possibly therapeutic role of both GLP-1 and GIP analogs in diabetes (Meier, J. J. et al., 2002, *Regul. Pept.* 107:1-13; Gault, V. A. et al., 2003, *Biochem Biophys Res Commun* 308:207-213; Holst, J. J. et al., 2004, *Am. J. Physiol. Endocrinol. Metab.* 287:E199-E206; Green, B. D. et al., 2004, *Curr. Pharm. Des.* 10: In Press; Drucker, D. J. et al., *Diabetes Care* 10:2929-2940). Nevertheless, understanding of the possible involvement of incretin hormones in the pathophysiology of diabetes is lacking, partly due to cross-reaction of classical GLP-1 and GIP radioimmunoassays with the predominant DPP IV-generated truncated peptide forms, GLP-1(9-36) and GIP(3-42), which circulate at particularly high concentrations (Meier, J. J. et al., 2002, *Regul. Pept.* 107:1-13). Some clinical studies seems to suggest existence of a defect in the secretion of GLP-1 and a defect in the action of GIP in type 2 diabetes (Holst, J. J. et al., 2004, *Am. J. Physiol. Endocrinol. Metab.* 287:E199-E206). However, the basis for such a conclusion is not impressive given the many previous contradictory human studies (Morgan, L. M., "Insulin secretion and the enteroinsular axis," In: *Nutrient regulation of insulin secretion*, Flatt, P. R., ed., London, Portland Press, 1992, p. 1-22), and the likelihood that the reported insensitivity of pancreatic beta cells to GIP (Vilsboll, T. et al., 2002, *Diabetologia* 45:1111-1119) may reflect a generalized secretory dysfunction rather than a specific cellular defect (Meier, J. J. et al., 2003, *Metabolism* 52:1579-1585). Indeed, the insulin secretory response to all secretagogues, including GLP-1 is compromised in type 2 diabetes (Kjems, L. L. et al., 2003, *Diabetes* 52:380-386; Flatt, P. R. et al., "Defective insulin secretion in diabetes and insulinoma," in *Nutrient regulation of insulin secretion*, Flatt P. R., ed. London, Portland Press, 1992, p. 341-386). Thus the proposed use of GLP-1 and GIP for diabetes therapy is reliant on peptide engineering to provide analogs of incretin hormones with improved potency due to DPP IV resistance, decreased renal clearance and/or enhanced GIP receptor and post-receptor activity (Gault, V. A. et al., 2003, *Biochem Biophys Res Commun* 308:207-213).

Although no single animal model can match the complex etiology of type 2 diabetes in man, studies of the ob/ob syndrome in mice have highlighted notable abnormalities of GIP in relation to the interplay between hyperphagia, hyperinsulinemia and the metabolic demise associated with progressive obesity-diabetes (Flatt, P. R. et al., 1983, *Diabetes* 32:433-435; Flatt, P. R. et al., 1984, *J. Endocrinol.* 101:249-256; Bailey, C. J. et al., 1986, *Acta Endocrinol.* (Copenh) 112:224-229). These animals constitute a model of non-insulin dependent diabetes associated with gross obesity and severe insulin resistance, driven by leptin deficiency (Bailey, C. J. et al., "Animal syndromes resembling type 2 diabetes," in *Textbook of Diabetes*, 3rd ed. Pickup J. C. & Williams G., eds. Oxford, Blackwell Science Ltd., 2003, p. 25.1-25.30). Furthermore, recent research suggests an interaction between leptin and the enteroinsular axis (Anini, Y. et al., 2003, *Diabetes* 52:252-259) and that over-stimulation of the GIP receptor ("GIP-R") on adipocytes appears to be an important contributor to fat deposition in ob/ob mice (Miyawaki, K. et al., 2002, *Nat. Med* 8:738-742).

As shown in Example 5, below, daily injections of the stable and specific GIP-R antagonist, (Pro$^3$)GIP can be used to chemically ablate the GIP-R and evaluate the role of endogenous circulating GIP in obesity-diabetes as manifested in ob/ob mice. The results reveal a cardinal role for GIP in insulin resistance and associated metabolic disturbances, and provide the first experimental evidence that GIP-R antagonists might provide a novel and effective means of treating obesity-driven forms of type 2 diabetes.

Knock-out of the GIP-R in normal mice has been shown to result in significant impairment of glucose tolerance and meal-induced insulin secretion without appreciable effects on food intake, body weight or basal glucose or insulin concentrations (Miyawaki, K. et al., 1999, *Proc. Nat. Acad. Sci. USA* 96:14843-14847). More recent studies with genetic GIP-R knockout mice have corroborated these findings and additionally shown that GIP has a significant involvement in the enteroinsular axis (Pederson, R. A. et al., 1998, *Diabetes* 47:1046-1052; Pamir, N. et al., 2003, *Am. J. Physiol. Endocrinol. Metab.* 284:E931-939). However, double knockout of receptors for GLP-1 and GIP results in a surprisingly modest deterioration of glucose homeostasis (Hansotia, T., et al., 2004, *Diabetes* 53:1326-1335; Preitner, F., et al., 2004, *J. Clin. Invest.* 113:635-645), indicating possible up-regulation of compensatory mechanisms during life-long deletion of GLP-1 and GIP receptors.

The analogue (Pro$^3$)GIP can be used as a specific and potent antagonist of the GIP-R that is highly stable and resistant to DPP IV-mediated degradation (Gault, V. A. et al., 2002, *Biochem. Biophys. Res. Commun.* 290:1420-1426). Using (Pro$^3$)GIP acutely, the results disclosed herein highlight the involvement of GIP in the plasma insulin response to feeding and the enteroinsular axis of ob/ob mice (Gault, V. A. et al., 2003, *Diabetologia* 46:222-230). Comparison with the effects of the GLP-1-R antagonist, exendin(9-39), indicates that GIP contributes substantially to the insulin releasing actions of the enteroinsular axis and represents the major physiological incretin (Gault, V. A. et al., 2003, *Diabetologia* 46:222-230). Once daily administration of (Pro$^3$)GIP to normal mice for 11 days results in the reversible impairment of glucose tolerance associated with decreased insulin sensitivity (Irwin, N., 2004, *Biol. Chem.* 385:845-852). Basal and postprandial insulin secretion together with pancreatic insulin content and islet morphology were unchanged. Thus longer-term chemical ablation of GIP-R function with daily (Pro$^3$)GIP can mimic the phenotype induced by genetic GIP-R knockout in mice with the exception of revealing a potentially important additional effect of endogenous GIP on insulin action, which appears to be independent of enhanced insulin secretion.

Far from reproducing this predicted scenario and the metabolic deterioration observed following genetic or chemical knockout of the GIP-R in normal mice (Miyawaki, K. et al., 1999, *Proc. Nat. Acad. Sci. USA* 96:14843-14847; Irwin, N., 2004, *Biol. Chem.* 385:845-852), ob/ob mice treated with daily (Pro$^3$)GIP for 11 days exhibited a marked improvement in diabetic status. This included decreased fasting and basal hyperglycemia, lowered glycated hemoglobin, improved glucose tolerance and a significantly diminished glycemic excursion following feeding. Notably, basal and glucose-stimulated plasma insulin concentrations were decreased, suggesting that insulin sensitivity must have improved significantly following (Pro$^3$)GIP in order to restrain the hyperglycemia. Indeed, insulin sensitivity tests conducted after 11 days of (Pro$^3$)GIP administration revealed a 57% increase in the glucose-lowering action of exogenous insulin. Bearing in mind that the severity of the ob/ob syndrome represents a tough test for current antidiabetic drugs, including insulin, sulfonylureas, metformin and thiazolidenediones (Flatt, P. R. et al., "Defective insulin secretion in diabetes and insulinoma," in *Nutrient regulation of insulin secretion*, Flatt P. R., ed. London, Portland Press, 1992, p. 341-386; Stevenson, R. W. et al., 1995, *The Diabetes Annual* 9:175-191; Wiemsperger, N. F., "Preclinical pharmacology of biguanides," *Handbook of Experimental Pharmacology* 119:305-358, 1996), induction of such rapid and reversible changes by GIP-R blockade using (Pro$^3$)GIP is unprecedented.

It is important to note that the above effects were observed independently of any change in food intake or body weight in (Pro$^3$)GIP treated ob/ob mice. This accords with the view that endogenous GIP lacks effects on feeding activity (Meier, J. J. et al., 2002, *Regul. Pept.* 107:1-13). However, the observation on body weight contrasts with findings in ob/ob mice crossbred to genetically knockout GIP-R function (Miyawaki, K. et al., 2002, *Nat. Med.* 8:738-742). Thus in these transgenic mice, life-long depletion of GIP-R function was associated with decreased body weight gain and significant amelioration of both adiposity and insulin resistance compared with control (Lep$^{ob}$/Lep$^{ob}$) mice (Miyawaki, K. et al., 2002, *Nat. Med.* 8:738-742). In this previous study, the improvement of insulin sensitivity may have been a simple consequence of reduced adipose tissue mass as this would significantly enhance peripheral glucose disposal (Bailey, C. J. et al., "Animal syndromes resembling type 2 diabetes," in *Textbook of Diabetes*, 3rd ed. Pickup J. C. & Williams G., eds. Oxford, Blackwell Science Ltd., 2003, p. 25.1-25.30). However, the present results observed in rapid time and without effects on feeding or body weight clearly indicate the involvement of an alternative mechanism.

Figure 49:
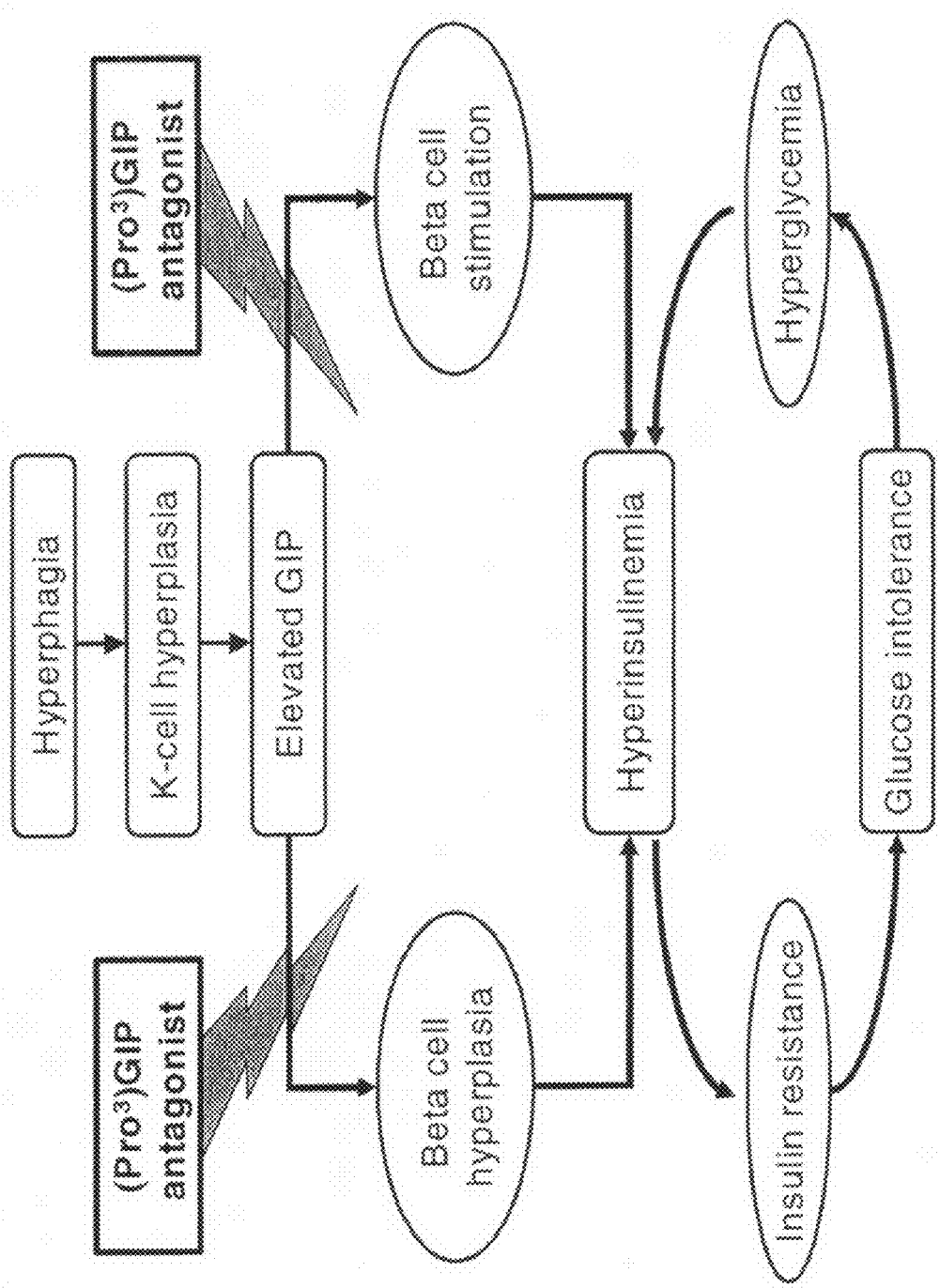
FIG. 49 is an illustration of how the GIP receptor ("GIP-R") antagonist, (Pro$^3$)GIP, counters beta cell hyperplasia, hyperinsulinemia and insulin resistance lead to improved glucose intolerance and diabetes control.

The most plausible explanation for the present data stem from appreciation of the key milestones in the age-dependent progression of the ob/ob syndrome on the Aston background as depicted in FIG. 49, which is an illustration of how the GIP-R antagonist, (Pro$^3$)GIP, counters beta cell hyperplasia, hyperinsulinemia and insulin resistance lead to improved glucose intolerance and diabetes control. Possible longer-term direct actions of GIP on adipocyte function and fat stores, suggested by studies in GIP-R knockout ob/ob mice have been omitted.

Figure 48:
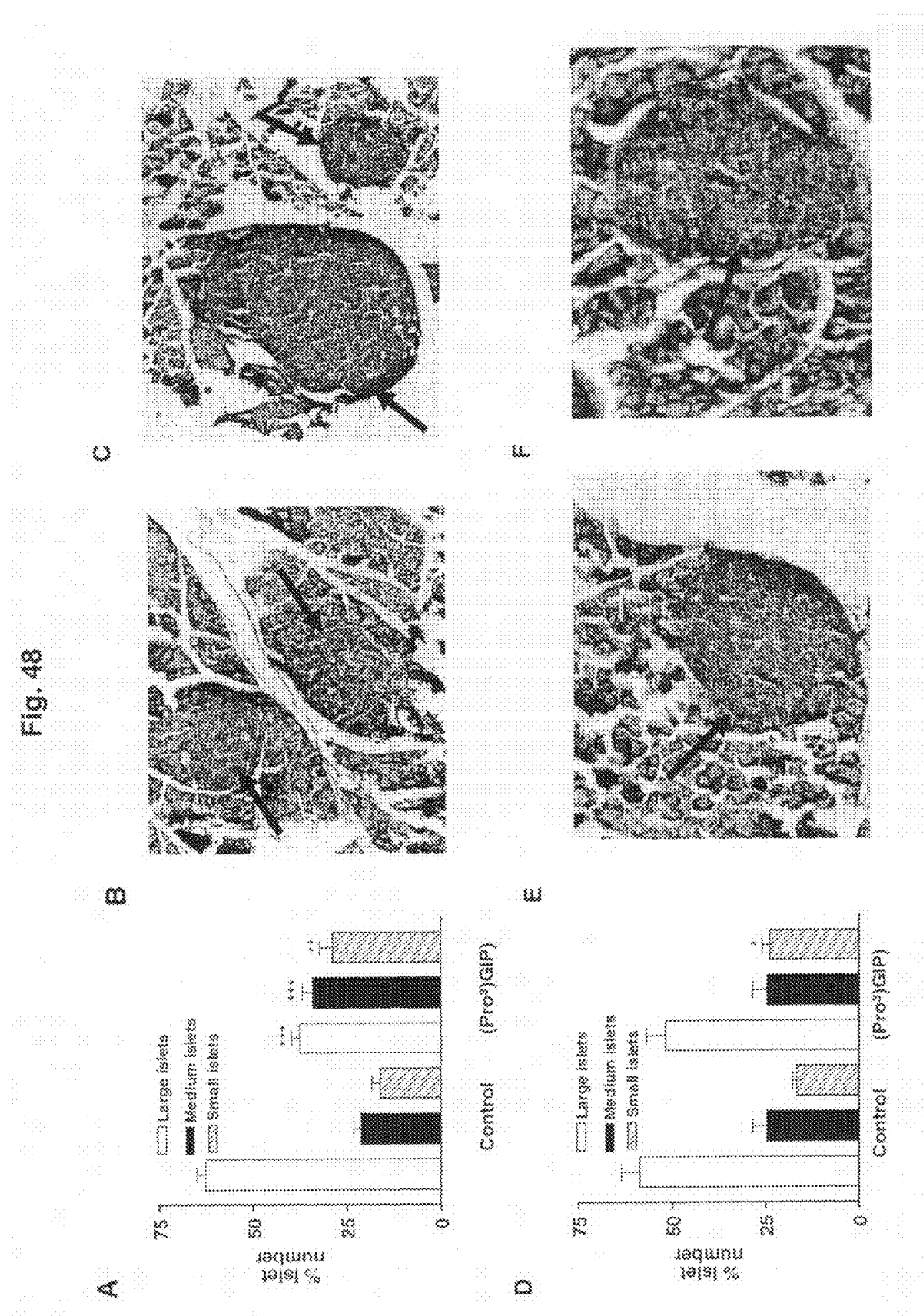
FIGS. 48A through 48F are a set of two bar graphs (FIGS. 48A, 48D) and four photomicrographs (FIGS. 48B, 48C, 48E, 48F), showing the effects of daily (Pro$^3$)GIP administration on islet size and morphology in ob/ob)mice.

Due to double recessive ob mutation and resulting leptin deficiency, young ob/ob mice develop a profound early hyperphagia (Bailey, C. J., et al., 1982, *Int. J. Obes.* 6:11-21). Substantial enteroendocrine stimulation results in K-cell hyperplasia and markedly elevated concentrations of intestinal and circulating GIP (Flatt, P. R. et al., 1983, *Diabetes* 32:433-435; Flatt, P. R. et al., 1984, *J. Endocrinol.* 101:249-256; Bailey, C. J. et al., 1986, *Acta Endocrinol.* (Copenh) 112:224-229). This in turn promotes islet hypertrophy and beta cell hyperplasia (Bailey, C. J., et al., 1982, *Int. J. Obes.* 6:11-21) together with marked hyperinsulinemia and mounting insulin resistance (Flatt, P. R., et al., 1981, *Horm Metab Res* 13:556-560). This process manifests itself in terms of rising basal hyperglycemia and glucose intolerance. A vicious spiral is thus established wherein beta cell compensation results in marked hyperinsulinemia which attempts to moderate increasing insulin resistance (Bailey, C. J., et al., 1982, *Int. J. Obes.* 6:11-21; Flatt, P. R., et al., 1981, *Horm Metab Res* 13:556-560). Viewed in this context, it is clear that chemical ablation of GIP-R function with daily (Pro$^3$)GIP will decrease beta cell stimulation and hyperinsulinemia. However, instead of causing further impairment of glucose homeostasis, a preferentially marked improvement of insulin sensitivity results in a substantial improvement of the metabolic syndrome. Further support for this scenario, is the partial amelioration of islet hypertrophy and beta cell hyperplasia in (Pro$^3$)GIP treated ob/ob mice (FIG. 48). Notably, average islet diameter was diminished with the largest islets (>15 mm) being replaced by a greater proportion with small or medium diameters (0.1-15 mm). These effects were largely reversed by 9 day cessation of treatment, supporting the idea of active islet and beta cell growth in adult ob/ob mice (Bailey, C. J., et al., 1982, *Int. J. Obes.* 6:11-21). Recent observations indicate that GIP acts as a mitotic stimulus and anti-apoptotic agent to the beta cell (Pospisilik, J. A. et al., 2003, *Diabetes* 52:741-750; Trumper, A. et al., 2001, *Mol. Endocrinol.* 15:1559-1570; Ehses, J. A. et al., 2003, *Endocrinology* 144: 4433-4445, Trumper, A. et al., 2002, *J. Endocrinol.* 174:233-246). Thus, it is believed that negative effects of (Pro$^3$)GIP on islet size reflects a combination of decreased proliferation and increased apoptosis of beta cells.

The results shown in Example 5 have demonstrated for the first time that daily administration of the GIP-R antagonist, (Pro$^3$)GIP, improves glucose tolerance and ameliorates insulin resistance and abnormalities of islet structure and function in ob/ob mice. Notably, these effects were reversed by discontinuation of (Pro$^3$)GIP for 9 days. Freedom from any obvious side effects also accords with earlier observations in normal mice (Irwin, N., 2004, *Biol. Chem.* 385:845-852) and mice genetically engineered with life-long GIP-R deficiency (Miyawaki, K. et al., 2002, *Nat. Med.* 8:738-742). The present observations point to a cardinal role of endogenous GIP in the pathogenesis of obese-insulin resistant-diabetes. More importantly, the data indicate that GIP-R antagonists, such as (Pro$^3$)GIP, provide a novel, physiological and effective means to treat obese type 2 diabetes through the alleviation of insulin resistance.

In Example 6, fatty acid derivatisation was used to develop two novel long-acting, N-terminally modified GIP analogues (N-AcGIP(LysPAL$^{16}$) and N-AcGIP(LysPAL$^{37}$)).

Degradation studies were carried out with dipeptidylpeptidase IV (DPP IV). Cyclic AMP production was assessed using GIP receptor transfected CHL fibroblasts. In vitro insulin release was assessed in BRIN-BD11 cells. Insulinotropic and glycaemic responses to acute and long-term peptide administration were evaluated in obese diabetic (ob/ob) mice.

In contrast to GIP both analogues displayed resistance to DPP IV degradation. The analogues also stimulated cyclic AMP production and exhibited significantly improved in vitro insulin secretion compared to control. Administration of N-AcGIP(LysPAL$^{16}$) or N-AcGIP(LysPAL$^{37}$) together with glucose in ob/ob mice significantly reduced the glycaemic excursion and improved the insulinotropic response compared to GIP. Dose-response studies with N-AcGIP(LysPAL$^{37}$) revealed highly significant decreases in the overall glycaemic excursion and increases in circulating insulin even with 6.25 nmoles/kg. Once daily injection of ob/ob mice with N-AcGIP(LysPAL$^{37}$) over 14 days significantly decreased plasma glucose, glycated haemoglobin and improved glucose tolerance compared with saline or native GIP. Plasma and pancreatic insulin were significantly increased, together with a significant enhancement in the insulin response to glucose and a notable improvement of insulin sensitivity. No evidence was found for GIP-receptor desensitization and the metabolic effects of N-AcGIP(LysPAL$^{37}$) were independent of any change in feeding or body weight.

These results show that novel fatty acid derivatised, N-terminally modified analogues of GIP such as N-AcGIP(LysPAL$^{37}$), may have significant potential for the treatment of type 2 diabetes.

One approach to counter both renal clearance and enzyme degradation of GIP concerns the utilisation of fatty acid derivatisation together with N-terminal modification. Fatty acid derivatisation has previously been shown to prolong the half-life of insulin (Kurtzhals, P. et al., 1995, *Biochem. J.* 312: 725-731) and the sister incretin glucagon-like peptide-1 (GLP-1) (Knudsen, L. B. et al., 2000, *J. Med. Chem.* 43: 1664-1669; Green, B. D. et al., 2004, *Biol. Chem.* 385: 169-177; Kim, J. G. et al., 2003, *Diabetes* 52: 751-759). A number of N-terminally modified GIP analogues have been developed which exhibit profound resistance to DPP IV (Hinke, S. A. et al., 2002, *Diabetes* 51: 656-661; Gault, V. A. et al., 2002, *Biochem. J.* 367: 913-920; Gault, V. A. et al., 2003, *J. Endocrinol.* 176: 133-141; O'Harte, F. P. M. et al., 1999, *Diabetes* 48: 758-765). Several of these, most notably those modified at Tyr$^1$ of GIP with an addition of an acetyl, glucitol, pyroglutamyl or Fmoc adduct, exhibit enhanced activity at the GIP receptor in vitro (Gault, V. A. et al., 2002, *Biochem. J.* 367: 913-920; O'Harte, F. P. M. et al., 1999, *Diabetes* 48: 758-765; O'Harte, F. P. M. et al., 2002, *Diabetologia* 45: 1281-1291). As a result of degradation resistance and enhanced cellular activity, these analogues display enhanced and protracted antihyperglycaemic and insulin-releasing activity when administered acutely to animals with obesity-diabetes (Hinke, S. A. et al., 2002, *Diabetes* 51: 656-661; Gault, V. A. et al., 2002, *Biochem. J.* 367: 913-920; Gault, V. A. et al., 2003, *J. Endocrinol.* 176: 133-141; O'Harte, F. P. M. et al., 1999, *Diabetes* 48: 758-765; O'Harte, F. P. M. et al., 2002, *Diabetologia* 45: 1281-1291). Of these, N-AcGIP has emerged as the most effective DPP IV-resistant analogue, substantially augmenting the plasma insulin response and curtailing the glycaemic excursion following conjoint administration with glucose to ob/ob mice (O'Harte, F. P. M. et al., 2002, *Diabetologia* 45: 1281-1291).

Example 6 was designed to evaluate the metabolic stability, biological activity and antidiabetic potential of novel second generation fatty acid derivatised, N-terminally modified N-AcGIP analogues, N-AcGIP(LysPAL$^{16}$) and N-AcGIP (LysPAL$^{37}$). Both GIP analogues contain a C-16 palmitate group linked to the epsilon-amino group of Lys at positions 16 or 37, in combination with an N-terminal (Tyr$^1$) acetyl group (O'Harte, F. P. M. et al., 2002, *Diabetologia* 45: 1281-1291). The relative stability to DPP IV degradation, insulin secretion and cyclic AMP properties were examined in vitro together with acute and dose-response studies in obese diabetic ob/ob mice. The most effective analogue, N-AcGIP(LysPAL$^{37}$) was administered to ob/ob mice by once daily intraperitoneal injection for 14 days prior to evaluation of glucose homeostasis, pancreatic beta cell function and insulin sensitivity. Possible desensitization of GIP receptor action by prolonged exposure to elevated concentrations of N-AcGIP(LysPAL$^{37}$) was also examined. The results indicate the particular promise of the novel second generation N-terminally acetylated GIP analogue, N-AcGIP(LysPAL$^{37}$), as a potential therapeutic agent for the treatment of type 2 diabetes.

Despite their many attributes, DPP IV-resistant analogues of GIP and GLP-1, like their native counterparts, are still subject to renal filtration. To circumvent this problem, fatty acid derivatisation has been used to improve the duration of action of GLP-1 (Knudsen, L. B. et al., 2000, *J. Med. Chem.* 43: 1664-1669; Green, B. D. et al., 2004, *Biol. Chem.* 385: 169-177; Kim, J. G. et al., 2003, *Diabetes* 52: 751-759). The most promising analogue, NN2211 (Liraglutide), appears effective in improving blood glucose control in type 2 diabetic subjects despite a tendency towards promotion of nausea possibly due to slowing of gastric emptying (Agerso, H. et al., 2002, *Diabetologia* 45: 195-202).

Example 6 describes the results of introducing two specific modifications to the native GIP hormone, namely N-terminal acetylation and C-terminal fatty acid derivatisation. N-terminal acetylation was employed, as previously described (O'Harte, F. P. M. et al., 2002, *Diabetologia* 45: 1281-1291), to significantly enhance stability to DPP IV. In contrast, conjugation of a C-16 palmitate residue at the epsilon-amino group of $Lys^{16}$ or $Lys^{37}$ was introduced to extend the biological half-life through binding to circulating proteins (Kurtzhals, P. et al., 1995, *Biochem. J.* 312: 725-731). Unlike the native peptide, both GIP analogues appeared to be completely resistant to enzymatic breakdown by DPP IV, which corroborates previous observations with N-AcGIP (O'Harte, F. P. M. et al., 2002, *Diabetologia* 45: 1281-1291). Furthermore, both analogues displayed similar or slightly better insulin-releasing and cyclic AMP generating properties to native GIP and N-AcGIP when tested in the in vitro cellular systems (O'Harte, F. P. M. et al., 2002, *Diabetologia* 45: 1281-1291).

To assess the antihyperglycaemic and insulinotropic potential of the fatty acid derivatised GIP analogues in vivo, obese diabetic (ob/ob) mice were employed. The ob/ob syndrome is an extensively studied model of spontaneous obesity and diabetes, exhibiting hyperphagia, marked obesity, moderate hyperglycaemia and severe hyperinsulinemia (Bailey, C. J. et al., 1982, *Int. J. Obesity* 6: 11-21). As described in previous studies (Gault, V. A. et al., 2002, *Biochem. J.* 367: 913-920; Gault, V. A. et al., 2003, *J. Endocrinol.* 176: 133-141), native GIP only modestly reduced the glycaemic excursion in ob/ob mice reflecting the severe insulin resistance of this mutant animal model (Bailey, C. J. et al., 1982, *Int. J. Obesity* 6: 11-21). In sharp contrast, both N-acetylated GIP analogues additionally substituted with a palmitate molecule at $Lys^{16}$ or $Lys^{37}$ (N-AcGIP($LysPAL^{16}$) and N-AcGIP($LysPAL^{37}$)) significantly lowered plasma glucose levels compared to the native peptide. This was accompanied by significantly enhanced insulin-releasing activity, especially in the case of N-AcGIP($LysPAL^{37}$). The significantly protracted insulinotropic response to both fatty acid derivatised GIP analogues at 60 minutes despite substantially lower plasma glucose is indicative of an extended plasma half-life. This may be due to binding of both palmitate derivatised GIP analogues to serum albumin, therefore significantly impairing their clearance via the kidneys (Meier, J. J. et al., 2004, *Diabetes* 53: 654-662). However, further studies including establishment of sensitive and specific immunoassays for the novel GIP analogues would be needed to confirm such actions.

N-AcGIP($LysPAL^{37}$) appeared to be the best fatty acid derivatised analogue displaying a more protracted, significantly enhanced insulin-releasing potency over N-AcGIP ($LysPAL^{16}$) in vivo. Reasons for the increased potency of N-AcGIP($LysPAL^{37}$) remain unclear, but one explanation is an extended half-life. Another possibility may be that a fatty acid chain linked to the Lys closer to the C-terminus of the peptide may have less of a detrimental effect upon the bioactive region of the molecule known to be located within the N-terminus (Gault, V. A. et al., 2002, *Biosci. Rep.* 22: 523-528; Hinke, S. A. et al., 2001, *Biochim. Biophys. Acta* 1547: 143-55; Manhart, S. et al., 2003, *Biochemistry* 42: 3081-3088). However, similarities between the in vitro biological activities of the two palmitate substituted analogues make this less likely.

Given that N-AcGIP($LysPAL^{37}$) was the more potent of the two analogues in vivo, it was further utilised in dose-response studies. Considering that native GIP itself has only very modest effects in ob/ob mice, as sometimes observed with type 2 diabetic subjects (Nauck, M. A. et al., 1993, *J. Clin. Invest.* 91: 301-307; Meier, J. J. et al., 2004, *Diabetes* 53: 220-224; Vilsbøll, T. et al., 2002, *Diabetologia* 45: 1111-1119), it is remarkable that N-AcGIP($LysPAL^{37}$), even at the lowest dose of 6.25 nmoles/kg, exhibited significant glucose-lowering and insulinotropic activity when administered with glucose. Considering N-AcGIP($LysPAL^{37}$) is subject to albumin binding, the fact that it is still highly biologically active even at lower concentrations indicates striking potency.

Daily administration of N-AcGIP($LysPAL^{37}$) to young adult ob/ob mice by intraperitoneal injection (12.5 nmoles/kg) resulted in a progressive lowering of plasma glucose concentrations and a significant decrease of glycated haemoglobin by 14 days. This was associated with a substantial improvement of glucose tolerance. Importantly food intake and body weight were unchanged ruling out the possibility that improvement of glucose homeostasis was merely the consequence of body weight loss. These observations also indicate that N-AcGIP($LysPAL^{37}$) did not exert any untoward toxic actions affecting feeding over the study period. This is in harmony with recent studies showing that GIP does not inhibit gastric emptying (Meier, J. J. et al., 2003, *Am. J. Physiol. Endocrinol. Metab.* 286: 621-625). Daily administration of native GIP to ob/ob mice for 14 days had no effect on any of the parameters measure, consistent with the very short half-life of the native GIP in vivo.

As expected, a key component of the beneficial action of N-AcGIP($LysPAL^{37}$) concerned effects on beta-cells. Thus although native GIP is a weak stimulus to insulin secretion in ob/ob mice at the age studied, plasma and pancreatic insulin concentrations were raised in ob/ob mice receiving the novel fatty acid derivatised analogue. This is consistent with the action of GIP as a promoter of proinsulin gene expression (Wang, Y. et al., 1996, *Mol. Cell. Endocrinol.* 116:81-87) and exemplifies the increased potency reported for N-terminally modified GIP analogues in this animal model of diabetes (Hinke, S. A. et al., 2002, *Diabetes* 51: 656-661; Gault, V. A. et al., 2002, *Biochem. J.* 367: 913-920; Gault, V. A. et al., 2003, *J. Endocrinol.* 176: 133-141; O'Harte, F. P. M. et al., 1999, *Diabetes* 48: 758-765; O'Harte, F. P. M. et al., 2002, *Diabetologia* 45: 1281-1291). Furthermore, the insulin response to glucose was significantly enhanced in ob/ob mice receiving N-AcGIP($LysPAL^{37}$). This ability to augment or restore pancreatic beta cell glucose responsiveness has been similarly observed with GLP-1 (Holz, G. G. et al., 1993, *Nature* 28: 362-365; Flamez, D. et al., 1998, *Diabetes* 47: 646-652). As with observations on glycaemic control, none of these attributes were reproduced by daily injections of native GIP.

Results of insulin sensitivity tests conducted after 14 days treatment indicate that the improvement of diabetic status achieved in ob/ob mice with N-AcGIP($LysPAL^{37}$) was not solely due to the potentiation of insulin secretion. Thus, these animals also exhibited a significant improvement of insulin sensitivity compared to the GIP or saline treated groups. Given that hyperinsulinemia is generally believed to down-regulate insulin receptor function (Marshall, S. et al., 1981, *Diabetes* 30: 746-753), this suggests that N-AcGIP($LysPAL^{37}$) may exert other compensatory effects. Further study is necessary to evaluate this aspect but possibilities include inhibition of counter-regulatory hormones and effects on extrapancreatic sites such as muscle, adipose tissue and liver (Morgan, L. M. et al., 1996, *Biochem. Soc. Trans.* 24:585-591; O'Harte, F. P. M. et al., 1998, *J. Endocrinol.* 156: 237-243; Yip, R. G. et al., 1998, *Endocrinology* 139: 4004-4007).

Irrespective of knowledge of the full range of actions contributing to the antihyperglycaemic effect of N-AcGIP(LysPAL$^{37}$), a currently envisaged problem of long-term treatment with stable analogues of GIP or GLP-1 concerns desensitization of hormone receptor action (Delmeire, D. et al., 2004, *Biochem. Pharmacol.* 68: 33-39). Although this has been observed during prolonged exposure of pancreatic beta cells to GIP in rats (Tseng, C. C. et al., 1996, *Am. J. Physiol.* 270: E661-E666), there was no evidence that treatment with N-AcGIP(LysPAL$^{37}$) for 14 days compromised the glucose lowering or insulin releasing actions of N-AcGIP(LysPAL$^{37}$). Thus the antidiabetic actions of N-AcGIP(LysPAL$^{37}$) were clearly evident when the analogue was administered acutely together with glucose. Furthermore, the acute effects of N-AcGIP(LysPAL$^{37}$) in such experiments were identical in groups of ob/ob mice receiving either N-AcGIP (LysPAL$^{37}$), native GIP or saline injections for 14 days.

Such data clearly indicate that prolonged exposure to N-AcGIP(LysPAL$^{37}$) does not induce and possibly overcomes inherent GIP receptor desensitization in ob/ob mice. Given the high circulating concentrations of GIP in these obese-diabetic rodents (Flatt, P. R. et al., 1983, *Diabetes* 32: 433-435; Flatt, P. R. et al., 1984, *J. Endocrinol.* 101: 249-256), it is tempting to link beta cell refractoriness to GIP evident in ob/ob mice to simple receptor desensitization at the hands of inappropriate secretion and metabolism of GIP.

The data shown herein demonstrate that N-terminally acetylated GIP carrying a palmitate group linked to Lys at position 37 displays resistance to DPP IV and an impressive profile of bioactivity manifested by potent and long-acting glucose-lowering activity in a commonly employed animal model of obesity-diabetes. This activity profile provides strong encouragement for the development of long-acting fatty acid derivatised N-terminally modified analogues of GIP for the once-daily treatment of type 2 diabetes.

The peptide analogues of the present invention have use in treating diseases and conditions caused by improper modulation of insulin levels, including diabetes, type 2 diabetes, insulin resistance, insulin resistant metabolic syndrome (Syndrome X), and obesity.

A peptide analogue produced by the methods of the present invention can be used in a pharmaceutical composition, wherein the analogue is combined with a pharmaceutically acceptable carrier. Such a composition may also contain (in addition to the analogue and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient (s). The characteristics of the carrier will depend on the route of administration.

Administration of the peptide analogue of the present invention used in the pharmaceutical composition or to practice the method of the present invention can be carried out in a variety of conventional ways, such as by oral ingestion, inhalation, topical application or cutaneous, subcutaneous, intraperitoneal, parenteral or intravenous injection. Administration can be internal or external; or local, topical or systemic.

The compositions containing a peptide analogue of this invention can be administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent, i.e., carrier or vehicle.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

When a therapeutically effective amount of the composition of the present invention is administered orally, the composition of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the composition of the present invention, and preferably from about 1 to 50% of the composition of the present invention.

When a therapeutically effective amount of the composition of the present invention is administered by intravenous, cutaneous or subcutaneous injection, the composition of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to the composition of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

Use of timed release or sustained release delivery systems are also included. A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The therapeutic compositions can include pharmaceutically acceptable salts of the components therein, e.g., which may be derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge, et al., describe pharmaceutically acceptable salts in detail in *J. Pharmaceutical Sciences* (1977) 66:1 et seq., which is incorporated herein by reference in its entirety. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. The salts may be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptonoate, hexanoate, fumarate, hydrochloride, hydrobromide, hydroiodide, 2-hydroxymethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

As used herein, the terms "pharmaceutically acceptable", "physiologically tolerable" and grammatical variations thereof as they refer to compositions, carriers, diluents and reagents, are used interchangeably and represent that the materials are capable of administration to or upon a mammal with a minimum of undesirable physiological effects such as nausea, dizziness, gastric upset and the like. The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The amount of peptide analogue of the present invention in the pharmaceutical composition of the present invention will depend upon the nature and severity of the condition being treated, on the nature of prior treatments which the patient has undergone, and on a variety of other factors, including the type of injury, the age, weight, sex, medical condition of the individual. Ultimately, the attending physician will decide the amount of the analogue with which to treat each individual patient. Initially, the attending physician will administer low doses of peptide analogue and observe the patient's response. Larger doses of peptide analogue may be administered until the optimal therapeutic effect is obtained for the patient, and at that point the dosage is not increased further.

Additional guidance on methods of determining dosages can be found in standard references, for example, Spilker, *Guide to Clinical Studies and Developing Protocols*, Raven Press Books, Ltd., New York, 1984, pp. 7-13 and 54-60; Spilker, *Guide to Clinical Trials*, Raven Press, Ltd., New York, 1991, pp. 93-101; Craig et al., *Modern Pharmacology*, 2d ed., Little Brown and Co., Boston, 1986, pp. 127-133; Speight, *Avery's Drug Treatment: Principles and Practices of Clinical Pharmacology and Therapeutics*, 3d ed., Williams and Wilkins, Baltimore, 1987, pp. 50-56; Tallarida et al., *Principles in General Pharmacology*, Springer-Verlag, New York, 1998, pp. 18-20; and Olson, *Clinical Pharmacology Made Ridiculously Simple*, MedMaster, Inc., Miami, 1993, pp. 1-5.

EXAMPLES

Example 1

Preparation of N-Terminally Modified GIP and Analogues Thereof

The N-terminal modification of GIP is essentially a three step process. Firstly, GIP is synthesized from its C-terminal (starting from a Fmoc-Gln (Trt)-Wang resin (Calbiochem Novabiochem, Beeston, Nottingham, UK) up to the penultimate N-terminal amino-acid ($Ala^2$) on an automated peptide synthesizer (Applied Biosystems, California, USA). The synthesis follows standard Fmoc peptide chemistry protocols. Secondly, the N-terminal amino acid of native GIP (Tyr) is added to a manual bubbler system as a Fmoc-protected Tyr (tBu)-Wang resin. This amino acid is deprotected at its N-terminus (piperidine in DMF (20% v/v)) and allowed to react with a high concentration of glucose (glycation, under reducing conditions with sodium cyanoborohydride), acetic anhydride (acetylation), pyroglutamic acid (pyroglutamyl) etc. for up to 24 hours as necessary to allow the reaction to go to completion. The completeness of reaction is monitored using the ninhydrin test which determines the presence of available free a-amino groups. Thirdly (once the reaction is complete), the now structurally modified Tyr is cleaved from the Wang resin (95% TFA, and 5% of the appropriate scavengers. N.B. Tyr is considered to be a problematic amino acid and may need special consideration) and the required amount of N-terminally modified-Tyr consequently added directly to the automated peptide synthesiser, which will carry on the synthesis, thereby stitching the N-terminally modified-Tyr to the a-amino of GIP (Ala$^2$), completing the synthesis of the GIP analogue. This peptide is cleaved off the Wang resin (as above) and then worked up using the standard Buchner filtering, precipation, rotary evaporation and drying techniques.

Example 2

Preparation of Tyr$^1$-Glucitol GIP and its Properties In Vivo

The following example investigates preparation of Tyr$^1$ glucitol GIP together with evaluation of its antihyperglycemic and insulin-releasing properties in vivo. The results clearly demonstrate that this novel GIP analogue exhibits a substantial resistance to aminopeptidase degradation and increased glucose lowering activity compared with the native GIP.

Research Design and Methods

Materials. Human GIP was purchased from the American Peptide Company (Sunnyvale, Calif., USA). HPLC grade acetonitrile was obtained from Rathburn (Walkersburn, Scotland). Sequencing grade trifluoroacetic acid (TFA) was obtained from Aldrich (Poole, Dorset, UK). All other chemicals purchased including dextran T-70, activated charcoal, sodium cyanoborohydride and bovine serum albumin fraction V were from Sigma (Poole, Dorset, UK). Diprotin A (DPA) was purchased from Calbiochem-Novabiochem (UK) Ltd. (Beeston, Nottingham, UK) and rat insulin standard for RIA was obtained from Novo Industria (Copenhagen, Denmark). Reversed-phase Sep-Pak cartridges (C-18) were purchased from Millipore-Waters (Milford, Mass., USA). All water used in these experiments was purified using a Milli-Q Water Purification System (Millipore Corporation, Milford, Mass., USA).

Preparation of Tyr$^1$-glucitol GIP. Human GIP was incubated with glucose under reducing conditions in 10 mmol/l sodium phosphate buffer at pH 7.4 for 24 hours. The reaction was stopped by addition of 0.5 mol/l acetic acid (30 µl) and the mixture applied to a Vydac (C18)(4.6×250 mm) analytical HPLC column (The Separations Group, Hesperia, Calif., USA) and gradient elution conditions were established using aqueous/TFA and acetonitrile/TFA solvents. Fractions corresponding to the glycated peaks were pooled, taken to dryness under vacuum using an AES 1000 Speed-Vac concentrator (Life Sciences International, Runcorn, UK) and purified to homogeneity on a Supelcosil (C-8) (4.6×150 mm) column (Supelco Inc., Poole, Dorset, UK).

Degradation of GIP and Tyr$^1$-glucitol GIP by DPP IV. HPLC-purified GIP or Tyr$^1$-glucitol GIP were incubated at 37° C. with DPP-IV (5 mU) for various time periods in a reaction mixture made up to 500 µl with 50 mmol/l triethanolamine-HCl, pH 7.8 (final peptide concentration 1 mmol/l). Enzymatic reactions were terminated after 0, 2, 4 and 12 hours by addition of 5 µl of 10% (v/v) TFA/water. Samples were made up to a final volume of 1.0 ml with 0.12% (v/v) TFA and stored at −20° C. prior to HPLC analysis.

Degradation of GIP and Tyr$^1$-glucitol GIP by human plasma. Pooled human plasma (20 µl) taken from six healthy fasted human subjects was incubated at 37° C. with GIP or Tyr$^1$-glucitol GIP (10 µg) for 0 and 4 hours in a reaction mixture made up to 500 µl, containing 50 mmol/l triethanolamine/HCL buffer pH 7.8. Incubations for 4 hours were also performed in the presence of diprotin A (5 mU). The reactions were terminated by addition of 5 µl of TFA and the final volume adjusted to 1.0 ml using 0.1% v/v TFA/water. Samples were centrifuged (13,000 g, 5 minutes) and the supernatant applied to a C-18 Sep-Pak cartridge (Millipore-Waters) which was previously primed and washed with 0.1% (v/v) TFA/water. After washing with 20 ml 0.12% TFA/water, bound material was released by elution with 2 ml of 80% (v/v) acetonitrile/water and concentrated using a Speed-Vac concentrator (Runcorn, UK). The volume was adjusted to 1.0 ml with 0.12% (v/v) TFA/water prior to HPLC purification.

HPLC analysis of degraded GIP and Tyr$^1$-glucitol GIP. Samples were applied to a Vydac C-18 widepore column equilibrated with 0.12% (v/v) TFA/H$_2$0 at a flow rate of 1.0 ml/minute. Using 0.1% (v/v) TFA in 70% acetonitrile/H$_2$0, the concentration of acetonitrile in the eluting solvent was raised from 0% to 31.5% over 15 min, to 38.5% over 30 minutes and from 38.5% to 70% over 5 minutes, using linear gradients. The absorbance was monitored at 206 nm and peak areas evaluated using a model 2221 LKB integrator. Samples recovered manually were concentrated using a Speed-Vac concentrator.

Electrospray ionization mass spectrometry (ESI-MS). Samples for ESI-MS analysis containing intact and degradation fragments of GIP (from DPP IV and plasma incubations) as well as Tyr$^1$-glucitol GIP, were further purified by HPLC. Peptides were dissolved (approximately 400 pmol) in 100 µl of water and applied to the LCQ benchtop mass spectrometer (Finnigan MAT, Hemel Hempstead, UK) equipped with a microbore C-18 HPLC column (150×2.0 mm, Phenomenex, Ltd., Macclesfield, UK). Samples (30% direct loop injection) were injected at a flow rate of 0.2 ml/min, under isocratic conditions 35% (v/v) acetonitrile/water. Mass spectra were obtained from the quadripole ion trap mass analyzer and recorded. Spectra were collected using full ion scan mode over the mass-to-charge (m/z) range 150-2000. The molecular masses of GIP and related structures were determined from ESI-MS profiles using prominent multiple charged ions and the following equation $$M_r = iM_i - iM_h$$

where $M_r$=molecular mass; $M_i$=m/z ratio; i=number of charges; $M_h$=mass of a proton.

In vivo biological activity of GIP and Tyr$^1$-glucitol GIP. Effects of GIP and Tyr$^1$-glucitol GIP on plasma glucose and insulin concentrations were examined using 10-12 week old male Wistar rats. The animals were housed individually in an air conditioned room and 22±2° C. with a 12 hour light/12 hour dark cycle. Drinking water and a standard rodent maintenance diet (Trouw Nutrition, Belfast, Northern Ireland) were supplied ad libitum. Food was withdrawn for an 18 hour period prior to intraperitoneal injection of glucose alone (18 mmol/kq body weight) or in combination with either GIP or Tyr$^1$-glucitol GIP (10 nmol/kg). Test solutions were administered in a final volume of 8 ml/kg body weight. Blood samples were collected at 0, 15, 30 and 60 minutes from the cut tip of the tail of conscious rats into chilled fluoride/heparin microcentrifuge tubes (Sarstedt, Numbrecht, Germany). Samples were centrifuged using a Beckman microcentrifuge for about 30 seconds at 13,000 g. Plasma samples were aliquoted and stored at −20° C. prior to glucose and insulin determinations. All animal studies were done in accordance with the Animals (Scientific Procedures) Act 1986.

Analyses. Plasma glucose was assayed by an automated glucose oxidase procedure using a Beckman Glucose Analyzer II [33]. Plasma insulin was determined by dextran charcoal radioimmunoassay as described previously [34]. Incremental areas under plasma glucose and insulin area under the curve (AUC) were calculated using a computer program (CAREA) employing the trapezoidal rule [35] with baseline subtraction. Results are expressed as mean±SEM and values were compared using the Student's unpaired t-test. Groups of data were considered to be significantly different if P<0.05.

Degradation of GIP and $Tyr^1$-glucitol GIP by DPP IV. FIG. 1 illustrates the typical peak profiles obtained from the HPLC separation of the products obtained from the incubation of GIP (FIG. 1a) or $Tyr^1$-glucitol GIP (FIG. 1b) with DPP IV for 0, 2, 4 and 12 hours. The retention times of GIP and $Tyr^1$-glucitol GIP at t=0 were 21.93 minutes and 21.75 minutes respectively. Degradation of GIP was evident after 4 hours incubation (54% intact), and by 12 hours the majority (60%) of intact GIP was converted to the single product with a retention time of 21.61 minutes. $Tyr^1$-glucitol GIP remained almost completely intact throughout 2-12 hours incubation. Separation was on a Vydac C-18 column using linear gradients of 0% to 31.5% acetonitrile over 15 minutes, to 38.5% over 30 minutes and from 38.5 to 70% acetonitrile over 5 minutes.

Figure 2A:
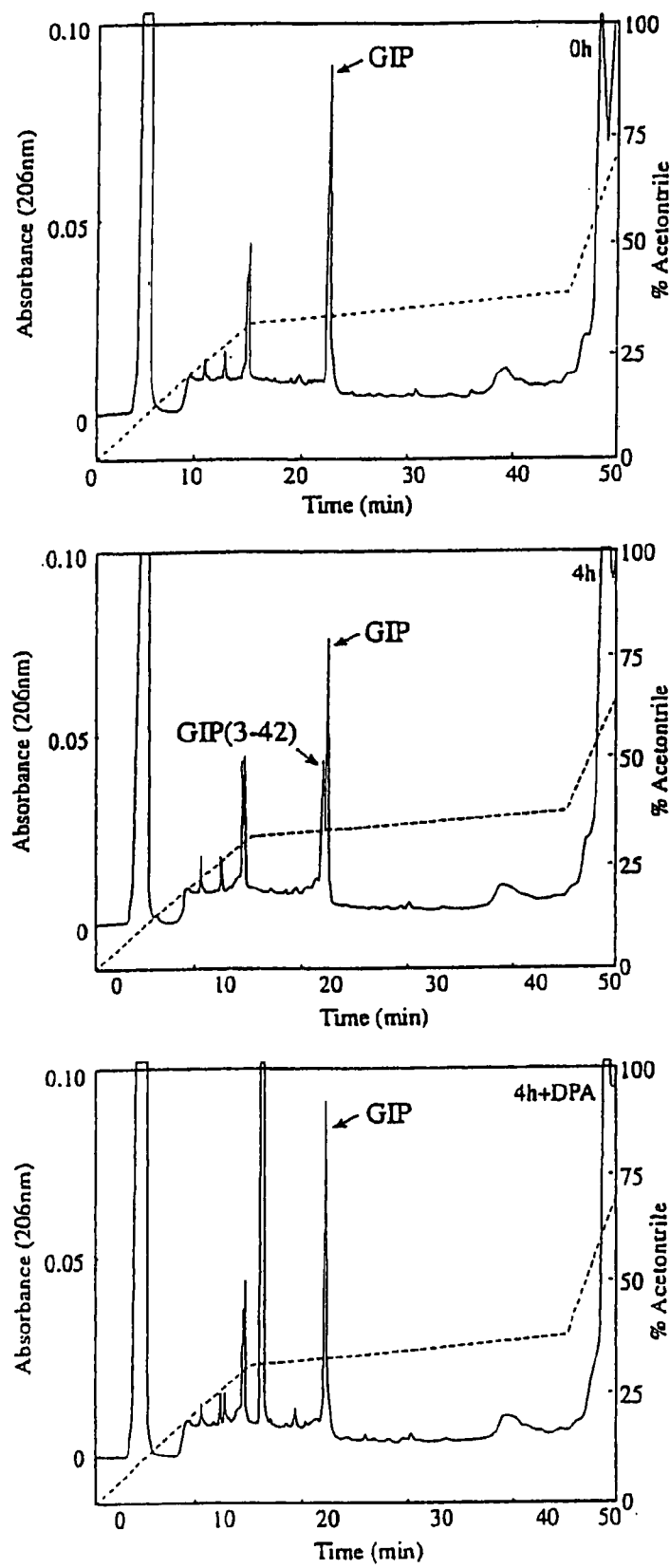
FIG. 2a illustrates degradation of GIP human plasma.

Degradation of GIP and $Tyr^1$-glucitol GIP by human plasma. FIG. 2 shows a set of typical HPLC profiles of the products obtained from the incubation of GIP or $Tyr^1$-glucitol GIP with human plasma for 0 and 4 hours. GIP (FIG. 2a) with a retention time of 22.06 minutes was readily metabolised by plasma within 4 hours incubation giving rise to the appearance of a major degradation peak with a retention time of 21.74 minutes. In contrast, the incubation of $Tyr^1$-glucitol GIP under similar conditions (FIG. 2b) did not result in the formation of any detectable degradation fragments during this time with only a single peak being observed with a retention time of 21.77 minutes. Addition of diprotin A, a specific inhibitor of DPP IV, to GIP during the 4 hours incubation completely inhibited degradation of the peptide by plasma. Peaks corresponding with intact GIP, GIP (3-42) and $Tyr^1$-glucitol GIP are indicated. A major peak corresponding to the specific DPP IV inhibitor tripeptide DPA appears in the bottom peanels with retention time of 16-29 minutes.

Figure 3:
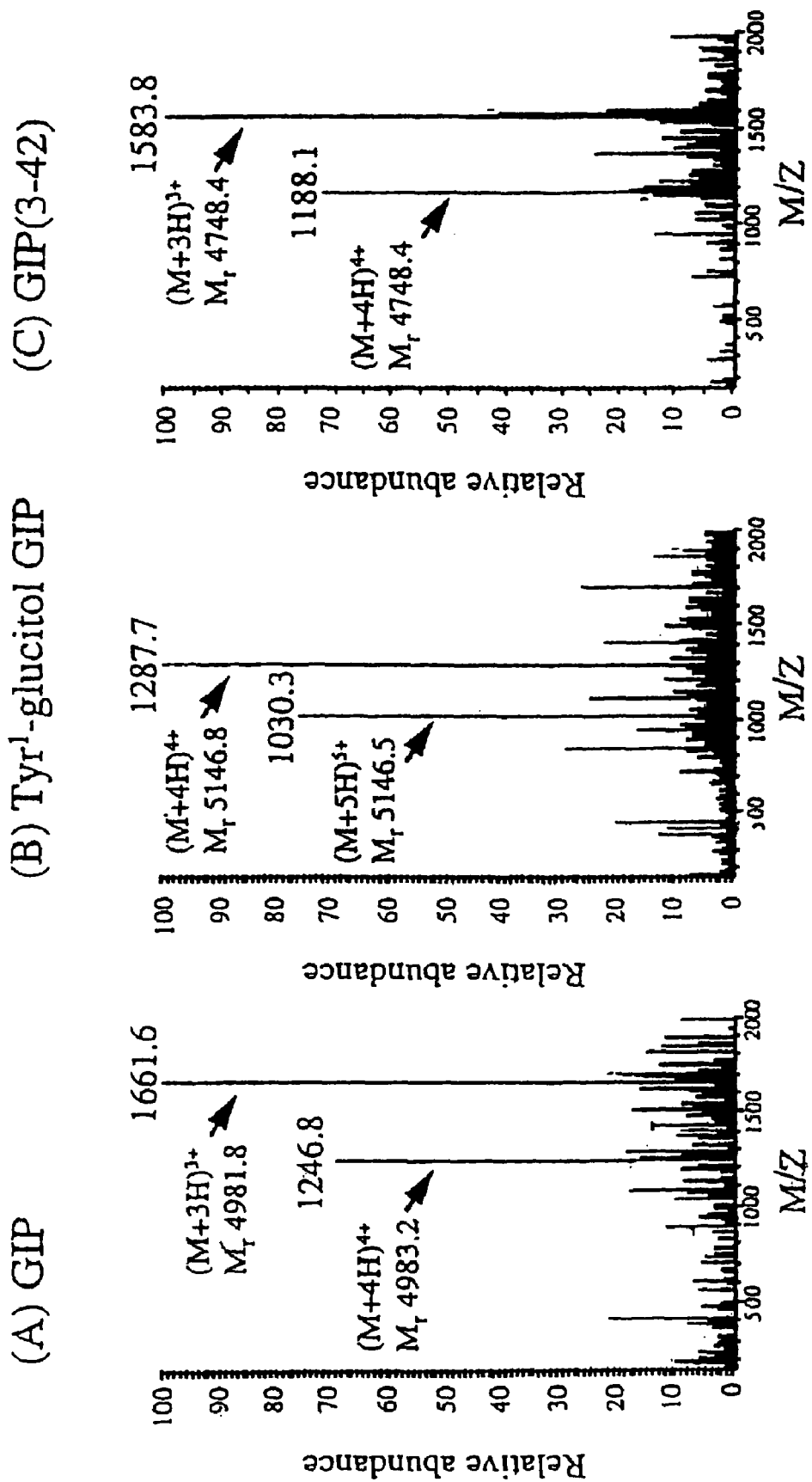
FIG. 3 illustrates electrospray ionization mass spectrometry of GIP, $Tyr^1$-glucitol GIP and the major degradation fragment GIP(3-42).

Identification of GIP degradation fragments by ESI-MS. FIG. 3 shows the monoisotopic molecular masses obtained for GIP (FIG. 3A), $Tyr^1$-glucitol GIP (FIG. 3B) and the major plasma degradation fragment of GIP (FIG. 3C) using ESI-MS. The peptides analyzed were purified from plasma incubations as shown in FIG. 2. Peptides were dissolved (approximately 400 pmol) in 100 µl of water and applied to the LC/MS equipped with a microbore C-18 HPLC column. Samples (30 µl direct loop injection) were applied at a flow rate of 0.2 ml/min, under isocratic conditions 35% acetonitrile/water. Mass spectra were recorded using a quadripole ion trap mass analyzer. Spectra were collected using full ion scan mode over the mass-to-charge (m/z) range 150-2000. The molecular masses ($M_r$) of GIP and related structures were determined from ESI-MS profiles using prominent multiple charged ions and the following equation $M_r=iM_i-iM_h$. The exact molecular mass ($M_r$) of the peptides were calculated using the equation $M_r=iM_i-iM_h$ as defined above in Research Design and Methods. After spectral averaging was performed, prominent multiple charges species $(M+3H)^{3+}$ and $(M+4H)^{4+}$ were detected from GIP at m/z 1661.6 and 1246.8, corresponding to intact $M_r$, 4981.8 and 4983.2 Da, respectively (FIG. 3A). Similarly, for $Tyr^1$-glucitol GIP $((M+4H)^{4+}$ and $(M+5H)^{5+})$ were detected at m/z 1287.7 and 1030.3, corresponding to intact molecular masses of $M_r$, 5146.8 and 5146.5 Da, respectively (FIG. 3B). The difference between the observed molecular masses of the quadruply charged GIP and the N-terminally modified GIP species (163.6 Da) indicated that the latter peptide contained a single glucitol adduct corresponding to $Tyr^1$-glucitol GIP. FIG. 3C shows the prominent multiply charged species $(M+3H)^{3+}$ and $(M+4H)^{4+}$ detected from the major fragment of GIP at m/z 1583.8 and 1188.1, corresponding to intact $M_r$, 4748.4 and 4748 Da, respectively (FIG. 3C). This corresponds with the theoretical mass of the N-terminally truncated form of the peptide GIP (3-42). This fragment was also the major degradation product of DPP IV incubations (data not shown).

Effects of GIP and $Tyr^1$-glucitol GIP on plasma glucose homeostasis. FIGS. 4 and 5 show the effects of intraperitoneal (ip) glucose alone (18 mmol/kg) (control group), and glucose in combination with GIP or $Tyr^1$-glucitol GIP (10 nmol/kg) on plasma glucose and insulin concentrations.

FIG. 4A shows plasma glucose concentrations after i.p. glucose alone (18 mmol/kg) (control group), or glucose in combination with either GIP of $Tyr^1$-glucitol GIP (10 nmol/kg). The time of injection is indicated by the arrow (0 minutes). FIG. 4B shows plasma glucose AUC values for 0-60 minutes post injection. Values are mean±SEM for six rats. $P<0.01$, $*P<0.001$ compared with GIP and $Tyr^1$-glucitol GIP; $†P<0.05$, $‡‡P<0.01$ compared with non-glucated GIP. FIG. 5A shows plasma insulin concentrates after i.p. glucose along (18 mmol/kg) (control group), or glucose in combination with either with GIP or glycated GIP (10 nmol/kq). The time of injection is indicated by the arrow. FIG. 5B shows plasma insulin AUC values were calculated for each of the 3 groups up to 90 minutes post injection. The time of injection is indicated by the arrow (0 minutes). Plasma insulin AUC values for 0-60 minutes post injection. Values are mean±SEM for six rats. $*P<0.05$, $**P<0.001$ compared with GIP and $Tyr^1$-glucitol GIP; $†P<0.05$, $††P<0.01$ compared with non-glycated GIP.

Compared with the control group, plasma glucose concentrations and area under the curve (AUC) were significantly lower following administration of either GIP or $Tyr^1$-glucitol GIP (FIGS. 4A, B). Furthermore, individual values at 15 and 30 minutes together with AUC were significantly lower following administration of $Tyr^1$-glucitol GIP as compared to GIP. Consistent with the established insulin-releasing properties of GIP, plasma insulin concentrations of both peptide-treated groups were significantly raised at 15 and 30 minutes compared with the values after administration of glucose alone (FIG. 5A). The overall insulin responses, estimated as AUC were also significantly greater for the two peptide-treated groups (FIG. 5B). Despite lower prevailing glucose concentrations than the GIP-treated group, plasma insulin response, calculated as AUC, following $Tyr^1$-glucitol GIP was significantly greater than after GIP (FIG. 5B). The significant elevation of plasma insulin at 30 minutes is of particular note, suggesting that the insulin-releasing action of $Tyr^1$-glucitol GIP is more protracted than GIP even in the face of a diminished glycemic stimulus (FIGS. 4A, 5A).

Example 3

Additional N-Terminal Structural Modifications of GIP

This example further looked at the ability of additional N-terminal structural modifications of GIP in preventing inactivation by DPP and in plasma and their associated increase in both the insulin-releasing potency and potential therapeutic value. Native human GIP, glycated GIP, acetylated GIP and a number of GIP analogues with N-terminal amino acid substitutions were tested.

Materials and Methods. High-performance liquid chromatography (HPLC) grade acetonitrile was obtained from Rathburn (Walkersburn, Scotland). Sequencing grade trifluoroacetic acid (TFA) was obtained from Aldrich (Poole, Dorset, UK). Dipeptidyl peptidase IV was purchased from Sigma (Poole, Dorset, UK), and Diprotin A was purchased from Calbiochem Novabiochem (Beeston, Nottingham, UK). RPMI 1640 tissue culture medium, foetal calf serum, penicillin and streptomycin were all purchased from Gibco (Paisley, Strathclyde, UK). All water used in these experiments was purified using a Milli-Q, Water Purification System (Millipore, Milford, Mass., USA). All other chemicals used were of the highest purity available.

Synthesis of GIP and N-terminally modified GIP analogues. GIP, GIP(Abu$^2$), GIP(Sar$^2$), GIP(Ser$^2$), GIP(Gly$^2$) and GIP(Pro$^3$) were sequentially synthesized on an Applied Biosystems automated peptide synthesizer (model 432A) using standard solid-phase Fmoc procedure, starting with an Fmoc-Gln-Wang resin. Following cleavage from the resin by trifluoroacetic acid:water, thioanisole, ethanedithiol (90/2.5/5/2.5, a total volume of 20 ml/g resin), the resin was removed by filtration and the filtrate volume was decreased under reduced pressure. Dry diethyl ether was slowly added until a precipitate was observed. The precipitate was collected by low-speed centrifugation, resuspended in diethyl ether and centrifuged again, this procedure being carried out at least five times. The pellets were then dried in vacuo and judged pure by reversed-phase HPLC on a Waters Millennium 2010 chromatography system (Software version 2.1.5.). N-terminal glycated and acetylated GIP were prepared by minor modification of a published method.

Electrospray ionization-mass spectrometry (ESI-MS) was carried out as described in Example 2. Degradation of GIP and novel GIP analogues by DPP IV and human plasma was carried out as described in Example 2.

Culture of insulin secreting cells. BRIN-BD11 cells [30] were cultured in sterile tissue culture flasks (Corning, Glass Works, UK) using RPMI-1640 tissue culture medium containing 10% (v/v) foetal calf serum, 1% (v/v) antibiotics (100 U/ml penicillin, 0.1 mg/ml streptomycin) and 11.1 mM glucose. The cells were maintained at 37° C. in an atmosphere of 5% $CO_2$ and 95% air using a LEEC incubator (Laboratory Technical Engineering, Nottingham, UK).

Acute tests for insulin secretion. Before experimentation, the cells were harvested from the surface of the tissue culture flasks with the aid of trypsin/EDTA (Gibco), seeded into 24-multiwell plates (Nunc, Roskilde, Denmark) at a density of $1.5 \times 10^5$ cells per well, and allowed to attach overnight at 37° C. Acute tests for insulin release were preceded by 40 minutes pre-incubation at 37° C. in 1.0 ml Krebs Ringer bicarbonate buffer (115 mM NaCl, 4.7 mM KCl, 1.28 mM $CaCl_2$, 1.2 mM $KH_2PO_4$, 1.2 mM $MgSO_4$, 10 mM $NaHCO_3$, 5 g/l bovine serum albumin, pH 7.4) supplemented with 1.1 mM glucose. Test incubations were performed (n=12) at two glucose concentrations (5.6 mM and 16.7 mM) with a range of concentrations ($10^{-13}$ to $10^{-8}$ M) of GIP or GIP analogues. After 20 minutes incubation, the buffer was removed from each well and aliquots (200 μl) were used for measurement of insulin by radioimmunoassay [31].

Statistical analysis. Results are expressed as mean±S.E.M. and values were compared using the Student's unpaired t-test. Groups of data were considered to be significantly different if P<05.

Structural identification of GIP and GIP analogues by ESI-MS. The monoisotopic molecular masses of the peptides were determined using ESI-MS. After spectral averaging was performed, prominent multiple charged species $(M+3H)^{3+}$ and $(M+4H)^{4+}$ were detected for each peptide. Calculated molecular masses confirmed the structural identity of synthetic GIP and each of the N-terminal analogues.

Degradation of GIP and novel GIP analogues by DPP-IV FIGS. 6-11 illustrate the typical peak profiles obtained from the HPLC separation of the reaction products obtained from the incubation of GIP, GIP(Abu$^2$), GIP(Sar$^2$), GIP(Ser$^2$), glycated GIP and acetylated GIP with DPP IV, for 0, 2, 4, 8 and 24 hours. The results summarized in Table 1 indicate that glycated GIP, acetylated GIP, GIP(Ser$^2$) are GIP(Abu$^2$) more resistant than native GIP to in vitro degradation with DPP IV. From these data GIP(Sar$^2$) appears to be less resistant.

TABLE 1

Percent intact peptide remaining after incubation with DPPIV.

| Peptide | % Intact peptide remaining after time (h) | | | | |
|---|---|---|---|---|---|
| | 0 | 2 | 4 | 8 | 24 |
| GIP 1–42 | 100 | 52 ± 1 | 23 ± 1 | 0 | 0 |
| Glycated GIP | 100 | 100 | 100 | 100 | 100 |
| GIP (Abu$^2$) | 100 | 38 ± 1 | 28 ± 2 | 0 | 0 |
| GIP (Ser$^2$) | 100 | 77 ± 2 | 60 ± 1 | 32 ± 4 | 0 |
| GIP (Sar$^2$) | 100 | 28 ± 2 | 8 | 0 | 0 |
| N-Acetyl-GIP | 100 | 100 | 100 | 100 | |

Table represents the percentage of intact peptide (i.e., GIP 1-42) relative to the major degradation product GIP 3-42. Values were taken from HPLC traces performed in triplicate and the mean and S.E.M. values calculated. DPA is diprotin A, a specific inhibitor of DPPIV.

Degradation of GIP and GIP analogues by human plasma. FIGS. 12-16 show a representative set of HPLC profiles obtained from the incubation of GIP and GIP analogues with human plasma for 0, 2, 4, 8 and 24 hours. Observations were also made after incubation for 24 hours in the presence of DPA. These results are summarized in Table 2 are broadly comparable with DPP IV incubations, but conditions which more closely mirror in vivo conditions are less enzymatically severe. GIP was rapidly degraded by plasma. In comparison, all analogues tested exhibited resistance to plasma degradation, including GIP(Sar$^2$) which from DPP IV data appeared least resistant of the peptides tested. DPA substantially inhibited degradation of GIP and all analogues tested with complete abolition of degradation in the cases of GIP(Abu$^2$), GIP(Ser$^2$) and glycated GIP. This indicates that DPP IV is a key factor in the in vivo degradation of GIP.

TABLE 2

Percent intact peptide remaining after incubation with human plasma.

| Peptide | % Intact peptide remaining after incubations with human plasma | | | | | |
|---|---|---|---|---|---|---|
| | 0 | 2 | 4 | 8 | 24 | DPA |
| GIP 1–42 | 100 | 52 ± 1 | 23 ± 1 | 0 | 0 | 68 ± 2 |
| Glycated GIP | 100 | 100 | 100 | 100 | 100 | 100 |
| GIP (Abu$^2$) | 100 | 38 ± 1 | 28 ± 2 | 0 | 0 | 100 |
| GIP (Ser$^2$) | 100 | 77 ± 2 | 60 ± 1 | 32 ± 4 | 0 | 63 ± 3 |
| GIP (Sar$^2$) | 100 | 28 ± 2 | 8 | 0 | 0 | 100 |

Table represents the percentage of intact peptide (i.e., GIP 1-42) relative to the major degradation product GIP 3-42.

Values were taken from HPLC traces performed in triplicate and the mean and S.E.M. values calculated. DPA is diprotin A, a specific inhibitor of DPPIV.

Dose-dependent effects of GIP and novel GIP analogues on insulin secretion. FIGS. 17-30 show the effects of a range of concentrations of GIP, GIP(Abu$^2$), GIP(Sar$^2$), GIP(Ser$^2$), acetylated GIP, glycated GIP, GIP(Gly$^2$) and GIP(Pro$^3$) on insulin secretion from BRIN-BD11 cells at 5.6 and 16.7 mM glucose. Native GIP provoked a prominent and dose-related stimulation of insulin secretion. Consistent with previous studies [28], the glycated GIP analogue exhibited a considerably greater insulinotropic response compared with native peptide. N-terminal acetylated GIP exhibited a similar pattern and the GIP(Ser$^2$) analogue also evoked a strong response. From these tests, GIP(Gly$^2$) and GIP(Pro$^3$) appeared to be the least potent analogues in terms of insulin release. Other stable analogues tested, namely GIP(Abu$^2$) and GIP(Sar$^2$), exhibited a complex pattern of responsiveness dependent on glucose concentration and dose employed. Thus very low concentrations were extremely potent under hyperglycemic conditions (16.7 mM glucose). This suggests that even these analogues may prove therapeutically useful in the treatment of type 2 diabetes where insulinotropic capacity combined with in vivo degradation dictates peptide potency.

Example 4

Glu$^3$ Substituted GIP Improves Obesity-Related Insulin Resistance and Associated Glucose Intolerance This example examines GIP receptor antagonism and obesity-related insulin resistance and associated glucose intolerance using a Glu$^3$-substituted form of GIP, namely, (Pro$^3$) GIP.

Cell lines and animals. In vitro insulin secretion was evaluated using the clonal pancreatic beta-cell line, BRIN-BD11 (McClenaghan, N. H. et al., 1996, *Diabetes* 45:1132-1140). In vitro cyclic AMP generation was measured using Chinese hamster lung (CHL) fibroblast cells stably transfected with the human GIP receptor (Gremlich, S. et al., 1995, *Diabetes* 44:1202-1208). In vivo studies were conducted in 8-12 week-old obese diabetic ob/ob mice (Bailey C. J. et al., 1982, *Int. J. Obesity* 6:11-21) and normal control mice.

Peptide synthesis and characterisation. Glu$^3$-substituted analogues were sequentially synthesised on an Applied Biosystems automated peptide synthesiser (Model 432A) using standard solid-phase Fmoc peptide chemistry (Fields, G. B. et al., 1990, *Int. J. Pept. Protein Res.* 35:161-214), from a pre-loaded Fmoc-Gln-Wang resin. The synthetic peptides were judged pure by reversed-phase HPLC on a Waters Millenium 2010 chromatography system (Software version 2.1.5). The molecular masses of the purified peptide analogues were determined using Matrix Assisted Laser Desorption Ionisation-Time of Flight (MALDI-TOF) mass spectrometry. Samples were dissolved in 10 μl H$_2$O (approximately 40 pmol/l), placed on a stainless steel sample plate and allowed to dry at room temperature. Samples were then mixed with a matrix solution (10 mg/ml solution of α-cyano-4-hydroxycinnamic acid) in acetonitrile/ethanol (1/1) and allowed to dry at room temperature. The molecular masses were then recorded as mass-to-charge (m/z) ratio versus relative peak intensity and compared using theoretical values on a Voyager-DE BioSpectrometry Workstation (PerSeptive Biosystems, Framingham, Mass., USA).

Tissue culture. Chinese hamster lung (CHL) fibroblast cells stably transfected with the human GIP receptor were cultured in DMEM tissue culture medium containing 10% (v/v) foetal bovine serum, 1% (v/v) antibiotics (100 U/ml penicillin, 0.1 mg/ml streptomycin). BRIN-BD11 cells were cultured using RPMI-1640 tissue culture medium containing 10% (v/v) foetal bovine serum, 1% (v/v) antibiotics (100 U/ml penicillin, 0.1 mg/ml streptomycin). Cells were maintained in sterile tissue culture flasks (Corning Glass Works, Sunderland, UK) at 37° C. in an atmosphere of 5% CO$_2$ and 95% air using an LEEC incubator (Laboratory Technical Engineering, Nottingham, UK).

Acute studies of insulin release. Insulin release from BRIN-BD11 cells was determined using cell monolayers (McClenaghan, N. H. et al., 1996, *Diabetes* 45:1132-1140). Cells were harvested with the aid of trypsin/EDTA (Gibco), seeded into 24-multiwell plates (Nunc, Roskilde, Denmark) at a density of 1.0×10$^5$ cells per well, and allowed to attach overnight at 37° C. Prior to acute test, cells were preincubated for 40 minutes at 37° C. in 1.0 ml Krebs Ringer bicarbonate buffer (115 mM NaCl, 4.7 mM KCl, 1.28 mM CaCl$_2$, 1.2 mM KH$_2$PO$_4$, 1.2 mM MgSO$_4$, 10 mM NaHCO$_3$, 0.5% (w/v) bovine serum albumin, pH 7.4) supplemented with 1.1 mM glucose. Acute tests for insulin release were performed for 20 minutes at 37° C. at 5.6 mM glucose using various concentrations of Glu$^3$-substituted analogues and GIP(3-42) in the presence of native GIP (10$^{-7}$ M) as indicated in the Figures. After incubation, aliquots of buffer were removed and stored at −20° C. for insulin radioimmunoassay (Flatt, P. R. et al., 1981, *Diabetologia* 20:573-577).

Acute studies of cyclic AMP generation. GIP receptor transfected CHL cells were seeded into 12-well plates (Nunc, Roskilde, Denmark) at a density of 1.0×10$^5$ cells per well. The cells were then allowed to grow for 48 hours before being loaded with tritiated adenine (2 μCi; TRK311, Amersham, Buckinghamshire, UK) and incubated at 37° C. for 6 hours in 1 ml DMEM, supplemented with 0.5% (w/v) foetal bovine serum. The cells were then washed twice with HBS buffer (130 mM NaCl, 20 mM HEPES, 0.9 mM NaHPO$_4$, 0.8 mM MgSO$_4$, 5.4 mM KCl, 1.8 mM CaCl$_2$, 25 mM glucose, 25 μM phenol red, pH 7.4). The cells were then exposed for 10 minutes at 37° C. to forskolin (FSK, 10 μM) or varying concentrations of (Pro$^3$)GIP in the absence (control) or presence of native GIP (10$^{-7}$ M). After removal of the medium, cells were lysed with 1 ml of 5% trichloroacetic acid (TCA) containing 0.1 mM unlabelled cAMP and 0.1 mM unlabelled ATP. The intracellular tritiated cAMP was then separated on Dowex and alumina exchange resins as previously described (Widmann, C. et al., 1993, *Mol. Pharmacol.* 45:1029-1035).

Acute in vivo effects of (Pro$^3$)GIP administration in obese diabetic ob/ob mice. Plasma glucose and insulin responses were evaluated using 8- to 12-week old obese diabetic ob/ob mice following intraperitoneal (i.p.) injection of native GIP, (Pro$^3$)GIP (25 nmol/kg body weight) or saline (0.9% (w/v) NaCl; control) immediately following the combined injection of GIP (25 nmol/kg body weight) with glucose (18 mmol/kg body weight). All test solutions were administered in a final volume of 8 ml/kg body weight. Blood samples were collected from the cut tip of the tail of conscious mice into chilled fluoride/heparin microcentrifuge tubes (Sarstedt, Numbrecht, Germany) immediately prior to injection and at 15, 30 and 60 minutes post injection. Blood samples were immediately centrifuged using a Beckman microcentrifuge (Beckman Instruments, UK) for 30 seconds at 13000 g and stored at −20° prior to glucose and insulin determinations.

Acute in vivo effects of (Pro$^3$)GIP on plasma glucose and insulin responses to feeding in obese diabetic ob/ob mice. Plasma glucose and insulin responses were evaluated using 8- to 12-week old ob/ob mice where food was withdrawn for an 18-hour period prior to intraperitoneal injection of saline (0.9% (w/v) NaCl; control) or (Pro$^3$)GIP (25 nmol/kg body weight). Following injection, the mice were allowed to re-feed for 15 minutes. Blood samples were collected from the cut tip of the tail of conscious mice into chilled fluoride/heparin microcentrifuge tubes (Sarstedt, Numbrecht, Germany) immediately prior to injection and at 15, 30, 60 and 120 minutes post injection. Blood samples were immediately centrifuged using a Beckman microcentrifuge (Beckman Instruments, UK) for 30 seconds at 13000 g and stored at –20° prior to glucose and insulin determinations.

Effects of chronic (Pro$^3$)GIP administration on plasma glucose, insulin and glycated HbA$_{1c}$ in obese diabetic ob/ob mice and normal mice. Obese diabetic ob/ob mice and normal control mice aged 8-12 weeks were randomly divided into groups which received once daily subcutaneous injections (17:00 h) of either saline (0.9% w/v NaCl) or (Pro$^3$)GIP (25 nmol/kg body weight in saline). After 11 days, treatment was ceased. Food intake and body weight were recorded daily. Blood samples were collected from the cut tip of the tail of conscious mice into chilled fluoride/heparin coated glucose microcentrifuge tubes (Sarstedt, Numbrecht, Germany). Blood samples were immediately centrifuged using a Beckman microcentrifuge (Beckman Instruments, UK) for 30 seconds at 13000 g prior to glucose, insulin and HbA$_{1c}$ determinations.

Effects of chronic treatment with (Pro$^3$)GIP on glucose tolerance in ob/ob mice and normal mice. Plasma glucose and insulin concentrations were measured following intraperitoneal administration of glucose (18 mmol/kg body weight) in ob/ob and normal mice treated with either saline (0.9% w/v NaCl) or (Pro$^3$)GIP (25 nmol/kg body weight/day) for 11 days. This test was repeated 9 days after cessation of chronic (Pro$^3$)GIP treatment. Blood samples were collected from the cut tip of the tail of conscious mice into chilled fluoride/heparin microcentrifuge tubes (Sarstedt, Numbrecht, Germany) immediately prior to injection and at 15, 30 and 60 minutes post injection. Blood samples were immediately centrifuged using a Beckman microcentrifuge (Beckman Instruments, UK) for 30 seconds at 13000 g and stored at –20° prior to glucose and insulin determinations.

Effects of chronic treatment with (Pro$^3$)GIP on the glucose lowering effects of exogenous insulin in ob/ob mice. The glucose lowering effects of insulin were evaluated by measuring plasma glucose response in 11-day saline (0.9% w/v NaCl) and (Pro$^3$)GIP (25 nmol/kg body weight/day) treated ob/ob mice following acute intraperitoneal administration of insulin (50 U/kg bodyweight). Blood samples were collected from the cut tip of the tail of conscious mice into chilled fluoride/heparin microcentrifuge tubes (Sarstedt, Numbrecht, Germany) immediately prior to injection and at 30 and 60 minutes post injection. Blood samples were immediately centrifuged using a Beckman microcentrifuge (Beckman Instruments, UK) for 30 seconds at 13000 g and stored at –20° prior to glucose determination.

Effects of chronic treatment with (Pro$^3$)GIP on pancreatic insulin content and associated islet hypertrophy in ob/ob mice. Pancreatic tissue was excised from non-fasted ob/ob mice after 11 days treatment with either saline (0.9% w/v NaCl) or (Pro$^3$)GIP (25 nmol/kg body weight/day). Pancreatic samples were individually wrapped in aluminium foil and snap frozen in liquid nitrogen. Individual excised pancreatic samples were then either embedded, sectioned and immunohistochemically stained for insulin or permeabilised for determination of pancreatic insulin content.

Determination of HbA$_{1c}$, plasma glucose and insulin concentrations. HbA$_{1c}$ was measured in whole blood by ion-exchange high-performance liquid chromatography using the Menari HA-8140 kit (BIOMEN, Berkshire, UK). Plasma glucose was assayed by an automated glucose oxidase procedure using a Beckman Glucose Analyzer II (Stevens, J. F., 1971, *Clinica Chemica Acta* 32:199-201) and plasma insulin was determined by RIA (Flatt, P. R. et al., 1981, *Diabetologia* 20:573-577). Incremental areas under plasma glucose and insulin curves (AUC) were calculated using a computer generated program (CAREA) employing the trapezoidal rule (Burington, R. S., 1973, *Handbook of Mathematical Tables and Formulae*, New York, McGraw Hill) with baseline subtraction.

Statistical analysis. Results are expressed as means±SEM. Values were compared using Student's unpaired t-test and groups of data were considered to be significantly different if P<0.05.

Results

GIP-stimulated cyclic AMP production and insulin secretion were inhibited in dose-dependent fashion by (Pro$^3$)GIP, showing that (Pro$^3$)GIP is a potent functional GIP receptor antagonist.

Figure 32A:
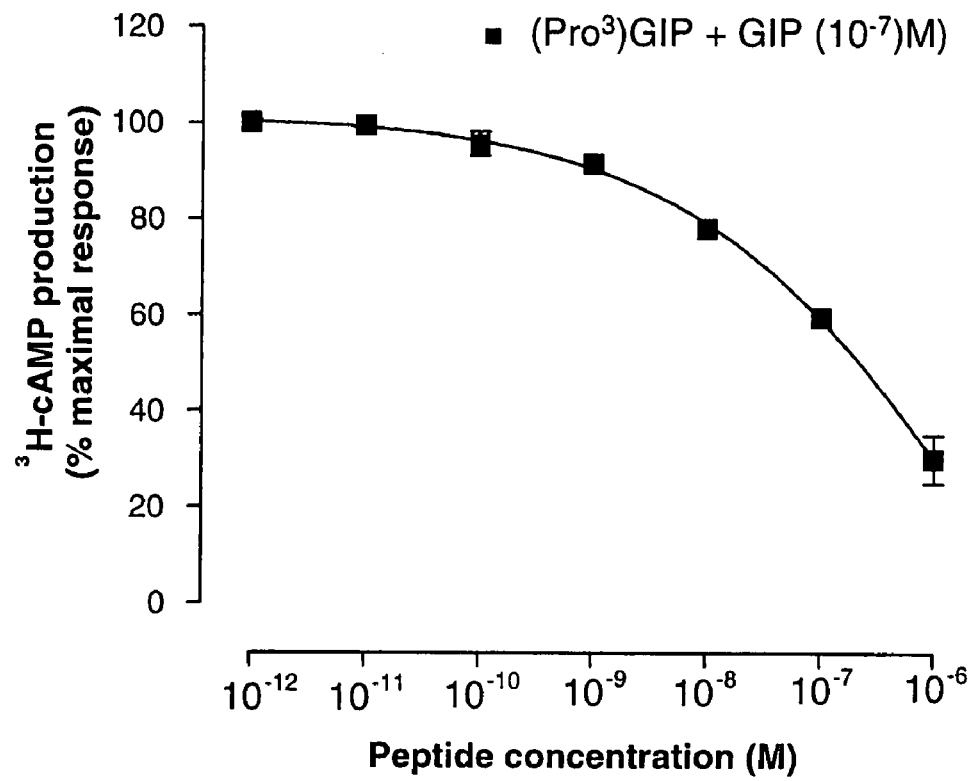
FIGS. 32A and 32B are a line graph and a bar graph, respectively, showing the effects of ($Pro^3$)GIP on GIP-stimulated cyclic AMP generation and insulin secretion in vitro.
Figure 32B:
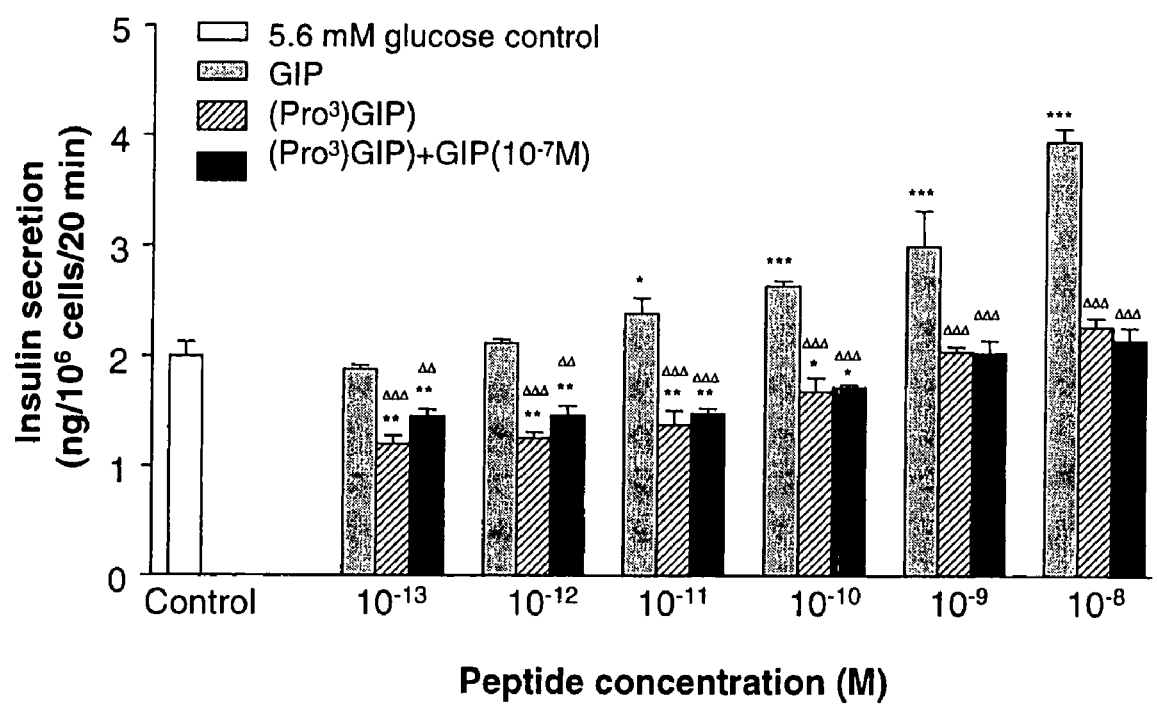

GIP receptor transfected Chinese hamster lung (CHL) fibroblasts were incubated with $10^{-12}$ to $10^{-6}$ M (Pro$^3$)GIP in the presence of native GIP ($10^{-7}$ M). The results are shown in FIGS. 32A and 32B. FIG. 32A is a line graph showing $^3$H-cAMP production as a percent of maximal response (y-axis) with increasing peptide concentration (M) (x-axis). FIG. 32B is a bar graph showing insulin secretion (y-axis) with increasing peptide concentration (M) α-axis) for 5.6 mM glucose (control) (white bar), GIP (gray bars), (Pro$^3$)GIP (lined bars) and (Pro$^3$)GIP+GIP($10^{-7}$M) (black bars). *P<0.05, P<0.01, *P<0.001 compared to glucose control. $^{ΔΔ}$P<0.01, $^{ΔΔΔ}$P<0.001 compared with native GIP at the same concentration. Values are means±SEM for 3-8 observations.

(Pro$^3$)GIP inhibited GIP-induced cAMP formation with an IC$_{50}$ value of 2.6 µM. Insulin-releasing activity of BRIN-BD11 cells exposed to native GIP and (Pro$^3$)GIP (in the absence and presence of $10^{-7}$ M GIP).

GIP-stimulated insulin secretion was inhibited in a dose-dependent fashion by GIP(3-42), (Hyp$^3$)GIP, (Lys$^3$)GIP, (Tyr$^3$)GIP, (Trp$^3$)GIP, and (Phe$^3$)GIP, as shown in FIGS. 33A through 33F, which are bar charts. FIG. 33A shows $^3$H-cAMP production as a percent of $10^{-7}$M GIP (y-axis) versus $\log_{10}$ of GIP ($10^{-7}$M) (white bar, control) and GIP ($10^{-7}$M)+GIP(3-42) (black bars). FIGS. 33B through 33F show insulin secretion (in ng/$10^6$ cells/20 minutes) (y-axis) as a function of peptide concentration (M) (x-axis) for GIP ($10^{-7}$M) (white bar, control) and a Glu$^3$-substituted form of GIP (black bars), including (Hyp$^3$)GIP (FIG. 33B), (Lys$^3$)GIP (FIG. 33C), (Tyr$^3$)GIP (FIG. 33D), (Trp$^3$)GIP (FIG. 33E), and (Phe$^3$)GIP (FIG. 33F). *P<0.05, **P<0.01 compared to GIP ($10^{-7}$ M) control. Values are means±SEM for 3-8 observations.

FIGS. 34A through 34D are a set of two line graphs (FIGS. 34A, 34C) and two bar graphs (FIGS. 34B, 34D) showing that acute administration of (Pro$^3$)GIP completely antagonises the actions of GIP on glucose tolerance (FIGS. 34A, 34B) and plasma insulin (FIGS. 34C, 34D) responses in obese diabetic ob/ob mice. FIGS. 34A and 34C are line graphs show plasma glucose levels (FIG. 34A, y-axis) and plasma insulin levels (FIG. 34C, y-axis) over time (x-axis) for glucose (control; ▼), glucose+GIP (♦) and glucose+(GIP+Pro$^3$GIP)) (Δ). FIGS. 34B and 34D are bar graphs showing plasma glucose AUC for glucose alone (white bars), GIP (grey bars) and glucose+(GIP+Pro$^3$GIP)) (black bars).

Plasma glucose and insulin concentrations after i.p. administration of glucose alone (18 mmol/kg body weight) or in combination with either native GIP or native GIP plus (Pro$^3$) GIP (25 nmol/kg body weight). The time of injection is indicated by the arrow (0 minutes). Plasma glucose and insulin AUC values are given for 0-60 minutes post-injection. Values are means±SEM for 8 mice. *P<0.05, P<0.01, *P<0.001 compared with glucose alone. $^{\Delta\Delta}$P<0.01, $^{\Delta\Delta\Delta}$P<0.001 compared with native GIP.

Acute administration of (Pro$^3$)GIP completely antagonised the insulin-releasing action of GIP and the associated improvement of glucose tolerance in ob/ob mice. Indeed, the glycemic excursion following (Pro 3)GIP (Δ) was worse than when glucose was administered alone (▼).

FIGS. 35A through 35D show the effects of (Pro$^3$)GIP on physiological meal-stimulated insulin release and glycemic excursion in obese diabetic ob/ob mice. Plasma glucose and insulin concentrations were measured in mice allowed to re-feed for 15 minutes prior to i.p. administration of saline (0.9% (w/v) NaCl) as control or (Pro$^3$)GIP (25 nmol/kg body weight). The time of injection is indicated by the arrow (15 minutes).

The results are shown in FIGS. 35A through 35D, which are a set of two line graphs (FIGS. 35A, 35C) and two bar graphs (FIGS. 35B, 35D). The figures show plasma insulin (FIG. 35A) and plasma glucose (FIG. 35C) over time for saline control (▼) and (Pro$^3$)GIP (◇), and plasma insulin AUC (FIG. 35B) and plasma glucose AUC (FIG. 35D) for saline control (white bars) and (Pro$^3$)GIP (black bars), respectively. Values are means±SEM for 8 mice. *P<0.05, P<0.01, *P<0.001 compared with saline alone.

Acute administration of (Pro$^3$)GIP decreased the insulin response to feeding and worsened the associated glycemic excursion in ob/ob mice. These effects of functional ablation of endogenous GIP by the (Pro$^3$)GIP antagonist are fully consistent with the accepted role of GIP in the regulation of insulin secretion and glycemic excursion following feeding.

The effects of chronic administration of (Pro$^3$)GIP for 11 days on plasma glucose and insulin concentrations of obese diabetic ob/ob mice were also studied. According to classical thinking and the experiments described above and the results shown in FIGS. 32-35, functional ablation of endogenous GIP by daily administration of (Pro$^3$)GIP over 11 days would be expected to inhibit insulin secretion and cause a marked deterioration in glucose tolerance.

Figure 36A:
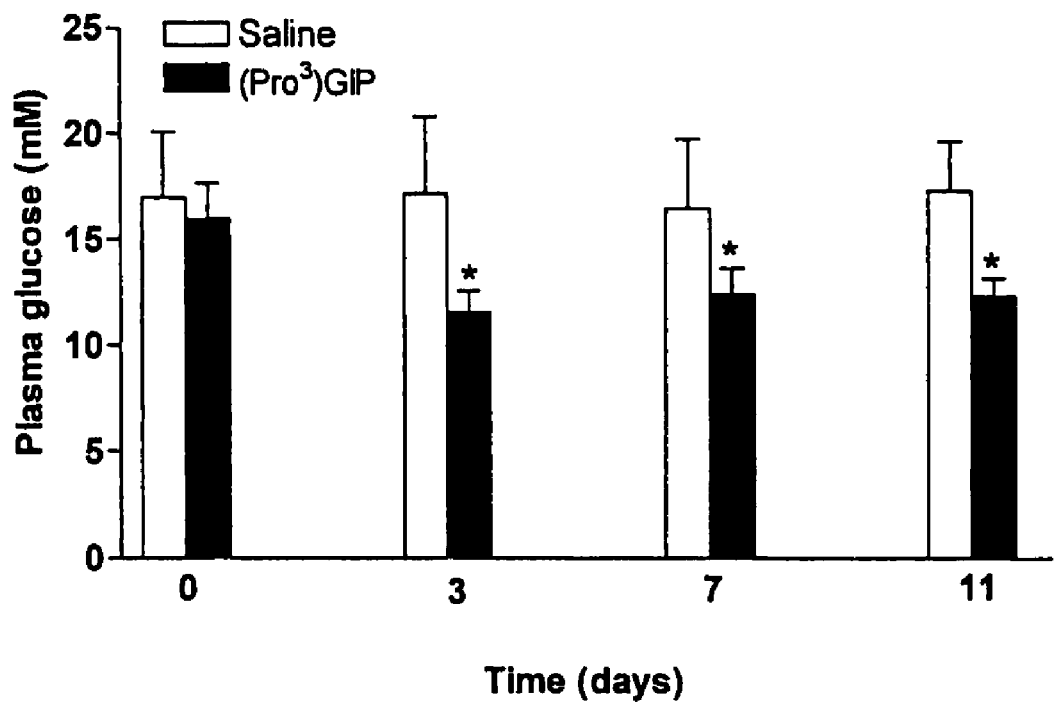
FIGS. 36A and 36B are a set of two bar graphs showing that chronic administration of (Pro$^3$)GIP for 11 days decreases plasma glucose and insulin concentrations of obese diabetic ob/ob mice.
Figure 36B:
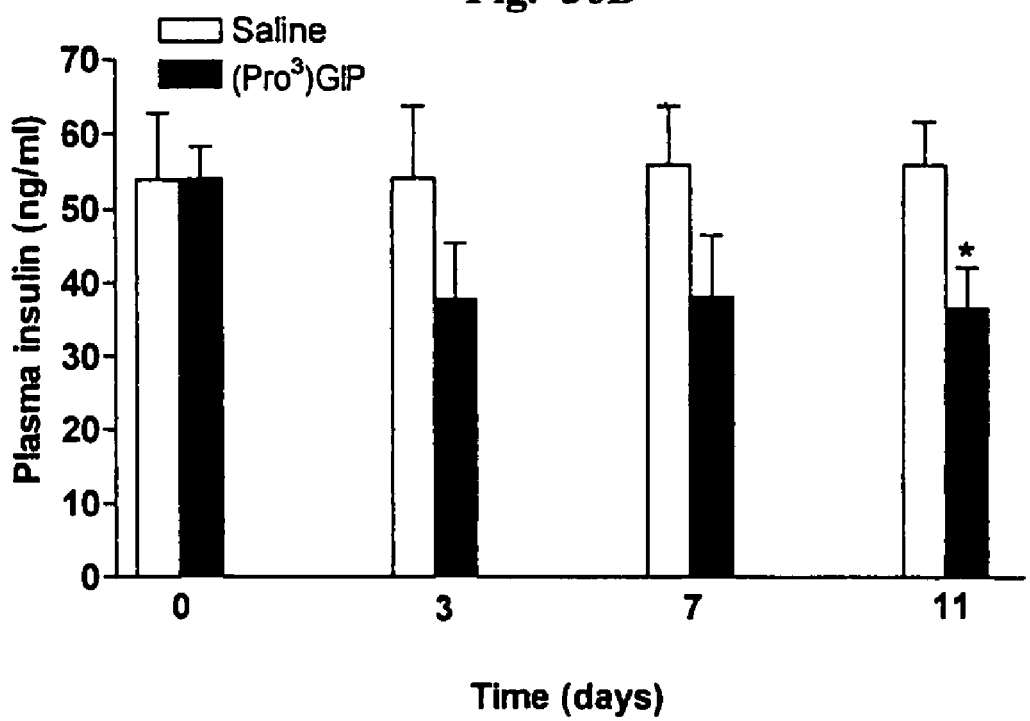
Figure 38A:
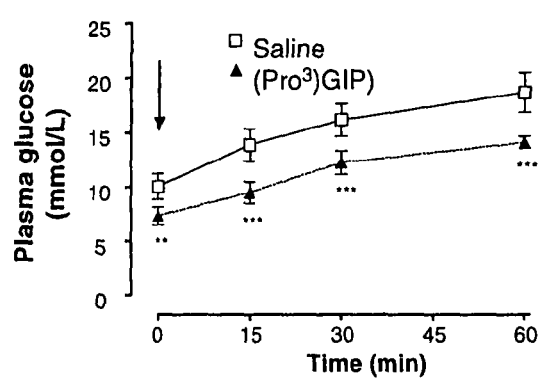
FIGS. 38A through 38D are a set of two line graphs (FIGS. 38A, 38C) and two bar graphs (FIGS. 38B, 38D) showing that chronic administration of (Pro$^3$)GIP for 11 days improves glucose tolerance of obese diabetic ob/ob mice without change of circulating insulin.
Figure 38C:
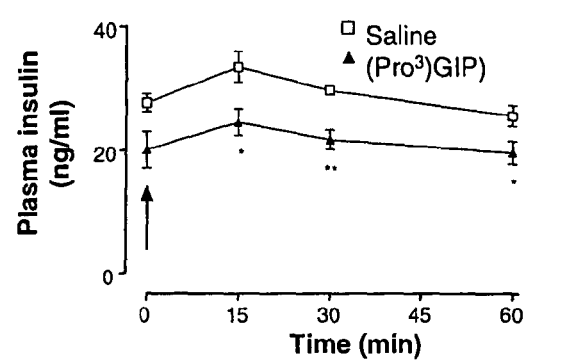
Figure 38B:
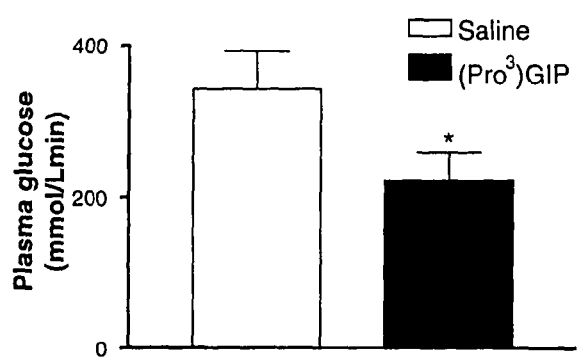
Figure 38D:
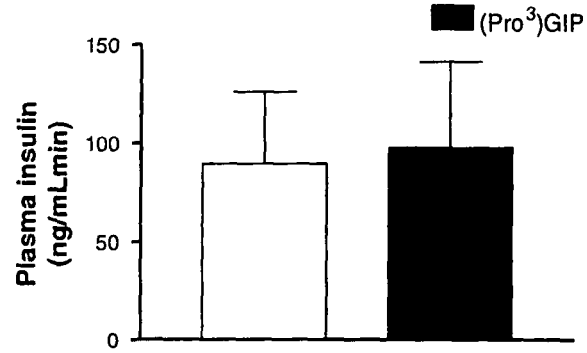

However, the exact opposite occurred during chronic treatment with (Pro$^3$)GIP in ob/ob mice. This is shown in FIG. 36, which is a set of two bar graphs showing plasma glucose (FIG. 36A) and insulin (FIG. 36B) concentrations after daily subcutaneous administration of saline alone (0.9% (w/v) NaCl; as control; white bars) or (Pro$^3$)GIP (25 nmol/kg body weight; black bars) for 11 days. Values are means±SEM for 6 mice and *P<0.05 compared with saline alone. Chronic administration of (Pro$^3$)GIP (black bars) for 11 days decreases plasma glucose and plasma insulin concentrations of obese diabetic ob/ob mice, relative to controls.

The effects of chronic administration of (Pro$^3$)GIP for 11 days on HbA$_{1C}$, (FIG. 37A), pancreatic insulin content (FIG. 37B) and associated islet hypertrophy (FIG. 37C) were examined in obese diabetic ob/ob mice treated with saline (control, white bars) and (Pro$^3$)GIP were examined. HbA$_{1c}$ pancreatic insulin content and average islet diameter were measured after 11 daily subcutaneous injections of either saline alone (white bars) or (Pro$^3$)GIP (25 nmol/kg body weight; black bars) to obese diabetic ob/ob mice. Values are means±SEM for 6 mice and *P<0.05, ***P<0.001 compared with saline-treated group.

Beneficial effects of chronic (Pro$^3$)GIP administration in ob/ob mice were associated with significant decreases in HbA$_{1c}$ and pancreatic insulin stores, with partial correction of the marked islet hypertrophy of the ob/ob mutant. There was also an approximate 7% decrease in body weight in (Pro$^3$) GIP-treated ob/ob mice without any change in food intake. This effect did not achieve significance over the short study period, but this observation clearly suggests that GIP antagonism may also have a longer-term anti-obesity action.

The effects of chronic administration of (Pro$^3$)GIP for 11 days on glucose tolerance and plasma insulin in obese diabetic ob/ob mice is shown in FIGS. 38A-38D, which are a set of line graphs (FIGS. 38A, 38C) and bar graphs (FIGS. 38B, 38C) showing plasma glucose levels (FIGS. 38A, 38B) and plasma insulin levels (FIGS. 38C, 38D) in obese diabetic ob/ob mice treated with saline (control, white) or (Pro$^3$)GIP (black). Plasma glucose and insulin concentrations were measured prior to and at intervals after intraperitoneal administration of glucose (18 mmol/kg body weight). Arrow indicates time of injection (t=0). Values are means±SEM for 6 mice and *P<0.05, P<0.01, *P<0.001 compared with saline-treated group.

After 11 days treatment with (Pro$^3$)GIP, glucose tolerance of ob/ob mice was substantially improved without change of circulating insulin (FIG. 38).

Figure 39:
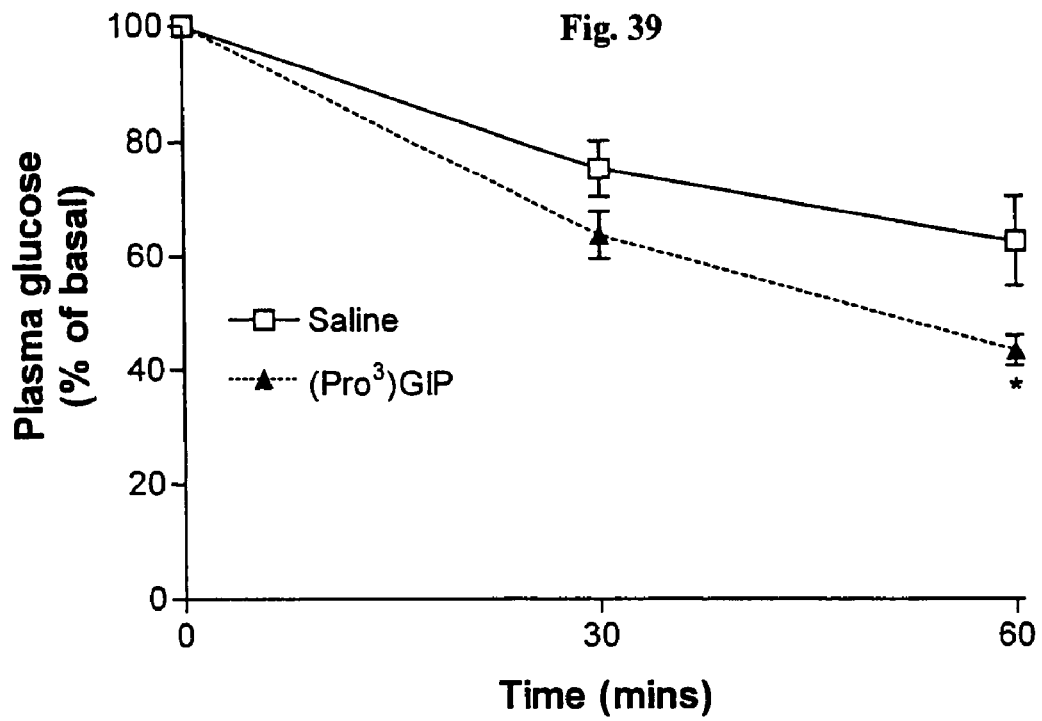
FIG. 39 is a line graph showing that chronic administration of (Pro$^3$)GIP for 11 days improves insulin sensitivity in obese diabetic ob/ob mice.

FIG. 39 shows the effects of chronic administration of (Pro$^3$)GIP for 11 days on insulin sensitivity in obese diabetic ob/ob mice. Plasma glucose concentrations of saline and (Pro$^3$)GIP treated ob/ob mice were measured prior to and at intervals after intraperitoneal administration of exogenous insulin (50 U/kg body weight; t=0). Values are means±SEM for 6 mice and *P<0.05 compared with saline-treated group. As shown in FIG. 39, chronic administration of (Pro$^3$)GIP caused a significant improvement of insulin sensitivity.

Figure 40:
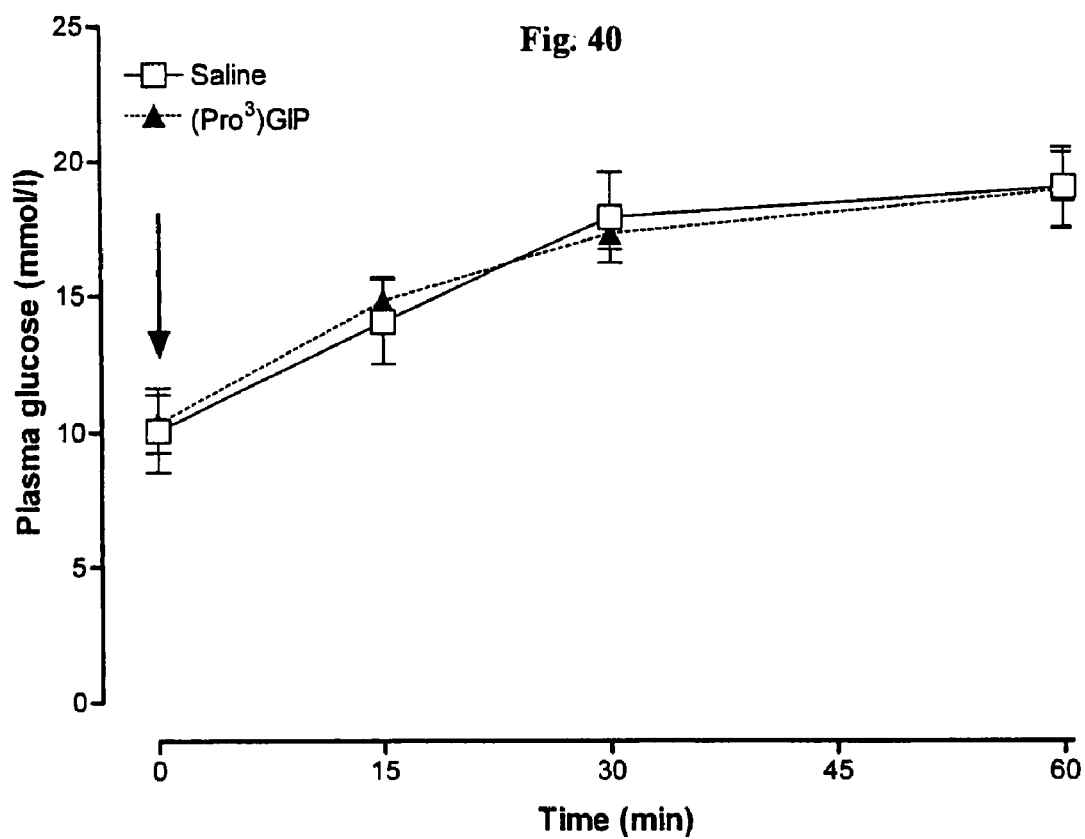
FIG. 40 is a line graph showing that the beneficial effects of chronic administration of (Pro$^3$)GIP for 11 days in obese diabetic ob/ob mice are reversed 9 days after cessation of treatment.

Interestingly, the beneficial effects of chronic administration of (Pro$^3$)GIP for 11 days in obese diabetic ob/ob mice was reversed 9 days after cessation of treatment. This is consistent with a physiological effect, and is shown in FIG. 40. Plasma glucose concentrations were measured prior to and after intraperitoneal administration of glucose (18 mmol/kg body weight) for mice that had been treated with saline (control, □) or (Pro$^3$)GIP (▲). Arrow indicates time of injection (t=0). Values are means±SEM for 6.

Figure 41A:
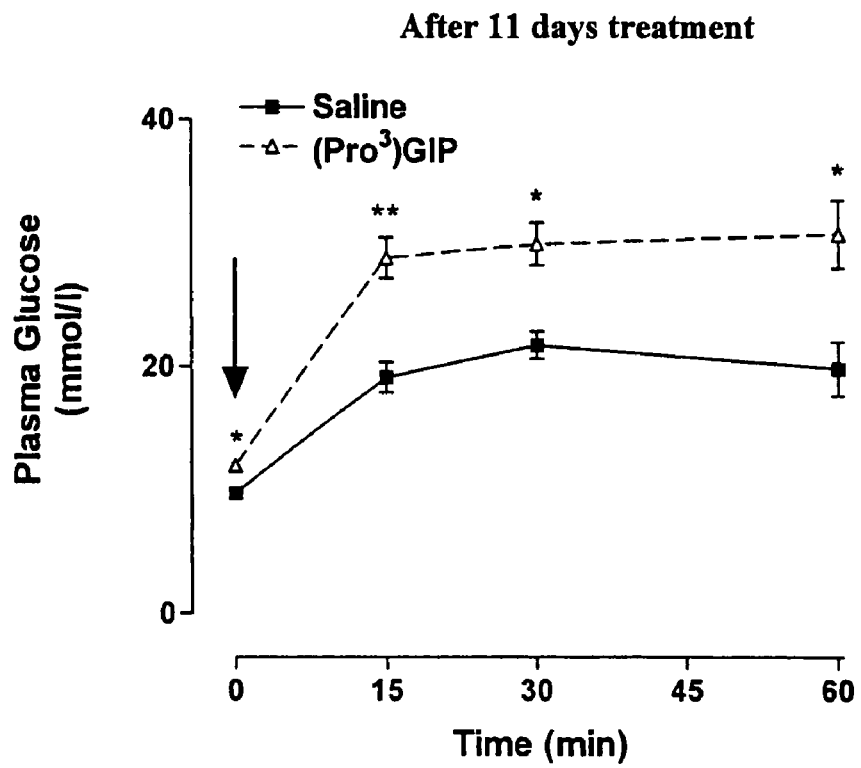
FIGS. 41A and 41B are a set of two line graphs showing that chronic administration of (Pro$^3$)GIP for 11 days causes glucose intolerance in normal mice with reversal by 9 days after cessation of treatment.
Figure 41B:
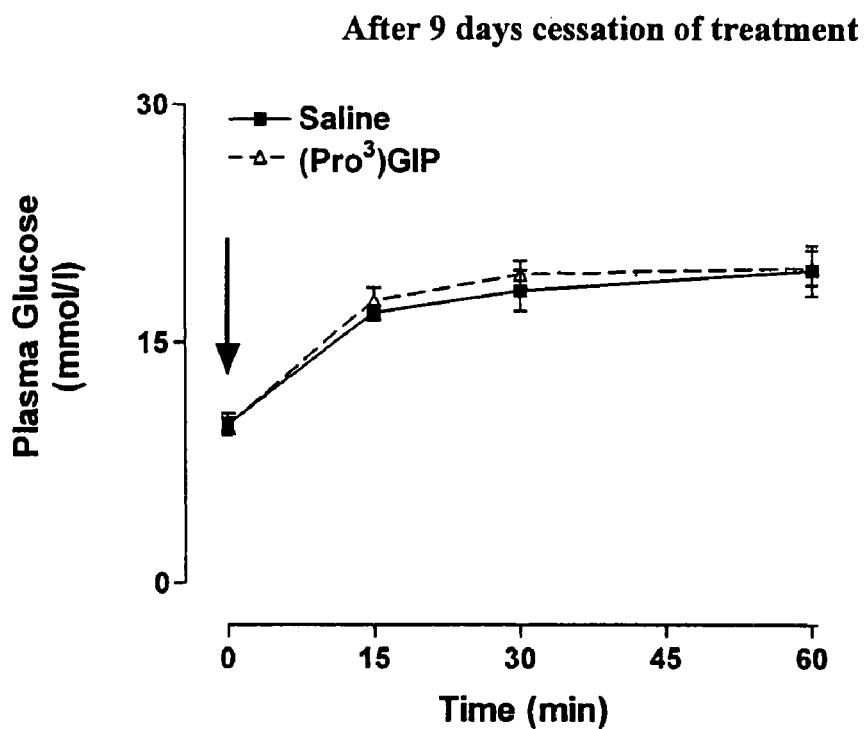
Figure 42:
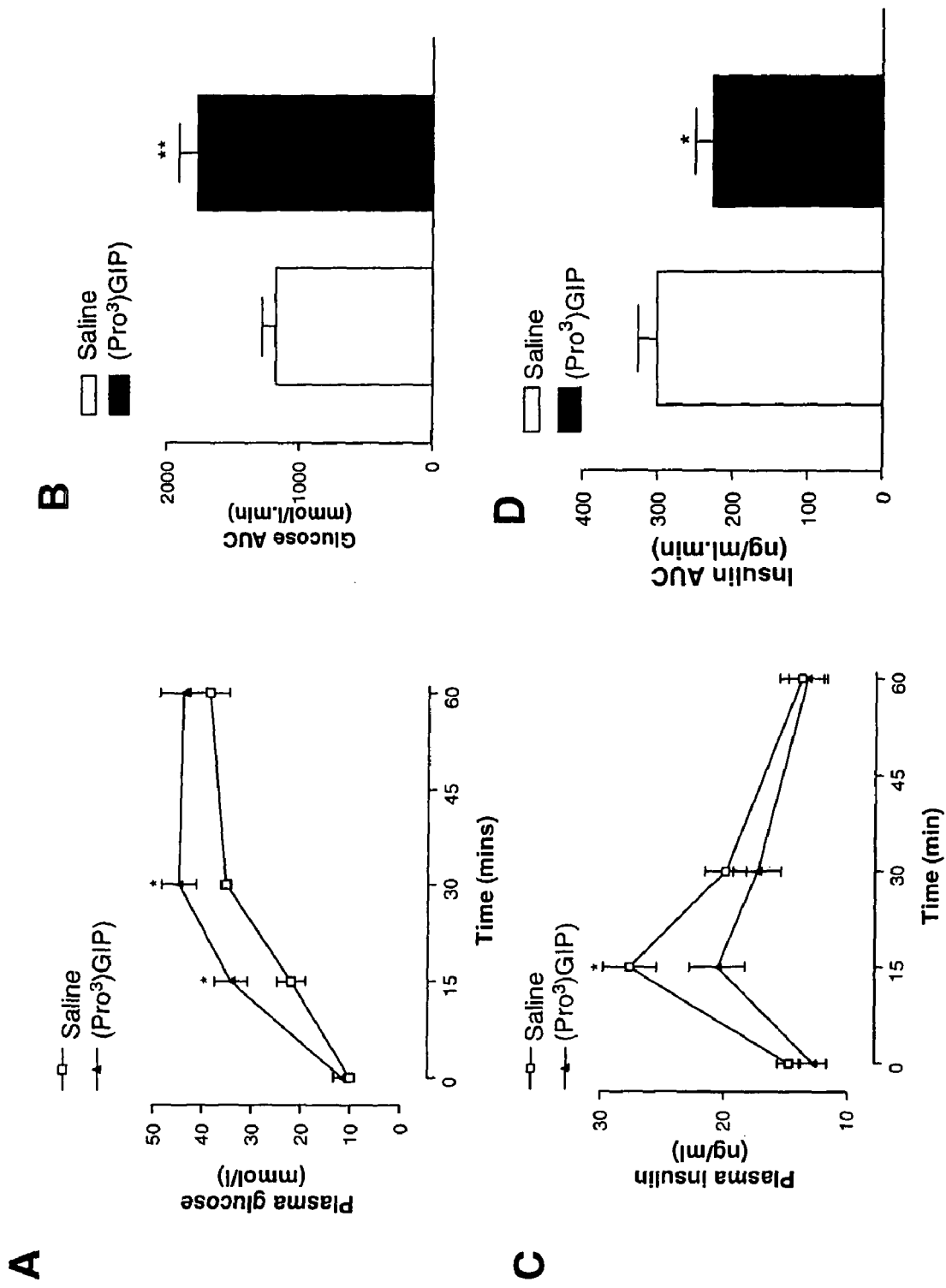
FIGS. 42A through 42D are a set of two line graphs (FIGS. 42A, 42C) and two bar graphs (FIGS. 42B, 42D) showing the effects of (Pro$^3$)GIP on plasma glucose and insulin response to native GIP 4 hours after administration.

FIGS. 41A and 41B are a pair of line graphs showing the effects of chronic administration of (Pro$^3$)GIP for 11 days on glucose tolerance in normal mice. Plasma glucose concentrations were measured prior to and after intraperitoneal administration of glucose (18 mmol/kg body weight). Arrow indicates time of injection (t=0). Values are means±SEM for 6 and *P<0.05, **P<0.01 compared to saline-treated group.

In total contrast to beneficial actions in ob/ob mice, chronic daily treatment of normal mice with (Pro$^3$)GIP (Δ) for 11 days resulted in a marked deterioration of glucose tolerance (FIG. 41A) relative to controls (■), which was reversed 9 days after cessation of treatment (FIG. 41B).

Example 5

Chemical Ablation of Gastric Inhibitory Polypeptide Receptor Action by Daily (Pro$^3$)GIP Administration Improves Glucose Tolerance and Ameliorates Insulin Resistance and Abnormalities of Islet Structure in Obesity-Diabetes Gastric inhibitory polypeptide (GIP) is an important incretin hormone secreted by endocrine K-cells in response to nutrient ingestion. This study investigated the effects of chemical ablation of GIP receptor (GIP-R) action on aspects of obesity-diabetes using a stable and specific GIP-R antagonist, (Pro$^3$)GIP. Young adult ob/ob mice received once daily i.p. injections of saline vehicle or (Pro$^3$)GIP over an 11-day period. Non-fasting plasma glucose levels and the overall glycemic excursion (AUC) to a glucose load were significantly reduced (1.6-fold; P<0.05) in (Pro$^3$)GIP-treated mice compared to controls. GIP-R ablation also significantly lowered overall plasma glucose (1.4-fold; P<0.05) and insulin (1.5-fold; P<0.05) responses to feeding. These changes were associated with significantly enhanced (1.6-fold; P<0.05) insulin sensitivity in the (Pro$^3$)GIP-treated group. Daily injection of (Pro$^3$)GIP reduced pancreatic insulin content (1.3-fold; P<0.05) and partially corrected the obesity-related islet hypertrophy and beta cell hyperplasia of ob/ob mice. These comprehensive beneficial effects of (Pro$^3$)GIP were reversed following 9 days cessation of treatment and were independent of food intake and body weight, which were unchanged. These studies highlight a role for GIP in obesity-related glucose intolerance and emphasize the potential of specific GIP-R antagonists as a new class of drugs for the alleviation of insulin resistance and treatment of type 2 diabetes.

Research Design and Methods

Animals. Obese diabetic (ob/ob) mice derived from the colony maintained at Aston University, UK (Bailey, C. J., et al., 1982, *Int. J. Obes.* 6:11-21) were used at 12-16 weeks of age. Animals were age-matched, divided into groups and housed individually in an air-conditioned room at 22±2° C. with a 12 hour light: 12 hour dark cycle. Drinking water and a standard rodent maintenance diet (Trouw Nutrition, Cheshire, UK) were freely available. All animal experiments were carried out in accordance with the UK Animals (Scientific Procedures) Act 1986. No adverse effects were observed following administration of (Pro$^3$)GIP.

Synthesis, purification and characterization of(Pro$^3$)GIP. (Pro$^3$)GIP was sequentially synthesized on an Applied Biosystems automated peptide synthesizer (Model 432 A). (Pro$^3$) GIP was purified by reversed-phase HPLC on a Waters Millenium 2010 chromatography system (Software version 2.1.5) and subsequently characterized using electrospray ionization mass spectrometry (ESI-MS).

Experimental protocols for ob/ob mouse studies. Initially, extended biological activity of (Pro$^3$)GIP was examined in 18-hour fasted ob/ob mice 4 hours after administration. Thereafter, over an 11-day period, mice received once daily i.p. injections (17:00 hours) of either saline vehicle (0.9% (w/v), NaCl) or (Pro$^3$)GIP (25 nmol/kg body wt). During a subsequent 9-day period, observations were continued following discontinuation of (Pro$^3$)GIP administration. Food intake and body weight were recorded daily whilst plasma glucose and insulin concentrations were monitored at intervals of 2-6 days. Whole blood for the measurement of glycated hemoglobin was taken on days 11 and 20. Intraperitoneal glucose tolerance (18 mmol/kg body wt), metabolic response to native GIP (25 nmol/kg body wt) and insulin sensitivity (50 U/kg body wt) tests were performed on days 11 and 20. Mice fasted for 18 hours were used to examine the metabolic response to 15 minutes feeding. In a separate series, pancreatic tissues were excised at the end of the 11-day treatment period or 9 days following discontinuation of (Pro$^3$) GIP and processed for immunohistochemistry or measurement of insulin following extraction with 5 ml/g of ice-cold acid ethanol (750 ml ethanol, 235 ml water, 15 ml concentrated HCl). Blood samples taken from the cut tip of the tail vein of conscious mice at the times indicated in the Figures were immediately centrifuged using a Beckman microcentrifuge (Beckman Instruments, UK) for 30 seconds at 13,000 g. The resulting plasma was then aliquoted into fresh Eppendorf tubes and stored at −20° C. prior to glucose and insulin determinations.

Biochemical analysis. Plasma glucose was assayed by an automated glucose oxidase procedure (Stevens, J. F., 1971, *Clin. Chem. Acta* 32:199-201) using a Beckman Glucose Analyzer II (Beckman Instruments, Galway, Ireland). Plasma and pancreatic insulin were assayed by a modified dextran-coated charcoal radioimmunoassay (Flatt, P. R. et al., 1981, *Diabetologia* 20:573-577). Glycated hemoglobin was determined using cation-exchange columns (Sigma, Poole, Dorset, UK) with measurement of absorbance (415 nm) in wash and eluting buffer using a VersaMax Microplate Spectrophotometer (Molecular Devices, Wokingham, Berkshire, UK).

Immunocytochemistry. Tissue fixed in 4% paraformaldehyde/PBS and embedded in paraffin was sectioned at 8 µm. After de-waxing, sections were incubated with blocking serum (Vector Laboratories, Calif., USA) prior to exposure to insulin antibody. Tissue samples were then incubated consecutively with secondary biotinylated universal, pan-specific antibody (Vector Laboratories, Calif., USA) and streptavidin/peroxidase preformed complex (Vector Laboratories, Calif., USA). Following washing, the stained pancreatic tissue was counterstained with hematoxylin (BDH Chemicals, Dorset, UK) and then plunged into acid methanol (500 ml methanol, 500 ml H$_2$O and 2.5 ml concentrated HCl) prior to dehydration and mounting in Depex (BDH Chemicals, Dorset, UK). The stained slides were viewed under a microscope (Nikon Eclipse E2000, Diagnostic Instruments Incorporated, Michigan, USA) attached to a JVC camera Model KY-F55B (JVC, London, UK) and analyzed using Kromoscan imaging software (Kinetic Imaging Limited, Faversham, Kent, UK). The average number and diameter of every islet in each section was estimated in a blinded manner using an eyepiece graticule calibrated with a stage micrometer (Graticules Limited, Tonbridge, Kent, UK). The longest and shortest diameters of each islet were determined with the graticule. Half of the sum of these two values was then considered to be the average islet diameter. Approximately 60-70 random sections were examined from the pancreas of each mouse.

Statistics. Results are expressed as mean±SEM. Data were compared using ANOVA, followed by a Student-Newman-Keuls post hoc test. Area under the curve (AUC) analyzes were calculated using the trapezoidal rule with baseline subtraction (Burington, R. S., *Handbook of Mathematical Tables and Formulae*, New York, McGraw-Hill, 1973). P<0.05 was considered to be statistically significant.

Results

Effects of (Pro$^3$)GIP on plasma glucose and insulin concentrations 4 hours after administration were examined. The results are shown in FIGS. 42A through 42D, which are a set of two line graphs (FIGS. 42A, 42C) and two bar graphs (FIGS. 42B, 42D) showing the effects of (Pro$^3$)GIP on plasma glucose and insulin response to native GIP 4 hours after administration. Tests were conducted 4 hours after administration of (Pro$^3$)GIP (25 nmoles/kg body weight) or saline (0.9% NaCl) in 18 hour-fasted ob/ob mice. Plasma glucose and insulin concentrations were measured prior to and after i.p. administration of glucose (18 mmoles/kg body weight) in combination with native GIP (25 nmoles/kg body weight). The incremental area under the glucose or insulin curves (AUC) between 0 and 60 min are shown in the right panels. Values represent means±SEM for 8 mice. *P<0.05 and **P<0.01 compared with saline alone group.

As shown in FIGS. 42A through 42D, administration of (Pro$^3$)GIP for 4 hours previously impaired the plasma glucose and insulin responses to native GIP, given together with glucose. AUC glucose and insulin values were increased by 151% (P<0.05) and decreased by 25% (P<0.05); respectively, compared with saline-treated controls. This supports a protracted biological half-life and forms the basis of the once-daily injection.

The effects of (Pro$^3$)GIP on food intake, body weight and non-fasting plasma glucose and insulin concentrations were studied. The results are shown in FIGS. 43A through 43D, which are a set of two line graphs and two bar graphs showing the effects of daily (Pro$^3$)GIP administration on food intake (FIG. 43A), body weight (FIG. 43B), plasma glucose (FIG. 43C) and insulin (FIG. 43D) concentrations in ob/ob mice. Parameters were measured for 5 days prior to, 11 days during (indicated by black bar) and 9 days after treatment with saline or (Pro$^3$)GIP (25 nmol/kg bw/day). Values are mean±SEM for eight mice. *P<0.05 compared with saline group.

Figure 43:
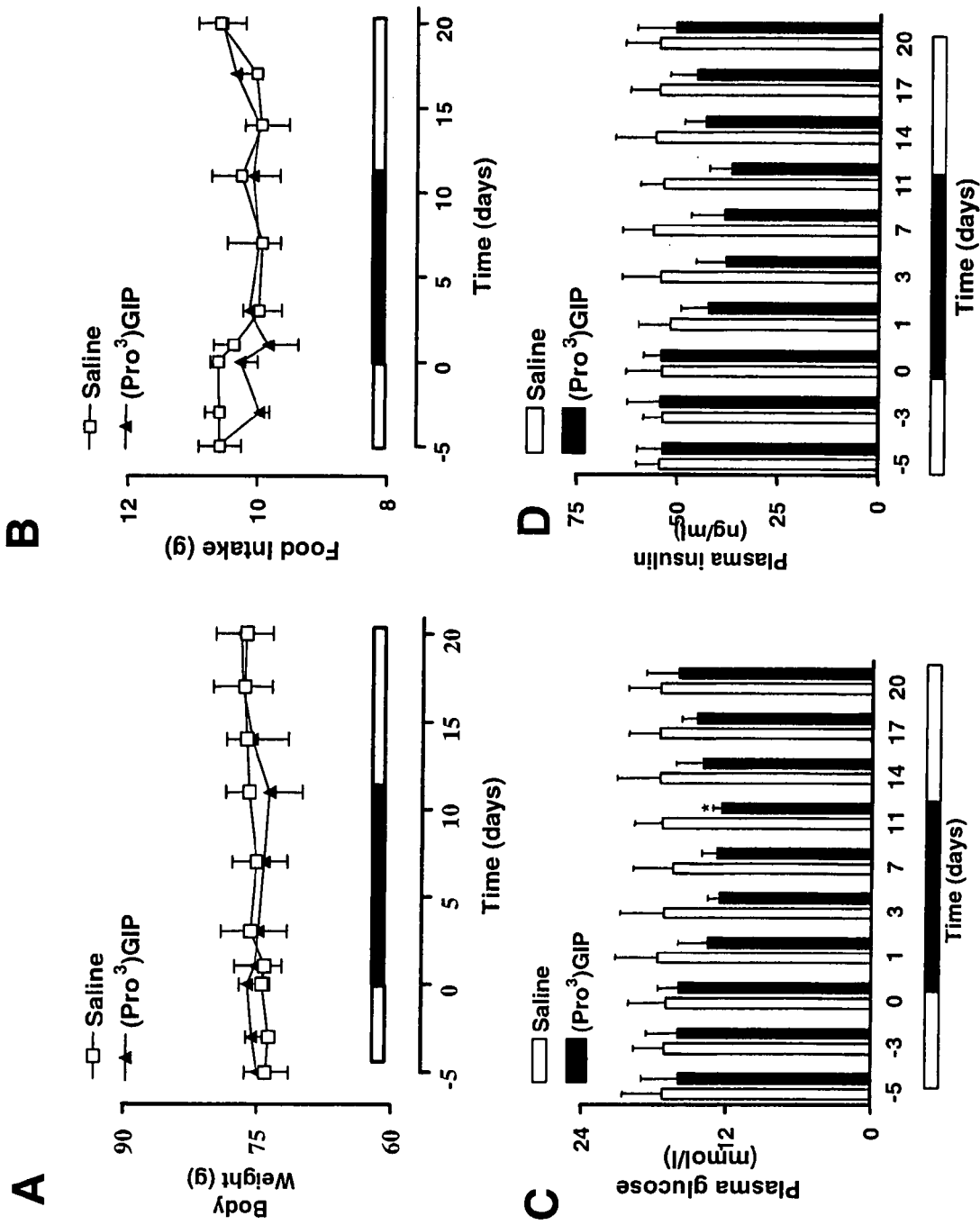
FIGS. 43A through 43D are a set of two line graphs and two bar graphs showing the effects of daily (Pro$^3$)GIP administration on food intake (FIG. 43A), body weight (FIG. 43B), plasma glucose (FIG. 43C) and insulin (FIG. 43D) concentrations in ob/ob mice.

Administration of (Pro$^3$)GIP had no effect on food intake and body weight (FIGS. 43A and 43B). On day 11, plasma glucose had declined to significantly reduced (P<0.05) concentrations in ob/ob mice receiving (Pro$^3$)GIP (FIG. 43C). Cessation of treatment returned plasma glucose concentrations towards control levels. Consistent with this pattern, glycated hemoglobin was significantly lower (P<0.05) after 11 days treatment with (Pro$^3$)GIP than either before or 9 days following cessation of daily injection (8.0±0.3%, 6.9±0.2%, 7.7±0.4%, respectively). No significant changes in plasma insulin levels were noted during or after the treatment period. However, there was a general trend for plasma insulin concentrations to decrease progressively during (Pro$^3$)GIP treatment (FIG. 43D).

The effects of (Pro$^3$)GIP on glucose tolerance are shown in FIGS. 44A through 44D, which are a set of four line graphs with inset bar graphs showing the effects of daily (Pro$^3$)GIP administration on glucose tolerance and plasma insulin response to glucose in ob/ob mice. Tests were conducted after daily treatment with (Pro$^3$)GIP (25 nmoles/kg body weight/day; ▲; black bars) or saline (control; □; white bars) for 11 days (FIG. 44A, 44C) or 9 days after cessation of treatment (FIG. 44B, 44B). Glucose (18 mmoles/kg body weight) was administered at the time indicated by the arrow. Plasma glucose (FIG. 44A, 44B) and insulin (FIG. 44C, 44D) AUC values for 0-60 minutes post injection, with identical baseline subtractions in each case to demonstrate the complete effect of (Pro$^3$)GIP treatment, are shown in insets. Values are mean±SEM for eight mice. *P<0.05, P<0.01 and *P<0.001 compared with saline group.

Figure 44:
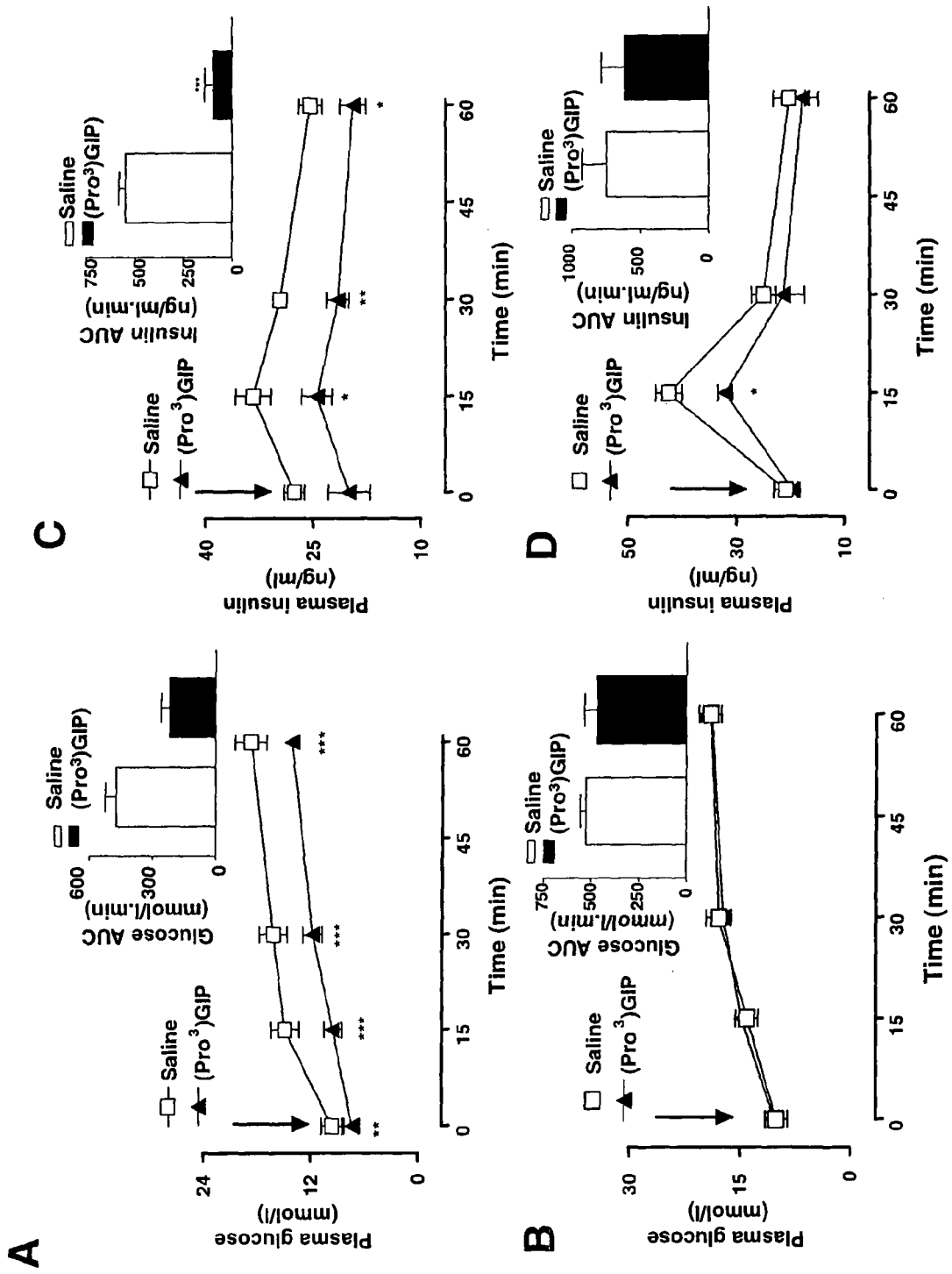
FIGS. 44A through 44D are a set of four line graphs with inset bar graphs showing the effects of daily (Pro$^3$)GIP administration on glucose tolerance and plasma insulin response to glucose in ob/ob mice.

Daily administration of (Pro$^3$)GIP for 11 days resulted in significantly reduced (P<0.001) plasma glucose concentrations at 15, 30 and 60 minutes following intraperitoneal glucose (FIG. 44A). This was corroborated by a significantly decreased 0-60 minutes AUC value (FIG. 44A) which was 2.1-fold reduced (P<0.01) compared to controls. Plasma insulin concentrations were also significantly (P<0.05) reduced 15, 30 and 60 minutes following intraperitoneal glucose injection in the (Pro$^3$)GIP treated group (FIG. 44A). AUC, 0-60 minutes values were also significantly decreased (P<0.001). Interestingly, an almost identical pattern was observed when 11 day treated ob/ob mice were administered glucose together with native GIP (25 nmoles/kg body weight) (data not shown). This supports the view that GIP action was effectively antagonized in the (Pro$^3$)GIP treated group. Discontinuation of (Pro$^3$)GIP treatment for 9 days (day 20 of study) resulted in almost identical plasma glucose and insulin responses to intraperitoneal glucose (FIG. 44), with lower glucose-mediated plasma insulin concentrations noted at one time point (15 minutes; P<0.05).

Figure 45:
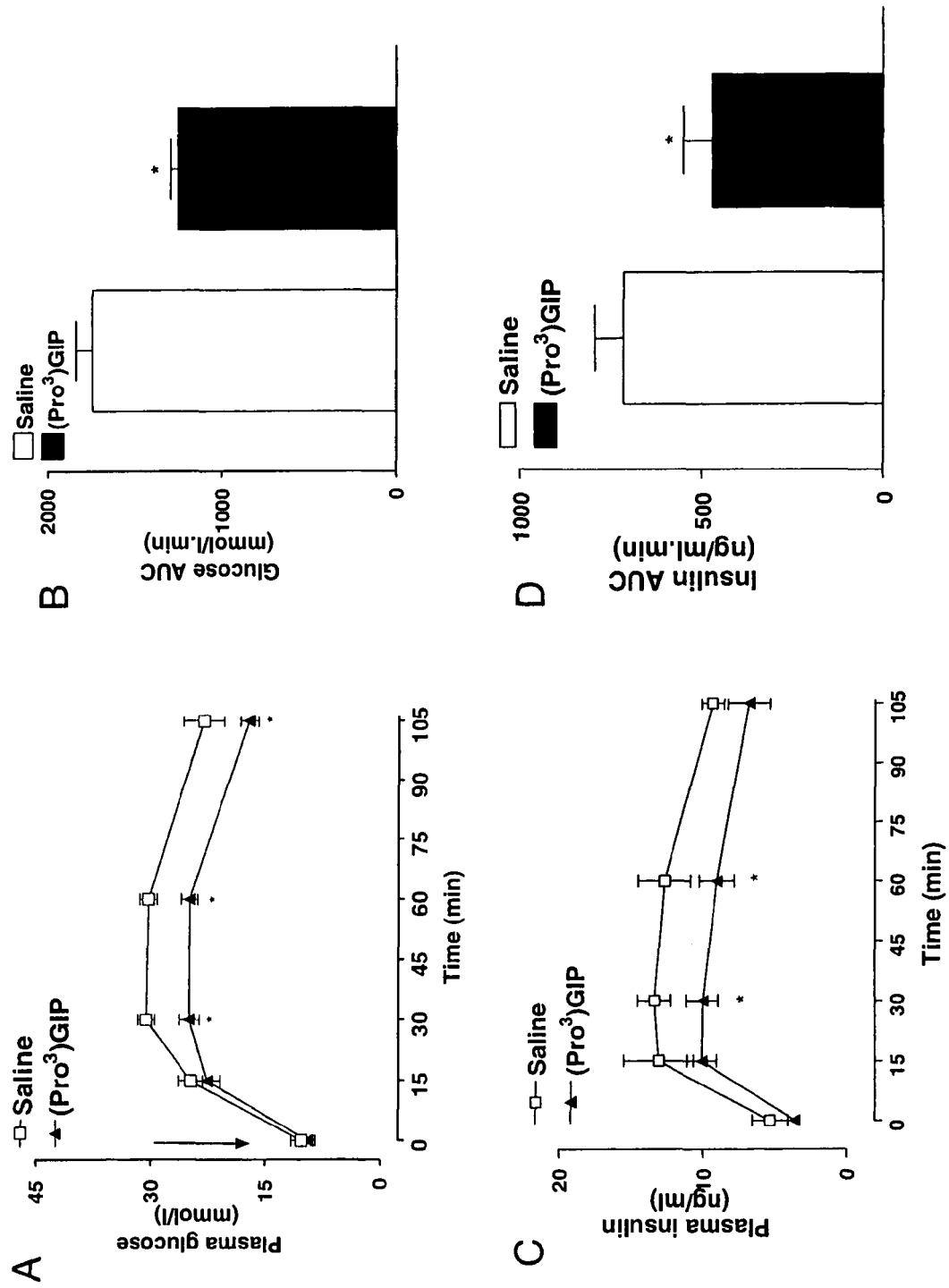
FIGS. 45A through 45D are a set of two line graphs (FIGS. 45A, 45C) and two bar graphs (FIGS. 45B, 45D) showing the effects of daily (Pro$^3$)GIP administration (▲; black bars) or saline (□; white bars) on glucose (FIGS. 45A, 45B) and insulin (FIGS. 45C, 45D) responses to feeding in ob/ob mice fasted for 18 hours.
Figure 46:
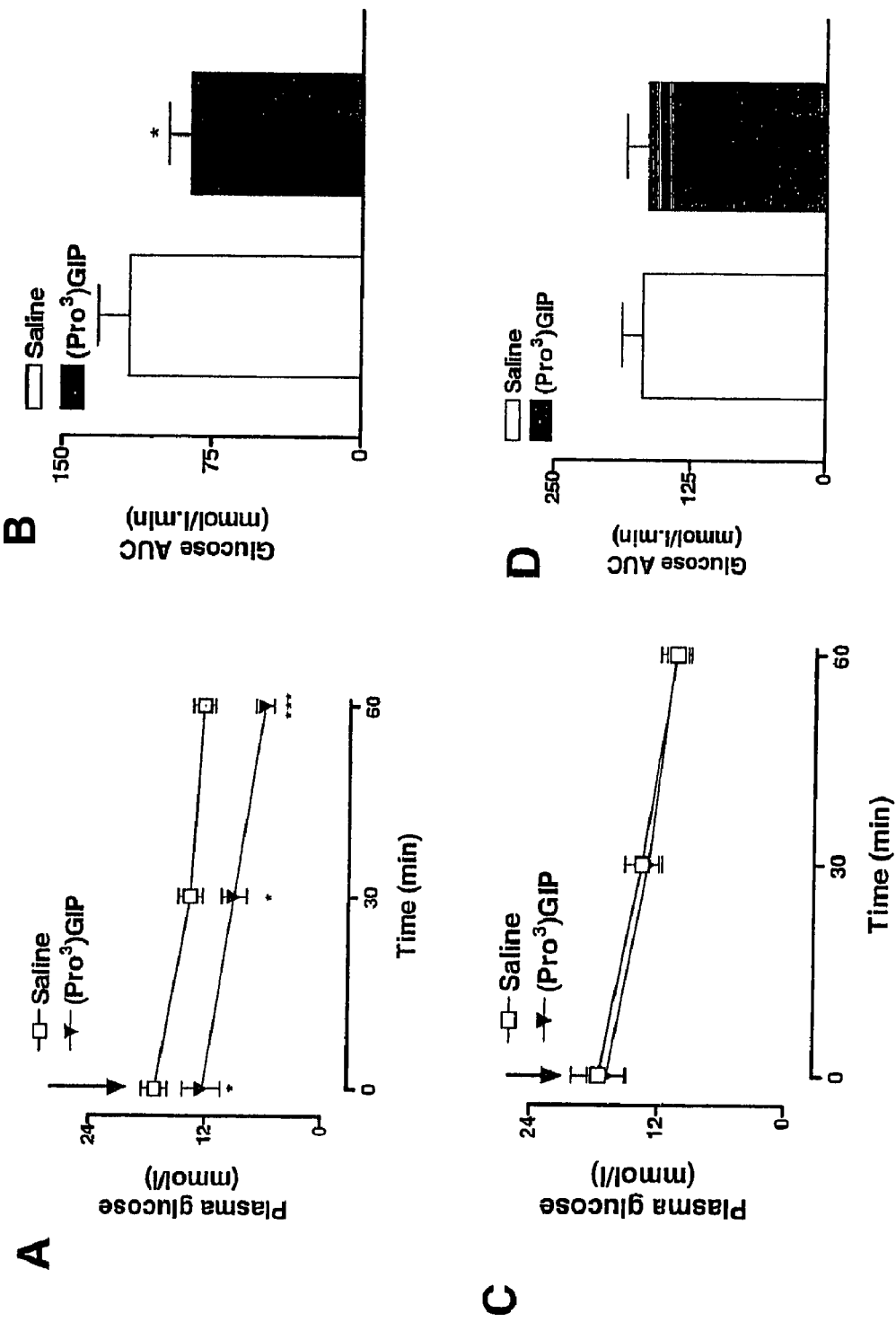
FIGS. 46A through 46D are a set of two line graphs (FIGS. 46A, 46C) and two bar graphs (FIGS. 46B, 46D) showing the effects of daily (Pro$^3$)GIP administration on insulin sensitivity in ob/ob mice.

The effects of (Pro$^3$)GIP on metabolic response to feeding and insulin sensitivity are shown in FIGS. 45 and 46. FIGS. 45A through 45D are a set of two line graphs (FIGS. 45A, 45C) and two bar graphs (FIGS. 45B, 45D) showing the effects of daily (Pro$^3$)GIP administration (▲; black bars) or saline (□; white bars) on glucose (FIGS. 45A, 45B) and insulin (FIGS. 45C, 45D) responses to feeding in ob/ob mice fasted for 18 hours. Tests were conducted after daily treatment with (Pro$^3$)GIP (25 nmol/kg body weight/day) or saline for 11 days. The arrow indicates the time of feeding (15 minutes). AUC values for 0-105 minutes post-feeding are also shown. Values are mean±SEM for eight mice. *P<0.05 compared with saline group.

FIGS. 46A through 46D are a set of two line graphs (FIGS. 46A, 46C) and two bar graphs (FIGS. 46B, 46D) showing the effects of daily (Pro$^3$)GIP administration on insulin sensitivity in ob/ob mice. Tests were conducted after daily treatment with (Pro$^3$)GIP (25 nmol/kg body weight/day; ▼; black bars) or saline (□; white bars) for 11 days (FIG. 46A, 46B) or 9 days after cessation of treatment (FIG. 46C, 46D). Insulin (50 U/kg body weight) was administered by intraperitoneal injection at the time indicated by the arrow. AUC values for 0-60 minutes post-injection are also shown. Values are mean±SEM for eight mice. *P<0.05 compared with saline group.

Plasma glucose and insulin responses to 15 minutes feeding were significantly lowered (P<0.05) at 30 and 60 minutes in ob/ob mice treated with (Pro$^3$)GIP for 11 days (FIG. 45). Similarly, AUC glucose and insulin were significantly (P<0.05) decreased in (Pro$^3$)GIP treated ob/ob mice, despite similar food intakes of 0.3-0.5 g/mouse/15 minutes. As shown in FIGS. 46A and 45B, the hypoglycemic action of insulin was significantly (P<0.05) augmented in terms of AUC measures and post injection values in ob/ob mice treated with (Pro$^3$)GIP for 11 days. The responses following 9 days discontinuation of (Pro$^3$)GIP treatment were similar to saline treated controls (FIG. 45C, 45D).

The effects of (Pro$^3$)GIP on pancreatic insulin and islet morphology are shown in FIGS. 47A through 47D, and 48A through 48F. FIGS. 47A through 47D are a set of four bar graphs showing the effects of daily (Pro$^3$)GIP administration on pancreatic weight (FIG. 47A), insulin content (FIG. 47B), islet number (FIG. 47C) and islet diameter (FIG. 47D) in ob/ob mice. Parameters were measured after daily treatment with (Pro$^3$)GIP (25 nmol/kg body weight/day; black bars) or saline (white bars) for 11 days and 9 days after cessation of treatment (day 20). Values are mean±SEM for eight mice. *P<0.05 and ***P<0.001 compared with saline group. FIGS. 48A through 48F are a set of two bar graphs (FIGS. 48A, 48D) and four photomicrographs (FIGS. 48B, 48C, 48E, 48F), showing the effects of daily (Pro$^3$)GIP administration on islet size and morphology in ob/ob)mice.

Figure 47:
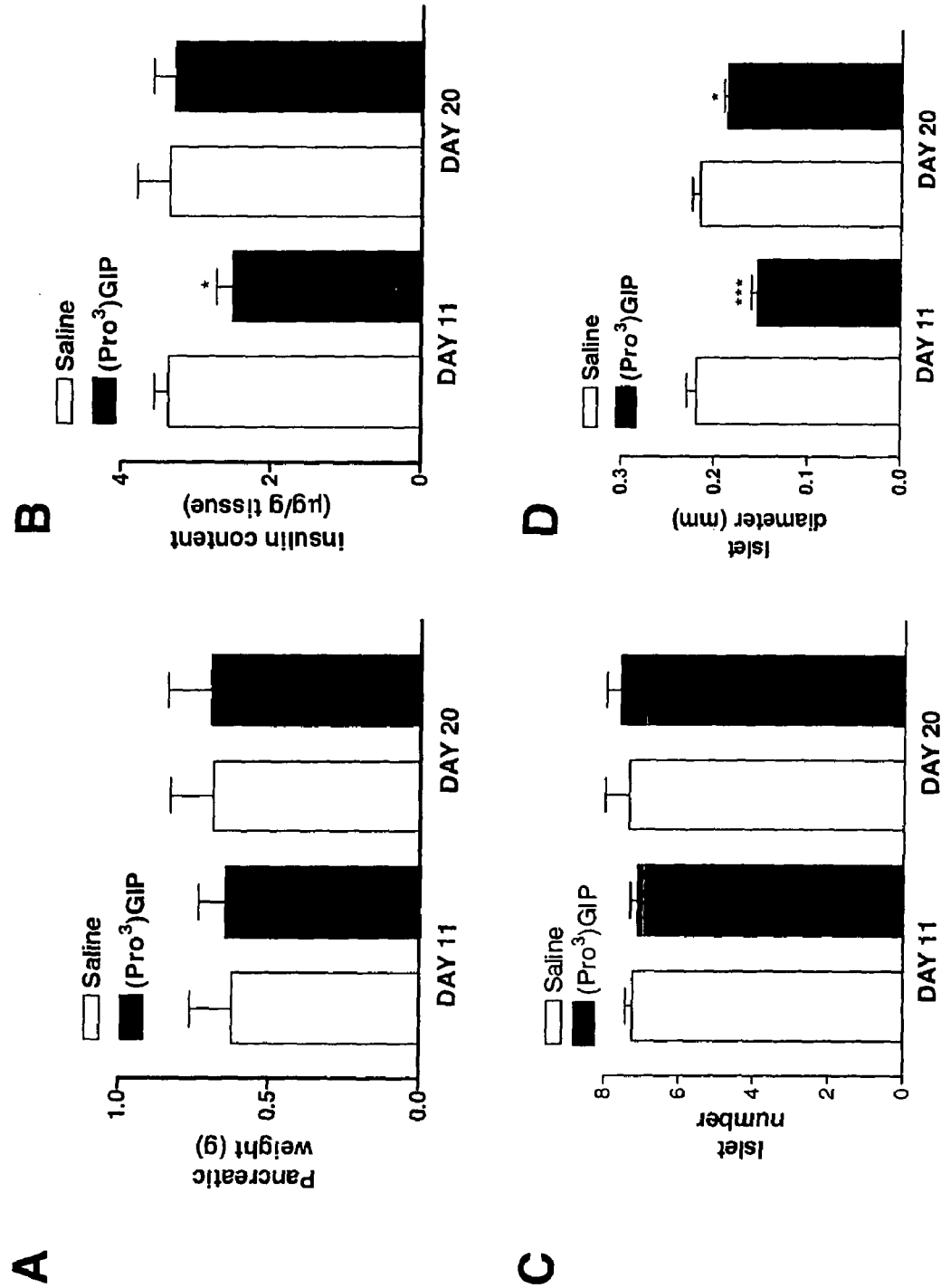
FIGS. 47A through 47D are a set of four bar graphs showing the effects of daily (Pro$^3$)GIP administration on pancreatic weight (FIG. 47A), insulin content (FIG. 47B), islet number (FIG. 47C) and islet diameter (FIG. 47D) in ob/ob mice.

(Pro$^3$)GIP treatment had no effect on pancreatic weight (FIG. 47A). However, pancreatic insulin content was significantly (P<0.05) decreased in ob/ob mice receiving (Pro$^3$)GIP for 11 days compared to controls (FIG. 47B). No significant differences were observed in islet number per pancreatic section (FIG. 47C), but average islet diameter was markedly and significantly reduced (P<0.001) in (Pro$^3$)GIP treated ob/ob mice (FIG. 47D). These effects were effectively reversed by discontinuation of (Pro$^3$)GIP on day 20, however average islet diameter was still significantly reduced (P<0.05). As shown in FIG. 48A, more detailed analysis revealed that the reduction is islet diameter on day 11 was due to a significant decrease (P<0.001) in the percentage of larger diameter (>0.15 mm) islets with increases in the proportion of islets with small (<0.10 mm) and medium (0.1-0.15 mm) diameters. FIG. 48D presents similar analysis following cessation of treatment, with a significant (P<0.05) increase in the percentage of small islets still apparent. Representative images (×40 magnification) of pancreata immunohistologically stained for insulin from 11-day (Pro$^3$)GIP treated ob/ob mice (FIG. 48B) and saline treated controls (FIG. 48C) illustrate the dramatic changes in pancreatic islet morphology induced by (Pro$^3$)GIP treatment. Pancreata immunohistologically stained for insulin on day 20 are also shown (FIG. 48E, 48F).

Parameters were measured after daily treatment with (Pro$^3$)GIP (25 nmol/kg body weight/day) or saline for 11 days (FIG. 48A) and 9 days after cessation of treatment (FIG. 48D). Proportion of islets classified as large (>0.15 mm) diameter, medium (0.1-0.15 mm) diameter and small (<0.1 mm) diameter are shown. Values are mean±SEM for eight mice FIGS. 48B, 48C, 48E and 48F are representative images (×40 magnification) of pancreata stained for insulin following 11 days treatment with (Pro$^3$)GIP (FIG. 48B) or saline (FIG. 48C). Corresponding images 9 days after cessation of treatment with (Pro$^3$)GIP (FIG. 48E) or saline (FIG. 48F) are also shown. The arrows indicate islets.

Example 6

N-Terminally Acetylated and Ly$^{16}$ and Lys$^{37}$-Substituted GIP

This example examines the metabolic stability, biological activity and antidiabetic potential of fatty acid derivatized N-terminally modified GIP analogues. These are N-AcGIP (LysPAL$^{16}$) and N-AcGIP(LysPAL$^{37}$), which have an N-terminal Tyr$^1$ acetyl group, and a C-16 palmitate group linked to the epsilon-amino group of the lysine at either position 16 or position 37 of the GIP protein.

Materials and Methods

Animals. Obese diabetic (ob/ob) mice derived from the colony maintained at Aston University, UK were used at 12-17 weeks of age. The genetic background and characteristics of the colony used have been outlined in detail elsewhere (Bailey, C. J. et al., 1982, *Int. J. Obesity* 6:11-21; Gault, V. A. et al., 2003, *J. Endocrinol.* 176: 133-141). Animals were housed in an air-conditioned room at 22±2° C. with a 12 hours light: 12 hours dark cycle. Drinking water and standard rodent maintenance diet (Trouw Nutrition, Cheshire, UK) were freely available. All test solutions were administered by i.p. injection in a final volume of 5 ml/kg bw. Blood was collected from the cut tip of the tail vein of conscious mice into chilled fluoride/heparin microcentrifuge tubes immediately prior to injection and at the times indicated in the Figures. Plasma was separated using a Beckman microcentrifuge (Beckman Instruments, UK) at 13,000 g for 30 second and stored at −20° C. prior to glucose and insulin determinations. All animal experiments were carried out in accordance with the UK Animals (Scientific Procedures) Act 1986. No adverse effects were observed following acute or long-term administration of any of the peptides.

Materials. High performance liquid chromatography (HPLC) grade acetonitrile was obtained from Rathburn (Walkersburn, UK). Trifluoroacetic acid (TFA) and trichloroacetic acid (TCA) were obtained from Aldrich (Poole, Dorset, UK). DPP IV, isobutylmethylxanthine (IBMX), alpha-cyano-4-hydroxycinnamic acid, cyclic AMP and ATP were all purchased from Sigma (Poole, Dorset, UK). Fmoc-protected amino acids were from Calbiochem Novabiochem (Nottingham, UK). RPMI-1640 and DMEM tissue culture medium, foetal bovine serum, penicillin and streptomycin were all purchased from Gibco (Paisley, Strathclyde, UK). The chromatography columns used for cyclic AMP assay, Dowex AG50 WX and neutral alumina AG7 were obtained from Bio-Rad (Life Science Research, Alpha Analytical, Larne, UK). All water used in these experiments was purified using a Milli-Q Water Purification System (Millipore, Milford, Mass., USA). All other chemicals used were of the highest purity available.

Synthesis, purification and characterisation of GIP and related analogues. Native GIP was sequentially synthesised using standard solid-phase Fmoc peptide chemistry (ABI 432A Peptide Synthesiser) as described previously (O'Harte, F. P. M. et al., 2002, *Diabetologia* 45: 1281-1291). N-AcGIP (LysPAL$^{16}$) and N-AcGIP(LysPAL$^{37}$) were synthesised in the same way as native GIP but with the exception that the epsilon-amino groups of Lys at positions 16 or 37 were conjugated with a C-16 palmitate fatty acid. In addition, an acetyl adduct was incorporated at the N-terminal Tyr$^1$. The synthetic peptides were judged pure by reversed-phase HPLC on a Waters Millenium 2010 chromatography system (Software version 2.1.5) and subsequently characterised using matrix assisted laser desorption ionisation-time of flight mass spectrometry (MALDI-TOF MS) as described previously (Gault, V. A. et al., 2002, *Cell. Biol. Int.* 27: 41-46).

DPP IV degradation studies. GIP and fatty acid derivatised GIP analogues were incubated at 37° C. with purified porcine dipeptidylpeptidase IV (5 mU in 50 mmol/l triethanolamine-HCl; pH 7.8) for 0, 2, 4, 8 and 24 hours (final peptide concentration 2 mmol/l). The reactions were subsequently terminated by addition of 10% (v/v) TFA/water and the reaction products separated using HPLC. Reaction products were applied to a Vydac C-4 column (4.6×250 mm; The Separations Group, Hesparia, Calif.) and the major degradation product GIP(3-42) separated from intact GIP. The column was equilibrated with 0.12% (v/v) TFA/water at a flow rate of 1.0 ml/minute using 0.1% (v/v) TFA in 70% acetonitrile/water with the concentration of acetonitrile in the eluting solvent being raised from 0% to 40% over 10 minutes, and then from 40% to 75% over 35 minutes. The absorbance was monitored at 206 nm using a SpectraSystem UV 2000 Detector (Thermoquest Limited, Manchester, UK) and the peaks collected manually prior to MALDI-ToF MS analysis. HPLC peak area data were used to calculate % intact peptide remaining throughout the incubation.

Cells and cell culture. Chinese hamster lung (CHL) fibroblasts stably transfected with the human GIP receptor (Gremlich, S. et al., 1995, *Diabetes* 44: 1202-1208) were cultured in DMEM tissue culture medium containing 10% (v/v) FBS, 1% (v/v) antibiotics (100 U/ml penicillin, 0.1 mg/ml streptomycin). Clonal pancreatic BRIN-BD11 cells (McClenaghan, N. H. et al., 1996, *Diabetes* 45: 1132-1140) were cultured using RPMI-1640 culture medium containing 10% (v/v) FBS, 1% (v/v) antibiotics (100 U/ml penicillin, 0.1 mg/ml streptomycin) and 11.1 mmol/l glucose. Cells were maintained at 37° C. in an atmosphere of 5% $CO_2$ and 95% air using an LEEC incubator (Laboratory Technical Engineering, Nottingham, UK).

In vitro biological activity. Intracellular cyclic AMP production was measured using GIP-receptor transfected CHL fibroblasts (O'Harte, F. P. M. et al., 2002, *Diabetologia* 45: 1281-1291). In brief, CHL cells were seeded into 12-well plates (Nünc, Roskilde, Denmark) at a density of 10$^5$ cells per well and allowed to grow for 48 hours before being loaded with tritiated adenine (2 µCi; TRK311; Amersham, Buckinghamshire, UK). The cells were then incubated at 37° C. for 6 hours in 1 ml DMEM supplemented with 0.5% (w/v) BSA and subsequently washed twice with HBS buffer (pH 7.4). Cells were then exposed to GIP/GIP analogues ($10^{-13}$ to $10^{-6}$ mol/l) in HBS buffer in the presence of 1 mmol/l IBMX for 15 minutes at 37° C. The medium was subsequently removed and the cells lysed with 1 ml of 5% TCA containing 0.1 mmol/l unlabelled cyclic AMP and 0.1 mmol/l unlabelled ATP. The intracellular cyclic AMP was then separated on Dowex and alumina exchange resins as described previously (O'Harte, F. P. M. et al., 2002, *Diabetologia* 45: 1281-1291).

Insulin-release studies were carried out using clonal pancreatic BRIN-BD11 cells as described previously (O'Harte, F. P. M. et al., 2002, *Diabetologia* 45: 1281-1291). Briefly, BRIN-BD11 cells were seeded into 24-well plates at a density of $10^5$ cells per well, and allowed to attach overnight at 37° C. Acute tests for insulin release were preceded by 40 minutes pre-incubation at 37° C. in 1.0 ml Krebs Ringer bicarbonate buffer supplemented with 1.1 mmol/l glucose. Test incubations were performed in the presence of 5.6 mmol/l glucose with a range of concentrations ($10^{-13}$ to $10^{-6}$ mol/l) of GIP and GIP analogues. After 20 minutes incubation, the buffer was removed from each well and aliquots (200 µl) used for measurement of insulin.

Effects of N-AcGIP(LysPAL[16]) and N-AcGIP(LysPAL[37]) in ob/ob mice. Metabolic and dose-response effects of GIP and N-AcGIP(LysPAL) analogues (at 6.25-25 nmoles/kg bw) following glucose administration (18 mmoles/kg bw) were examined in mice fasted for 18 hours. To evaluate long-term effects, groups of ob/ob mice received once daily intraperitoneal injections (17:00 h) for 14 days of either saline vehicle (0.9%, w/v, NaCl), native GIP or N-AcGIP(LysPAL[37]) (both at 12.5 nmoles/kg body weight/day). Food intake and body weight were recorded daily. Plasma glucose and insulin concentrations were monitored at 2-6 day intervals. At 14 days, groups of animals were used to evaluate intraperitoneal glucose tolerance (18 mmoles/kg) and insulin sensitivity (50 U/kg). In a separate series, two experimental protocols were employed to examine the possibility of GIP receptor desensitization after 14 days treatment. Acute metabolic effects of the usual injection of either saline, GIP or N-AcGIP(LysPAL[37]) were monitored when administered together with glucose (18 mmoles/kg). In the second, acute effects of N-AcGIP(LysPAL[37]) given together with glucose were examined in all 3 groups of mice. At the end of the 14-day treatment period, pancreatic tissues were excised for measurement of insulin following extraction with 5 ml/g ice-cold acid ethanol (75% ethanol, 2.35% H2O, 1.5% HCl). Whole blood was taken for determination of glycated hemoglobin.

Biochemical analyses. Plasma glucose was assayed by an automated glucose oxidase procedure (Stevens, J. F., 1971, *Clin. Chem. Acta* 32:199-201) using a Beckman Glucose Analyser II (Beckman, Galway, Ireland). Plasma insulin was determined by dextran-charcoal RIA as described previously (Flatt, P. R. et al., 1981, *Diabetologia* 20: 573-577). Glycated hemoglobin was determined using cation-exchange columns (Sigma, Poole, Dorset, UK) with measurement of absorbance (415 nm) in wash and eluting buffers using a VersaMax microplate spectrophotometer (Molecular Devices, Wokingham, Berkshire, UK).

Statistics. Results are expressed as mean±SEM. Data were compared using the unpaired Student's t-test. Where appropriate, data were compared using repeated measures ANOVA or one-way ANOVA, followed by the Student-Newman-Keuls post hoc test. Incremental areas under plasma glucose and insulin curves (AUC) were calculated using a computer-generated program employing the trapezoidal rule (Burington, R. S., 1973, *Handbook of Mathematical Tables and Formulae*, McGraw-Hill, New York) with baseline subtraction. Groups of data were considered to be significantly different if $p<0.05$.

Results

Structural characterisation by MALDI-ToF MS. Following synthesis and HPLC purification, the molecular masses were obtained for GIP, N-AcGIP(LysPAL[16]) and N-AcGIP(LysPAL[37]) using MALDI-ToF MS (Table 3, below). The mass-to-charge (m/z) ratio for native GIP was calculated to be 4983.7 Da, corresponding very closely to the theoretical mass of 4982.4 Da. Similarly, the m/z ratios for N-AcGIP(LysPAL[16]) and N-AcGIP(LysPAL[37]) were 5268.9 Da and 5267.7 Da, respectively. These values correlate very closely to the theoretical mass (5266.1 Da), therefore, confirming the correct structures for each of the synthetic peptides.

TABLE 3

Structural characterisation of GIP and GIP analogues by MALDI-ToF MS.

| Peptide | Experimental $M_r$ (Da) | Theoretical $M_r$ (Da) | Difference (Da) |
| --- | --- | --- | --- |
| GIP | 4983.7 | 4982.4 | 1.3 |
| N-AcGIP(LysPAL[16]) | 5268.9 | 5266.1 | 2.8 |
| N-AcGIP(LysPAL[37]) | 5267.7 | 5266.1 | 1.6 |

Peptide samples were mixed with matrix (alpha-cyano-4-hydroxycinnamic acid) and m/z ratio vs. relative peak intensity recorded using a Voyager-DE BioSpectrometry Workstation.

Degradation by DPP IV. Table 4, below, illustrates the % intact peptide remaining after incubation with DPP IV. Degradation of native GIP was evident after just 2 hours with only 52±3% of the peptide remaining intact. After 8 hours incubation the native peptide was entirely degraded to GIP(3-42). In contrast, both N-AcGIP(LysPAL[16]) and N-AcGIP(LysPAL[37]) remained completely intact (no degradation fragment evident) even after 24 hours incubation with DPP IV.

TABLE 4

Percentage intact peptide remaining after incubation with DPP IV.

| | % Intact peptide remaining after time (hours) | | | |
| --- | --- | --- | --- | --- |
| Peptide | 0 | 2 | 8 | 24 |
| Native GIP | 100 | 52 ± 3 | 0 | 0 |
| N-AcGIP(LysPAL1[16]) | 100 | 100 | 100 | 100 |
| N-AcGIP(LysPAL[37]) | 100 | 100 | 100 | 100 |

Values represent the % intact peptide remaining relative to the major degradation product GIP(3-42) following incubation with DPP IV as determined from HPLC peak area data. The reactions were performed in triplicate and the means±SEM values calculated.

Changes in Cyclic AMP production. FIG. 50A shows intracellular cyclic AMP production by GIP (▲) and fatty acid derivatised GIP analogues N-AcGIP(LysPAL[16]) (□) and N-AcGIP(LysPAL[37]) (●), as determined by column chromatography, in CHL cells stably expressing the human GIP receptor. Each experiment was performed in triplicate (n=3) and the results expressed (means±SEM) as a percentage of the maximum GIP response.

A concentration-dependent ($10^{-13}$ to $10^{-6}$ mol/l) increase in cyclic AMP production was observed with native GIP ($EC_{50}$ value 18.2 nmol/l) using CHL cells transfected with the human GIP receptor (FIG. 50A). Likewise, both N-AcGIP (LysPAL$^{16}$) and N-AcGIP(LysPAL$^{37}$) followed a similar pattern of stimulation to that of native GIP with calculated EC$_{50}$ values of 12.1 and 13.0 nmol/l, respectively. The lower EC$_{50}$ values for both analogues suggest an enhanced cyclic AMP-stimulating potency.

In vitro insulin-releasing activity. FIG. 50B shows insulin-releasing activity of glucose (5.6 mmo/l glucose; white bars), GIP (lined bars) and fatty acid derivatised GIP analogues N-AcGIP(LysPAL$^{16}$) (grey bars) and N-AcGIP(LysPAL$^{37}$) (black bars) in the clonal pancreatic beta cell line, BRIN-BD11. After a pre-incubation (40 minutes), the effects of various concentrations of peptide were tested on insulin-release during a 20 minutes incubation. Values are means±SEM for 8 separate observations. *$p<0.05$, $p<0.01$, *$p<0.001$ compared to control (5.6 mmol/l glucose alone).

Consistent with its role as a potent insulinotropic hormone, native GIP dose-dependently stimulated insulin secretion ($p<0.01$ to $p<0.001$) compared to control (5.6 mmol/l glucose alone) (FIG. 50B). Likewise, both N-AcGIP(LysPAL$^{16}$) and N-AcGIP(LysPAL$^{37}$) significantly stimulated glucose-induced insulin secretion ($p<0.05$ to $p<0.001$). On the basis of cyclic AMP and insulin secretory data, both GIP analogues appear to be at least equipotent to the native peptide.

Metabolic effects in ob/ob mice. FIGS. 51A through 51D are a set of two line graphs (FIGS. 51A, 51C) and two bar graphs (FIGS. 51B, 51D) showing glucose lowering effects (FIGS. 51A, 51B) and insulin-releasing activity (FIGS. 51C, 51D) of GIP and fatty acid derivatised GIP analogues in 18 hour-fasted ob/ob mice. Plasma glucose and insulin concentrations were measured prior to and after i.p. administration of glucose alone (18 mmoles/kg bw; ○; white bars) as a control, or in combination with GIP (▲; lined bars) or GIP analogues N-AcGIP(LysPAL16) (□; grey bars) and N-AcGIP(LysPAL37) (●; black bars) (25 nmoles/kg bw). The incremental area under the glucose or insulin curves (AUC) between 0 and 60 minutes are shown in the right panels. Values represent means±SEM for 8 mice. *$p<0.05$, $p<0.01$, *$p<0.001$ compared to glucose alone, $^\Delta p<0.05$, $^{\Delta\Delta}p<0.01$ and $^{\Delta\Delta\Delta}p<0.001$ compared to native GIP, $^{\gamma\gamma\gamma}p<0.001$ compared with N-AcGIP(LysPAL16).

Figure 52:
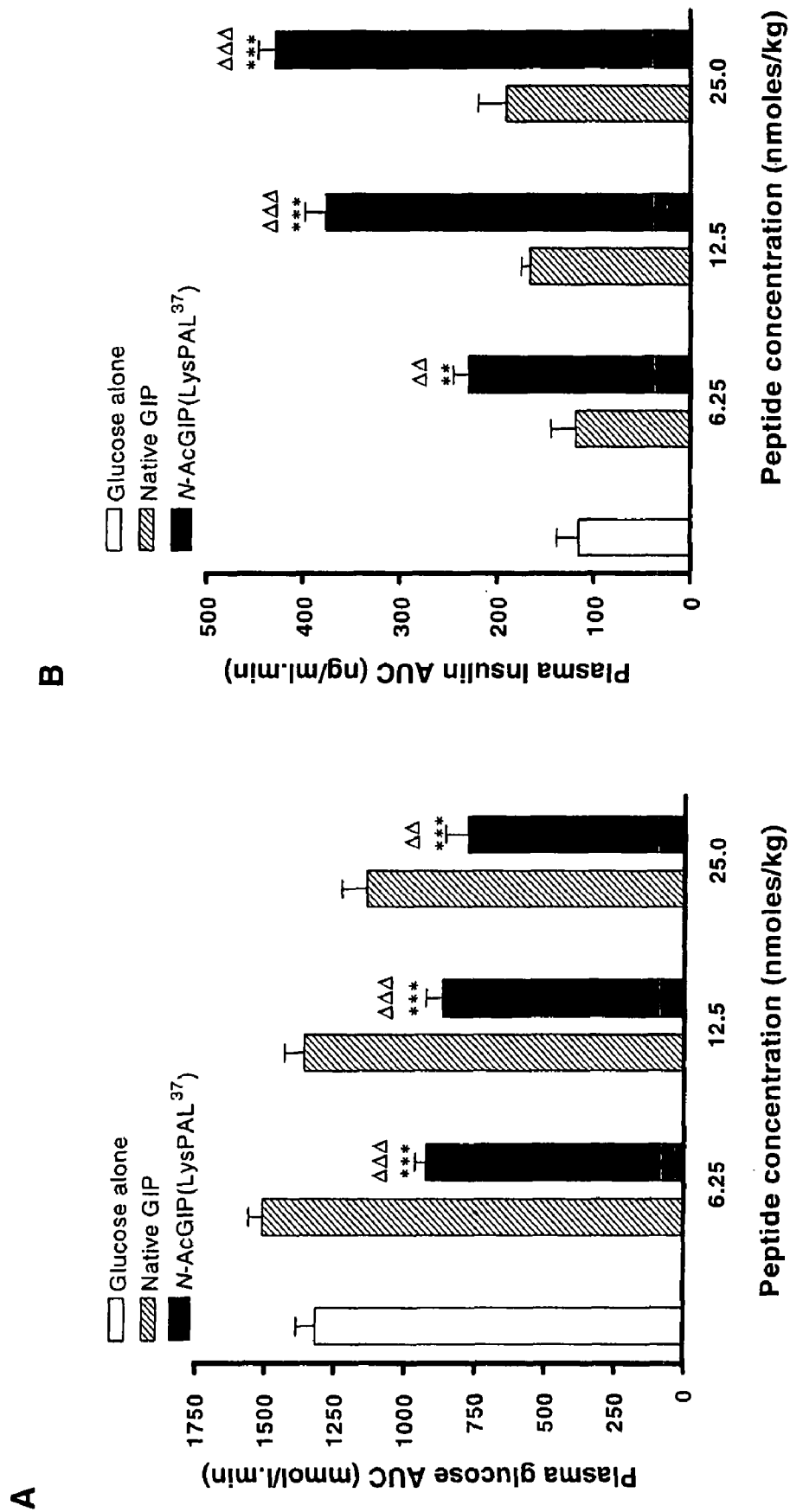
FIGS. 52A and 52B are a pair of bar graphs showing dose-dependent effects of GIP and N-AcGIP(LysPAL$^{37}$) in ob/ob mice fasted for 18 hours.

Basal blood glucose levels of the experimental groups were not significantly different at the start of the study ($p>0.05$). After injection of glucose alone, plasma glucose levels increased rapidly, attaining values of 40.3±1.5 mmol/l at 60 min. Native GIP reduced plasma glucose at each of the time points monitored, however, this failed to reach significance in terms of overall glucose excursion as revealed by the AUC values (FIG. 52B). Administration of N-AcGIP(LysPAL$^{16}$) and N-AcGIP(LysPAL$^{37}$) produced a significant reduction in plasma glucose at each time point ($p<0.01$ to $p<0.001$) and significantly lowered glucose AUC ($p<0.001$ to $p<0.001$) when compared to glucose alone. Additionally, N-AcGIP (LysPAL$^{16}$) and N-AcGIP(LysPAL$^{37}$) decreased the overall glucose excursion ($p<0.05$ to $p<0.001$) when compared to native GIP.

Figure 51:
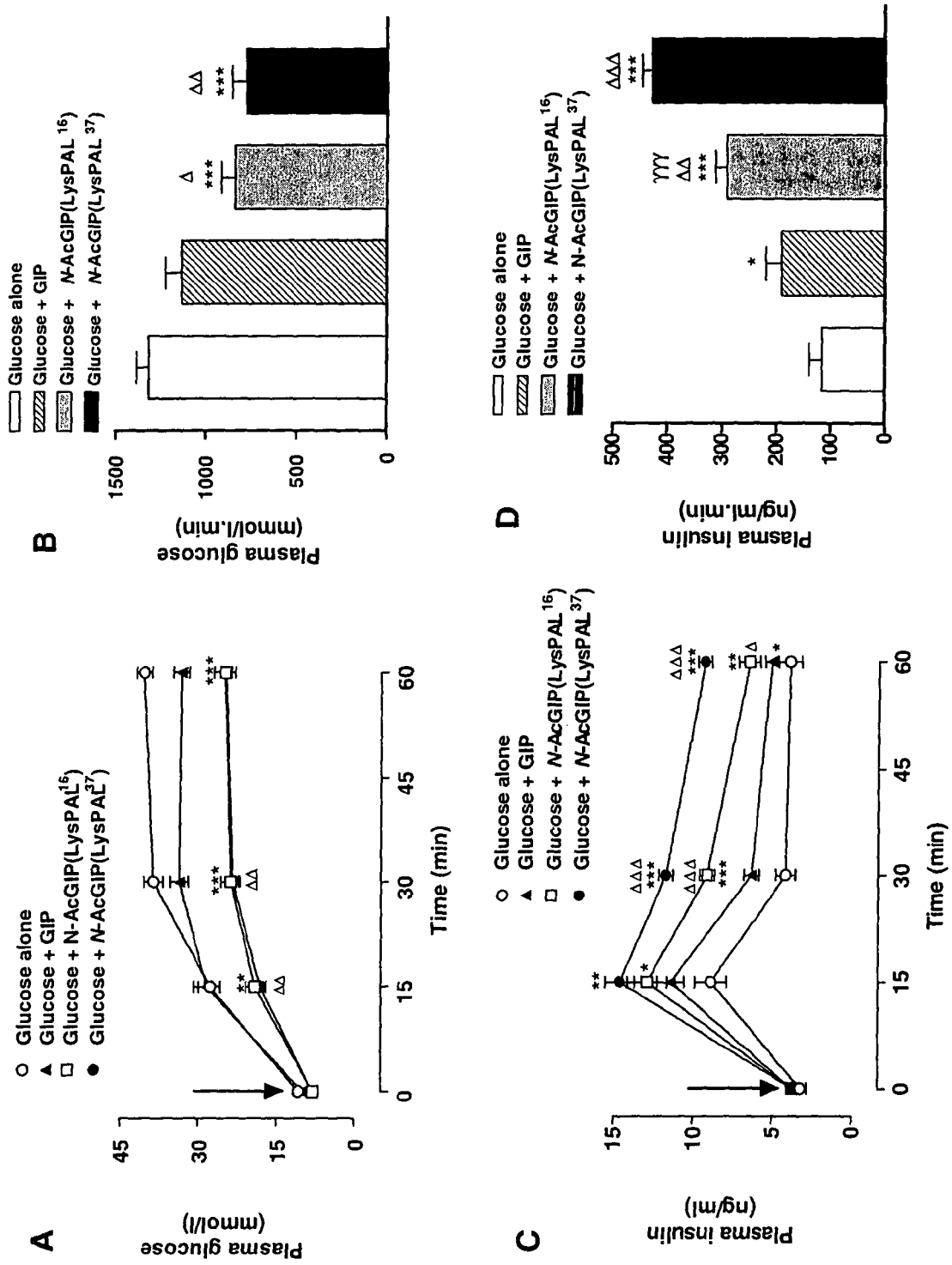
FIGS. 51A through 51D are a set of two line graphs (FIGS. 51A, 51C) and two bar graphs (FIGS. 51B, 51D) showing glucose lowering effects (FIGS. 51A, 51B) and insulin-releasing activity (FIGS. 51C, 51D) of GIP and fatty acid derivatised GIP analogues in 18 hour-fasted ob/ob mice.

The corresponding plasma insulin responses are illustrated in FIGS. 51C and 51D. After administration of glucose alone (control) the maximal rise in plasma insulin was observed at 15 minutes, which then fell towards basal levels over the remaining 45 minutes. Administration of native GIP significantly elevated the overall insulinotropic response ($p<0.05$) compared with glucose alone. When N-AcGIP(LysPAL$^{16}$) or N-AcGIP(LysPAL$^{37}$) where administered together with glucose, a maximum plasma insulin concentration was observed at 15 minutes. Protracted biological activity for both analogues was clearly evident from 30 to 60 minutes. Glucose-mediated plasma insulin concentrations were significantly higher compared in both control ($p<0.01$ to $p<0.001$) and GIP-treated animals ($p<0.05$ to $p<0.001$). The corresponding AUC values for N-AcGIP(LysPAL$^{16}$) and N-AcGIP(LysPAL$^{37}$) revealed significant enhancements in overall glucose-mediated insulin release compared to native GIP (1.5-fold and 2.3-fold, respectively; $p<0.01$ to $p<0.001$). N-AcGIP (LysPAL$^{37}$) was significantly more potent (1.5-fold: $p<0.001$) than N-AcGIP(LysPAL$^{16}$) at stimulating insulin secretion.

Dose-dependent metabolic effects in ob/ob mice. FIGS. 52A and 52B illustrate the dose-dependent antihyperglycaemic and insulinotropic effects of GIP and the more potent analogue N-AcGIP(LysPAL$^{37}$) when administered with glucose to ob/ob mice. They are a pair of bar graphs showing dose-dependent effects of GIP and N-AcGIP(LysPAL$^{37}$) in ob/ob mice fasted for 18 hours. The incremental area under the curve (AUC) for glucose (FIG. 52A) and insulin (FIG. 52B) between 0 and 60 minutes after i.p. administration of glucose alone (18 mmoles/kg bw; white bars) or in combination with GIP (lined bars) or N-AcGIP(LysPAL$^{37}$) (each at 6.25, 12.5 and 25 nmoles/kg bw; black bars). Values represent means±SEM for 8 mice. $p<0.01$ and *$p<0.001$ compared to glucose alone. $^{\Delta\Delta}p<0.01$ and $^{\Delta\Delta\Delta}p<0.001$ compared to native GIP at the same dose.

Data are presented as overall AUC responses for convenience. Expressed in this manner, native GIP did not significantly affect AUC glucose and insulin at any of the doses tested. N-AcGIP(LysPAL$^{37}$) was substantially more potent than native GIP ($p<0.01$ to $p<0.001$) and exhibited prominent dose-dependent antihyperglycaemic and insulinotropic actions at all doses administered (FIGS. 52A, 52B). Remarkably, even the lowest concentration of N-AcGIP(LysPAL$^{37}$) tested (6.25 nmoles/kg) had highly significant antihyperglycaemic properties compared to glucose alone ($p<0.001$). Consistent with this observation, 6.25 nmoles/kg N-AcGIP (LysPAL$^{37}$) elicited a prominent insulin response (2.0-fold; $p<0.01$) compared to glucose alone.

Figure 53:
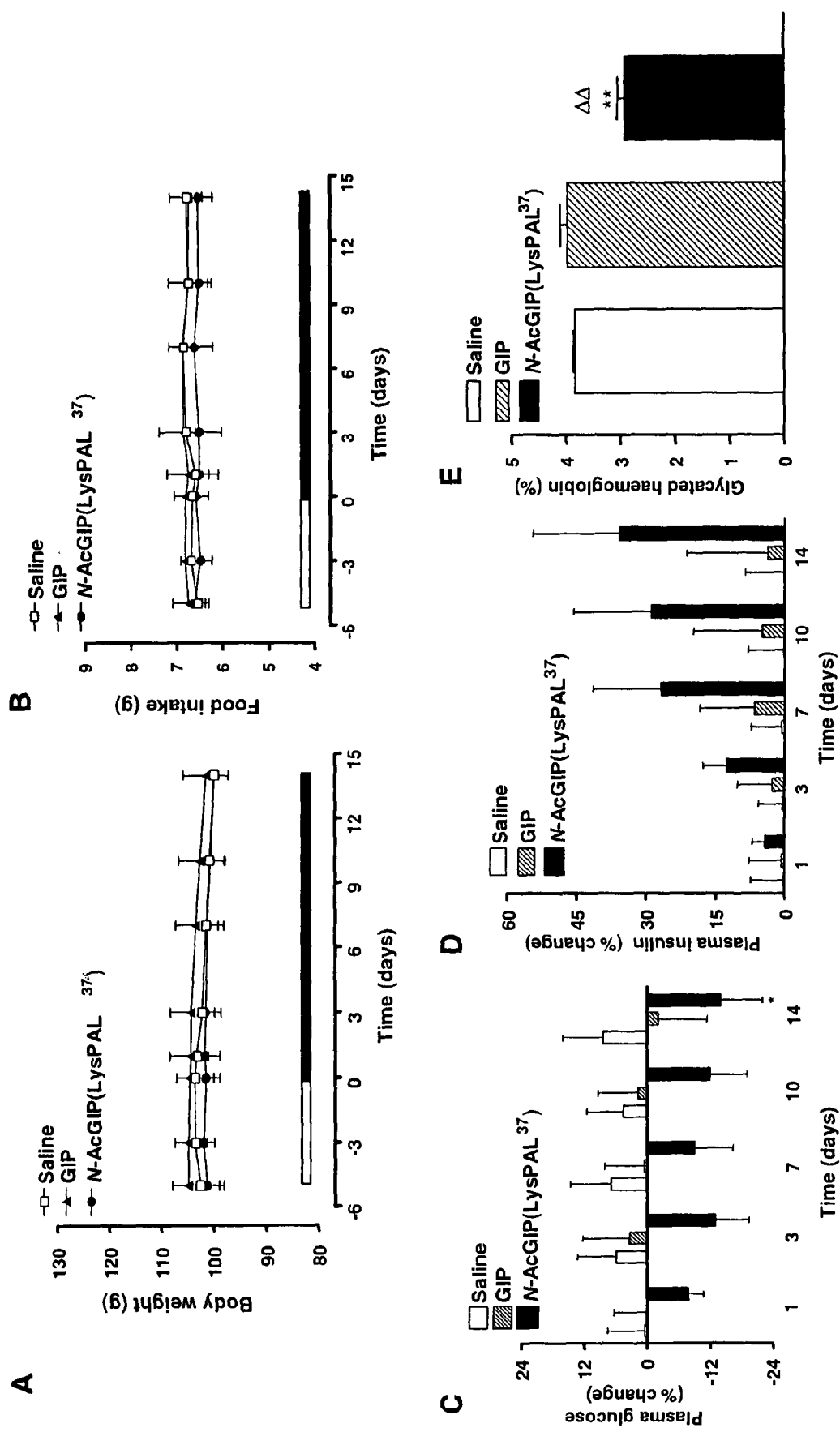
FIGS. 53A through 53E are a set of graphs showing the effects of daily N-AcGIP(LysPAL$^{37}$) (●; black bars) administration on food intake (FIG. 53A), body weight (FIG. 53B), plasma glucose (FIG. 53C), insulin (FIG. 53D) and glycated hemoglobin N-AcGIP(LysPAL$^{37}$) (12.5 nmoles/kg/day) (FIG. 53E).

Long-acting effects in ob/ob mice. The effects of daily injection of N-AcGIP(LysPAL$^{37}$) for 14 days on food intake, body weight, glycated hemoglobin and non-fasting plasma glucose and insulin concentrations of ob/ob mice are shown in FIGS. 53A through 53E, which are a set of graphs showing the effects of daily N-AcGIP(LysPAL$^{37}$) (●; black bars) administration on food intake (FIG. 53A), body weight (FIG. 53B), plasma glucose (FIG. 53C), insulin (FIG. 53D) and glycated hemoglobin N-AcGIP(LysPAL$^{37}$) (12.5 nmoles/kg/day) (FIG. 53E). Native GIP (12.5 nmoles/kg/day; ▲; lined bars) or saline vehicle (control; □; white bars) were administered for the 14-day period indicated by the horizontal black bar. Values are means±SEM for 8 mice. *$p<0.05$, **$p<0.01$ compared to control. $^{\Delta\Delta}p<0.01$ compared to native GIP.

GIP or N-AcGIP(LysPAL$^{37}$) had no effect on body weight or food intake (FIGS. 53A, 53B). Plasma glucose and insulin concentrations were also unchanged by treatment with native GIP for 14 days (FIGS. 53C, 53D). In contrast, daily injection of N-AcGIP(LysPAL$^{37}$) resulted in a progressive lowering of plasma glucose, resulting in significantly ($p<0.05$) lowered concentrations at 14 days (FIG. 53C). At this time, glycated hemoglobin was also significantly ($p<0.01$) decreased in N-AcGIP(LysPAL$^{37}$) treated ob/ob mice (FIG. 53E). These changes were accompanied by a tendency towards elevated insulin concentrations, but these did not achieve statistical significance over the time frame studies (FIG. 53D).

Effects of long term treatment of ob/ob mice with N-AcGIP(LysPAL$^{37}$) on glucose tolerance. FIGS. 54A through 54D are a set of two line graphs (FIGS. 54A, 54C) and two bar graphs (FIGS. 54B, 54D) showing the effects of daily N-AcGIP(LysPAL$^{37}$) administration on glucose tolerance (FIGS. 54A, 54B) and plasma insulin response (FIGS. 54C, 54D) to glucose. Tests were conducted after 14 daily injections of either N-AcGIP(LysPAL$^{37}$) (12.5 nmoles/kg/day; ●; black bars), native GIP (12.5 nmoles/kg/day; ▲; lined bars) or saline vehicle (control; □; white bars). Glucose (18 mmoles/kg) was administered by intraperitoneal injection at the time indicated by the arrow. Plasma glucose and insulin AUC values for 0-60 minutes post injection are shown in the right panels. Values are means±SEM for 8 mice. *$p<0.05$, $p<0.01$, *$p<0.001$ compared to control. $^{\Delta}p<0.05$, $^{\Delta\Delta}p<0.01$, $^{\Delta\Delta\Delta}p<0.001$ compared to native GIP.

Figure 54:
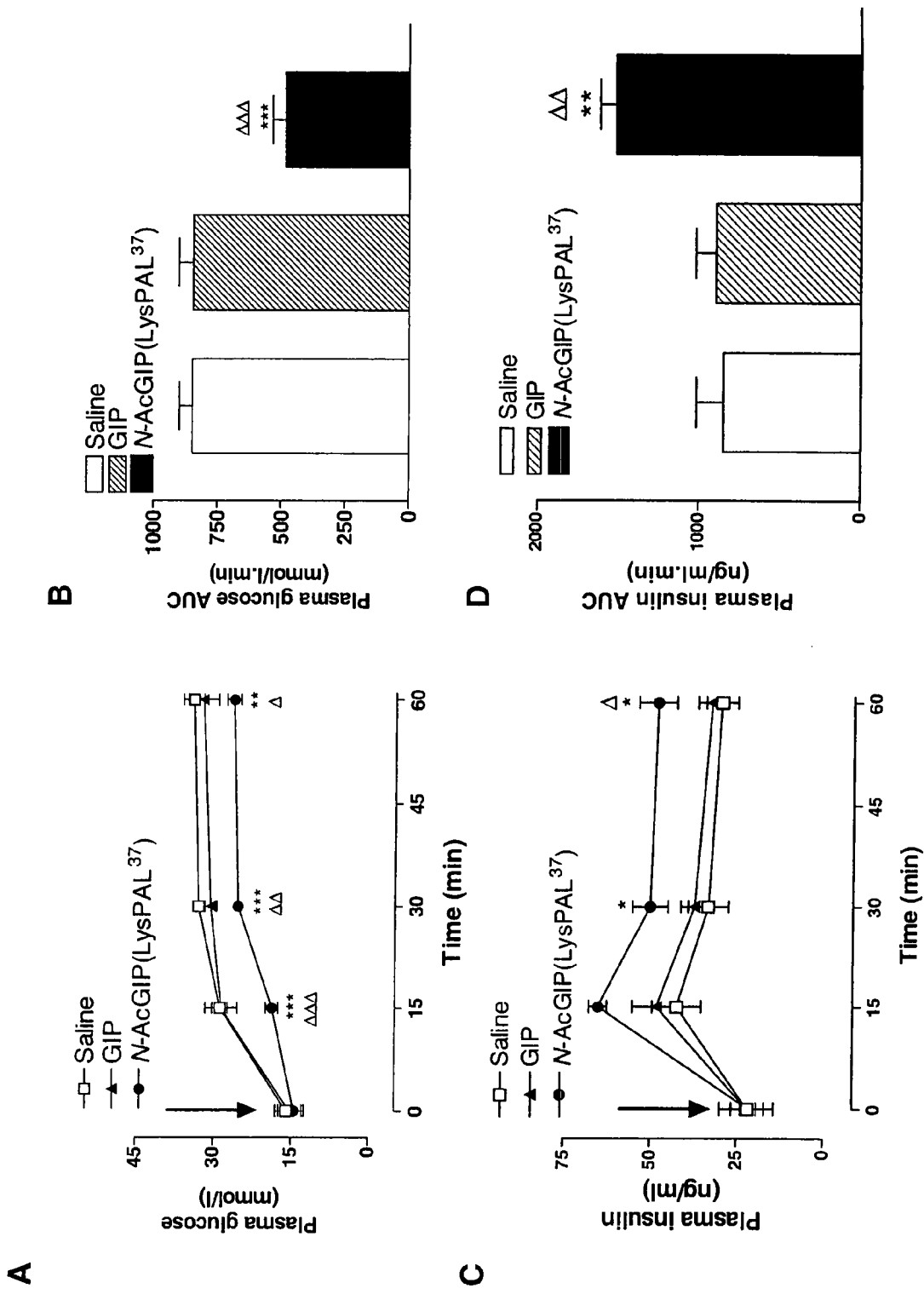
FIGS. 54A through 54D are a set of two line graphs (FIGS. 54A, 54C) and two bar graphs (FIGS. 54B, 54D) showing the effects of daily N-AcGIP(LysPAL$^{37}$) administration on glucose tolerance (FIGS. 54A, 54B) and plasma insulin response (FIGS. 54C, 54D) to glucose.

Consistent with effects on glycated hemoglobin, treatment of ob/ob mice for 14 days with N-AcGIP(LysPAL$^{37}$) resulted in a significant improvement in glucose tolerance (FIGS. 54A, 54B). Plasma glucose concentrations throughout the test and the overall 0-60 minutes AUC values were decreased ($p<0.01$ to $p<0.001$). This was accompanied by increased insulin concentrations during the latter stages ($p<0.05$) and a greater ($p<0.01$) overall AUC insulin response (FIGS. 54C, 54D). In contrast, daily administration of native GIP had no effect on glucose tolerance or the plasma insulin response to glucose compared with control ob/ob mice receiving saline injections for 14 days (FIG. 54).

Figure 55:
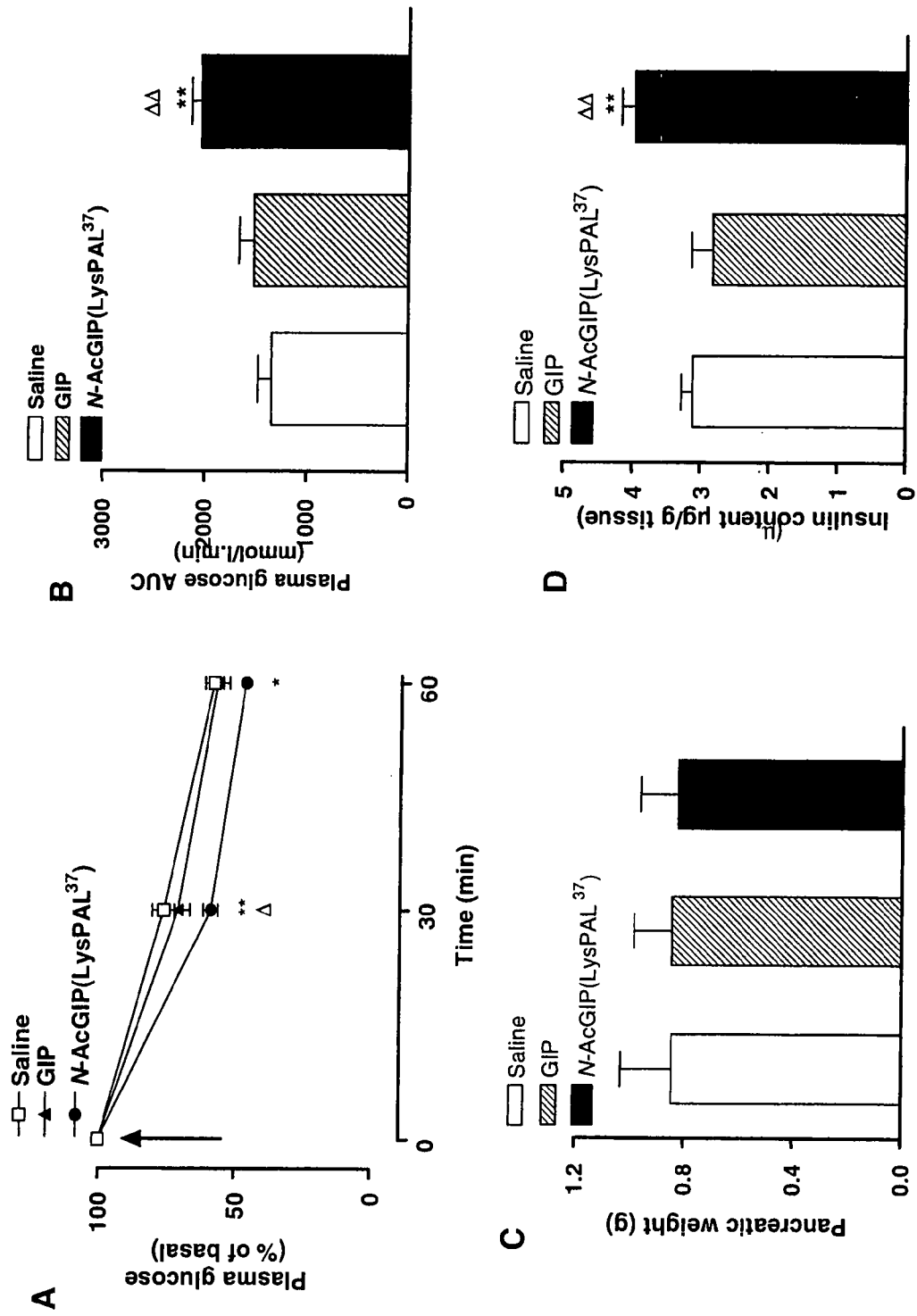
FIGS. 55A through 55D are a line graph and three bar graphs showing the effects of daily N-AcGIP(LysPAL$^{37}$) administration on insulin sensitivity (FIGS. 55A, 55B) and pancreatic weight (FIG. 55C) and insulin content (FIG. 55D).
Figure 56:
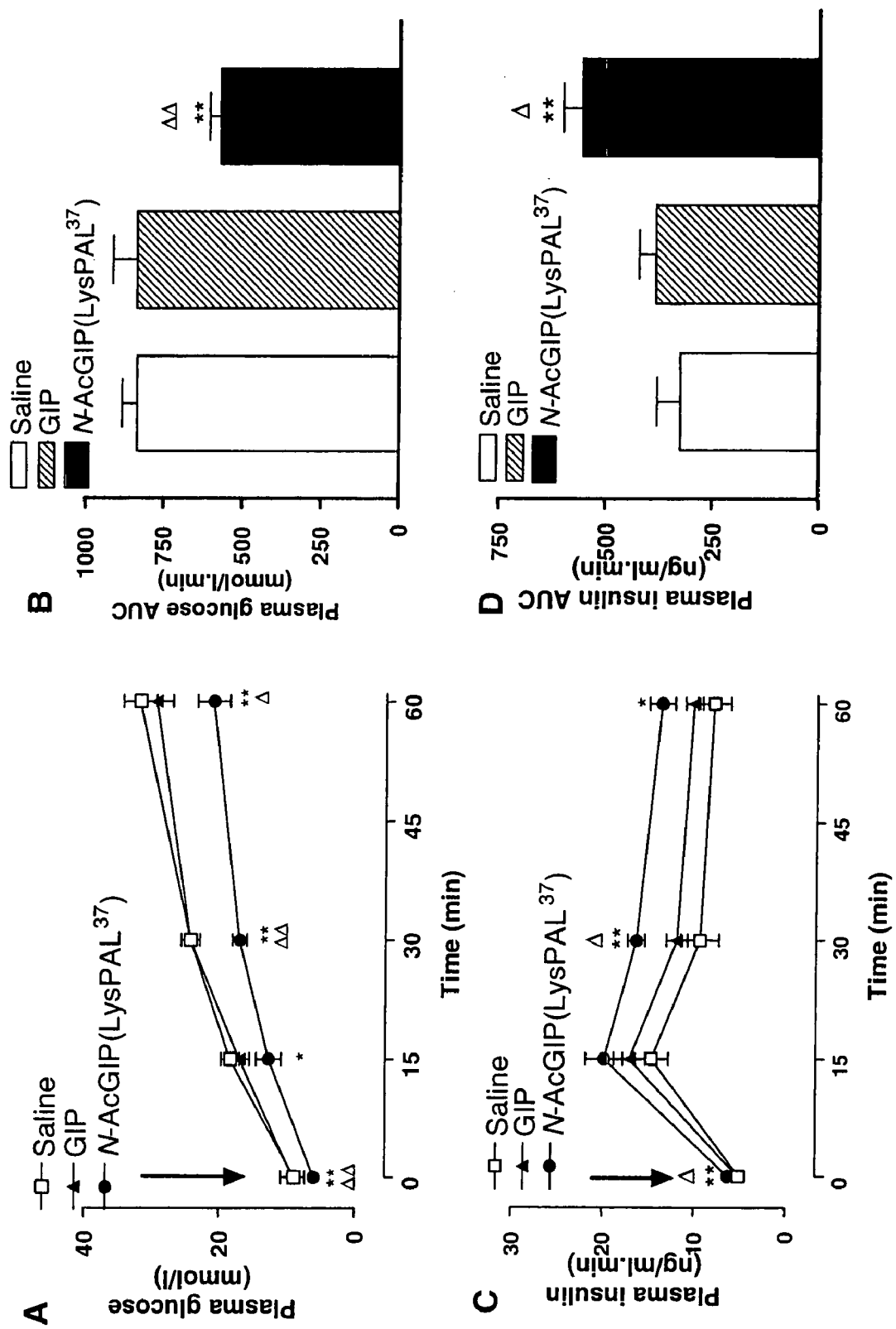
FIGS. 56A through 56D are a set of two line graphs (FIGS. 56A, 56C) and two bar graphs (FIGS. 56B, 56D) showing the retention of glucose lowering (FIGS. 56A, 56B) and insulin releasing (FIGS. 56C, 56D) activity of N-AcGIP(LysPAL$^{37}$) and native GIP after daily injection for 14 days.
Figure 57:
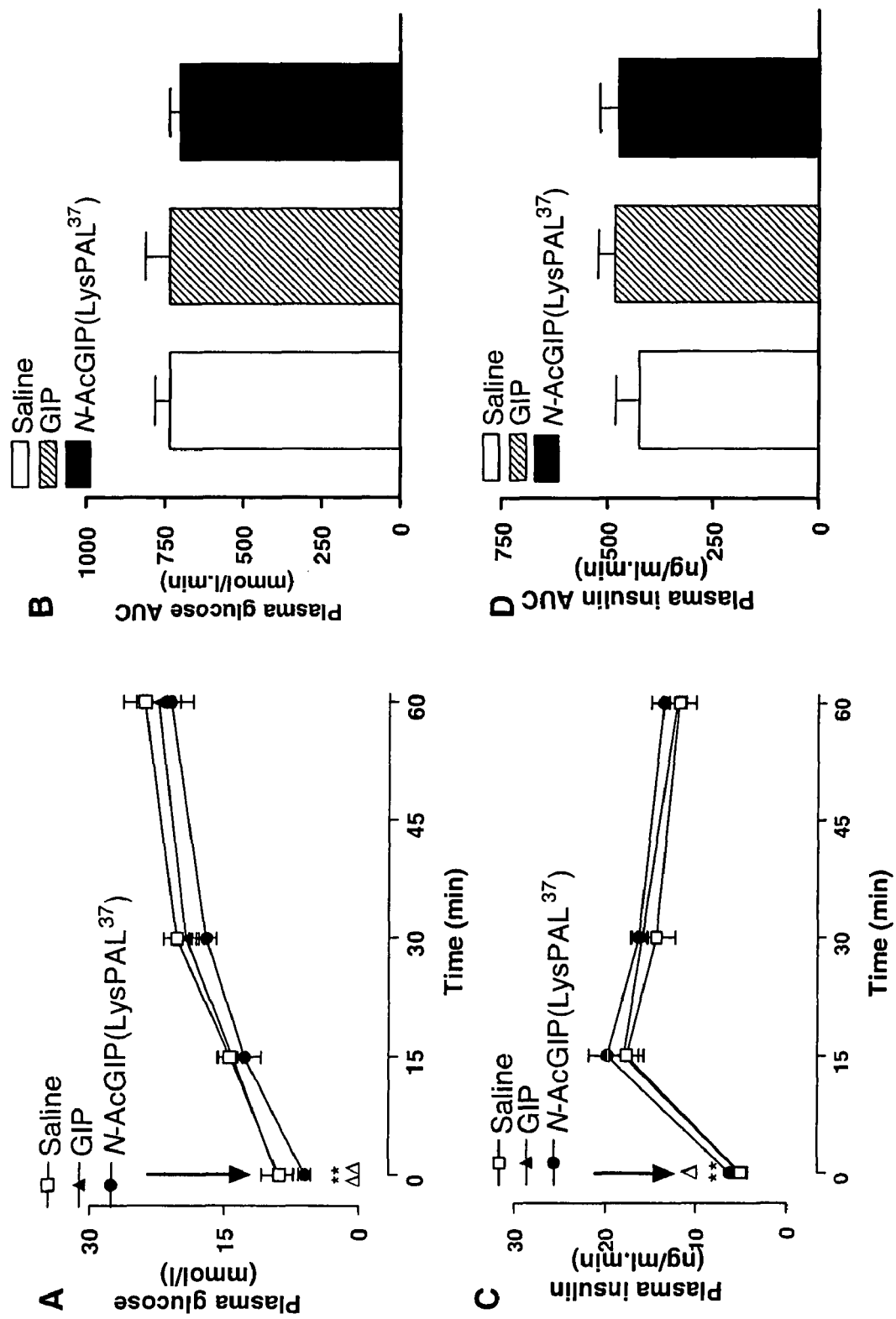
FIGS. 57A through 57D are a set of two line graphs (FIGS. 57A, 57C) and two bar graphs (FIGS. 57B, 57D) showing the acute glucose lowering (FIGS. 57A, 57B) and insulin releasing (FIGS. 57C, 57D) effects of N-AcGIP(LysPAL$^{37}$) after 14 daily injections of either N-AcGIP(LysPAL$^{37}$) (12.5 nmoles/kg/day; ●; black bars), native GIP (12.5 nmoles/kg/day; ▲; lined bars) or saline vehicle (control; □; white bars).

Effects long term treatment of ob/ob mice with N-AcGIP (LysPAL37) on insulin sensitivity, and effects of long term treatment of ob/ob mice with N-AcGIP(LysPAL$^{37}$) on pancreatic insulin content. FIGS. 55A through 55D are a line graph and three bar graphs showing the effects of daily N-AcGIP(LysPAL$^{37}$) administration on insulin sensitivity (FIGS. 55A, 55B) and pancreatic weight (FIG. 55C) and insulin content (FIG. 55D). Observations were conducted after 14 daily injections of either N-AcGIP(LysPAL$^{37}$) (12.5 nmoles/kg/day; ●; black bars), native GIP (12.5 nmoles/kg/day; ▲; lined bars) or saline vehicle (control; □; white bars). In FIG. 55A, insulin (50 U/kg) was administered by intraperitoneal injection at the time indicated by the arrow. Plasma glucose AUC values for 0-60 minutes post injection are shown in the right panels. Values are means±SEM for 8 mice. *$p<0.05$, **$p<0.01$ compared to control. $^{\Delta}p<0.05$, $^{\Delta\Delta}p<0.01$ compared to native GIP.

Insulin sensitivity of the 3 groups of mice after 14 days treatment is shown in FIGS. 55A, 55B. Compared with ob/ob mice receiving daily injections of saline or native GIP, N-AcGIP(LysPAL$^{37}$) prompted a significant improvement of insulin sensitivity. Both the individual glucose concentrations and 0-60 minutes AUC values were significantly different ($p<0.01$) from the other two groups. In contrast, daily treatment with native GIP did not affect the characteristic insulin resistance of ob/ob mice (FIG. 55A, 55B).

Treatment of ob/ob mice for 14 days with native GIP or N-AcGIP(LysPAL$^{37}$) did not affect pancreatic weight compared with saline-treated controls (FIGS. 55C, 55D). Similarly, pancreatic insulin content was similar in the GIP and saline treated groups. However, daily administration of N-AcGIP(LysPAL$^{37}$) significantly increased ($p<0.01$) insulin content compared with each of the other groups (FIGS. 55C, 55D).

Evaluation of GIP receptor desensitization after long term treatment of ob/ob mice with N-AcGIP(LysPAL$^{37}$). FIGS. 56A through 56D are a set of two line graphs (FIGS. 56A, 56C) and two bar graphs (FIGS. 56B, 56D) showing the retention of glucose lowering (FIGS. 56A, 56B) and insulin releasing (FIGS. 56C, 56D) activity of N-AcGIP(LysPAL$^{37}$) and native GIP after daily injection for 14 days. Glucose (18 mmoles/kg) was administered by intraperitoneal injection alone (□; white bars) or in combination with either N-AcGIP (LysPAL$^{37}$) (●; black bars) or native GIP (▲; lined bars) (both at 25 nmoles/kg) at the time indicated by the arrow. Plasma glucose and insulin AUC values for 0-60 minutes post injection are shown in the right panels. Values are means±SEM for 8 mice. *$p<0.05$, **$p<0.01$ compared to glucose alone. $^{\Delta}p<0.05$, $^{\Delta\Delta}p<0.01$ compared to native GIP. FIGS. 57A through 57D are a set of two line graphs (FIGS. 57A, 57C) and two bar graphs (FIGS. 57B, 57D) showing the acute glucose lowering (FIGS. 57A, 57B) and insulin releasing (FIGS. 57C, 57D) effects of N-AcGIP(LysPAL$^{37}$) after 14 daily injections of either N-AcGIP(LysPAL37) (12.5 nmoles/kg/day; ●; black bars), native GIP (12.5 nmoles/kg/day; ▲; lined bars) or saline vehicle (control; □; white bars). N-AcGIP(LysPAL$^{37}$) (25 nmoles/kg) was administered by intraperitoneal injection with glucose (18 mmoles/kg) at the time indicated by the arrow. Plasma glucose and insulin AUC values for 0-60 minutes post injection are shown in the right panels. Values are means±SEM for 8 mice. *$p<0.05$, **$p<0.01$ compared to mice receiving control injections. $^{\Delta}p<0.05$, $^{\Delta\Delta}p<0.01$ compared to group receiving injections of native GIP.

As shown in FIGS. 56A through 56D, treatment of ob/ob mice with N-AcGIP(LysPAL$^{37}$) for 14 days did not prevent the ability of the peptide to significantly moderate the glycaemic excursion ($p<0.01$) and enhance plasma insulin concentrations ($p<0.01$) when administered acutely with intraperitoneal glucose. In contrast, the responses of ob/ob mice to acute administration of native GIP were almost identical in mice receiving treatment with GIP or saline for 14 days (FIGS. 56A-56D). To further substantiate the lack of GIP receptor desensitization following chronic treatment with N-AcGIP(LysPAL$^{37}$), the acute effects of the analogue, administered with glucose, were examined in each of the 3 groups after 14 days treatment with N-AcGIP(LysPAL$^{37}$), native GIP or saline (FIGS. 57A-57D). Apart from lower basal values in the former group, the glucose and insulin responses were identical with similar 0-60 minutes AUC measures for both plasma glucose and insulin concentrations.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method of treating insulin resistance, the method comprising administering to a mammal in need of such treatment a therapeutically effective amount of a GIP receptor antagonist, the GIP receptor antagonist comprising a peptide analogue of GIP (1-42) (SEQ ID NO: 1), the peptide analogue selected from the group consisting of
   (i) at least 12 amino acid residues from the N-terminal end of GIP (3-42) wherein the amino acids at positions 1 and 2 of GIP (1-42) are absent; and
   (ii) at least 12 amino acid residues from the N-terminal end of GIP (1-42) and having an amino acid substitution at $Glu^3$ selected from the group consisting of hydroxyproline, lysine, tyrosine, phenylalanine, and tryptophan.

2. A method of treating obesity, the method comprising administering to a mammal in need of such treatment a therapeutically effective amount of a GIP receptor antagonist, the GIP receptor antagonist comprising a peptide analogue of GIP (1-42) (SEQ ID NO: 1), the peptide analogue selected from the group consisting of
   (i) at least 12 amino acid residues from the N-terminal end of GIP (3-42) wherein the amino acids at positions 1 and 2 of GIP (1-42) are absent; and
   (ii) at least 12 amino acid residues from the N-terminal end of GIP (1-42) and having an amino acid substitution at $Glu^3$ selected from the group consisting of hydroxyproline, lysine, tyrosine, phenylalanine, and tryptophan.

3. A method of treating insulin resistance, the method comprising administering to a mammal in need of such treatment a therapeutically effective amount of a peptide analogue of GIP (1-42) (SEQ ID NO: 1), wherein the analogue comprises a base peptide selected from the group consisting of GIP (1-16), GIP (1-17), GIP (1-18), GIP (1-19), GIP (1-20), GIP (1-21), GIP (1-22), GIP (1-23), GIP (1-24), GIP (1-25), GIP (1-26), GIP (1-27), GIP (1-28), GIP (1-29), GIP (1-30), GIP (1-31), GIP (1-32), GIP (1-33), GIP (1-34), GIP (1-35), GIP (1-36), GIP (1-37), GIP (1-38), GIP (1-39), GIP (1-40), GIP (1-41) and GIP (1-42);
   wherein the base peptide is modified by N-terminal acetylation and by palmitate fatty acid addition at an epsilon amino group of at least one lysine residue.

4. A method of treating obesity, the method comprising administering to a mammal in need of such treatment a therapeutically effective amount of a peptide analogue of GIP (1-42) (SEQ ID NO: 1), wherein the analogue comprises a base peptide selected from the group consisting of GIP (1-16), GIP (1-17), GIP (1-18), GIP (1-19), GIP (1-20), GIP (1-21), GIP (1-22), GIP (1-23), GIP (1-24), GIP (1-25), GIP (1-26), GIP (1-27), GIP (1-28), GIP (1-29), GIP (1-30), GIP (1-31), GIP (1-32), GIP (1-33), GIP (1-34), GIP (1-35), GIP (1-36), GIP (1-37), GIP (1-38), GIP (1-39), GIP (1-40), GIP (1-41) and GIP (1-42);
   wherein the base peptide is modified by N-terminal acetylation and by palmitate fatty acid addition at an epsilon amino group of at least one lysine residue.

5. The method of claim 1, further comprising modification by fatty acid addition at an epsilon amino group of at least one lysine residue.

6. The method of claim 5, wherein the modification is the linking of a C-16 palmitate group to the epsilon amino group of a lysine residue.

7. The method of claim 6, wherein the lysine residue is $Lys^{16}$.

8. The method of claim 6, wherein the lysine residue is $Lys^{37}$.

9. The method of claim 2, further comprising modification by fatty acid addition at an epsilon amino group of at least one lysine residue.

10. The method of claim 9, wherein the modification is the linking of a C-16 palmitate group to the epsilon amino group of a lysine residue.

11. The method of claim 10, wherein the lysine residue is $Lys^{16}$.

12. The method of claim 10, wherein the lysine residue is $Lys^{37}$.

* * * * *

SEQUENCE LISTING

<160> NUMBER OF SEQ ID NOS: 2

<210> SEQ ID NO 1
<211> LENGTH: 42

```
-continued

<212> TYPE: PRT
<213> ORGANISM: Homo sapiens

<400> SEQUENCE: 1

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 2
<211> LENGTH: 42
<212> TYPE: PRT
<213> ORGANISM: Pig

<400> SEQUENCE: 2

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Lys His Asn Ile Thr Gln
            35                  40
```